United States Patent
Fong et al.

(10) Patent No.: US 10,413,574 B2
(45) Date of Patent: Sep. 17, 2019

(54) WOUND DRESSING NANOMESH IMPREGNATED WITH HUMAN UMBILICAL CORD WHARTON'S JELLY STEM CELLS

(71) Applicant: National University of Singapore, Singapore (SG)

(72) Inventors: Chui Yee Fong, Singapore (SG); Mahesh Choolani, Singapore (SG); Arijit Biswas, Singapore (SG); Tuan Ariffeen Bongso, Singapore (SG); Seeram Ramakrishna, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 14/421,676

(22) PCT Filed: Aug. 15, 2013

(86) PCT No.: PCT/SG2013/000348
§ 371 (c)(1),
(2) Date: Feb. 13, 2015

(87) PCT Pub. No.: WO2014/027965
PCT Pub. Date: Feb. 20, 2014

(65) Prior Publication Data
US 2015/0352157 A1     Dec. 10, 2015

Related U.S. Application Data

(60) Provisional application No. 61/683,391, filed on Aug. 15, 2012.

(51) Int. Cl.
*A61K 35/51*      (2015.01)
*C12N 5/073*      (2010.01)
(Continued)

(52) U.S. Cl.
CPC ............ *A61K 35/51* (2013.01); *A61K 36/886* (2013.01); *A61L 15/26* (2013.01); *A61L 15/40* (2013.01);
(Continued)

(58) Field of Classification Search
None
See application file for complete search history.

(56) References Cited

U.S. PATENT DOCUMENTS 8,858,988 B2 * 10/2014 Chamberland ...... A61K 36/324
                                                              424/195.17
9,315,776 B2    4/2016 Fong et al.
(Continued)

FOREIGN PATENT DOCUMENTS

KR       2010-0114729 A     10/2010
WO       WO 2006/036130 A1   4/2006
(Continued)

OTHER PUBLICATIONS

Venugopal et al "In Vitro Culture of Human Dermal Fibroblasts on Electrospun Polycarpolactone Collagen nanfibrous Membrane" Artificial Organs, 2006, vol. 30, No. 6, pp. 440-446.*
(Continued)

*Primary Examiner* — Allison M Fox
(74) *Attorney, Agent, or Firm* — Hamilton, Brook, Smith & Reynolds, P.C.

(57) ABSTRACT

The invention is directed to a method of treating a wound (e.g., to suppress scar formation) in an individual in need thereof comprising contacting the wound with an effective amount of a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a
(Continued)

combination thereof. The invention is directed to a medical dressing (e.g., pharmaceutical compositions) comprising Wharton's jelly stem cells (WJSCs), a cell culture medium that has been conditioned with WJSCs, a lysate of WJSCs, a cell culture medium that has been conditioned with WJSCs exposed to apoptotic skin cells and keloid cells, or a combination thereof.

22 Claims, 25 Drawing Sheets

Specification includes a Sequence Listing.

(51) Int. Cl.

| | |
|---|---|
| A61K 36/886 | (2006.01) |
| A61L 27/18 | (2006.01) |
| A61L 27/36 | (2006.01) |
| A61L 27/38 | (2006.01) |
| A61L 27/54 | (2006.01) |
| A61L 27/56 | (2006.01) |
| A61L 15/26 | (2006.01) |
| A61L 15/40 | (2006.01) |
| A61L 15/42 | (2006.01) |
| A61L 15/44 | (2006.01) |

(52) U.S. Cl.
CPC .............. *A61L 15/425* (2013.01); *A61L 15/44* (2013.01); *A61L 27/18* (2013.01); *A61L 27/3637* (2013.01); *A61L 27/3834* (2013.01); *A61L 27/54* (2013.01); *A61L 27/56* (2013.01); *C12N 5/0605* (2013.01); *A61L 2300/104* (2013.01); *A61L 2300/30* (2013.01); *A61L 2300/406* (2013.01); *A61L 2300/418* (2013.01); *A61L 2300/64* (2013.01); *A61L 2400/12* (2013.01)

(56) References Cited

U.S. PATENT DOCUMENTS

| | | | |
|---|---|---|---|
| 9,402,388 | B2 | 8/2016 | Fong et al. |
| 2004/0072259 | A1 | 4/2004 | Scadden et al. |
| 2007/0166825 | A1 | 7/2007 | Hatsuyama et al. |
| 2008/0118477 | A1 | 5/2008 | Christopherson |
| 2008/0220520 | A1 | 9/2008 | Palecek et al. |
| 2013/0121972 | A1* | 5/2013 | Taghizadeh ......... A61L 27/3834 424/93.7 |
| 2013/0302285 | A1 | 11/2013 | Fong et al. |
| 2014/0120615 | A1 | 5/2014 | Fong et al. |

FOREIGN PATENT DOCUMENTS

| | | |
|---|---|---|
| WO | WO 2007/046775 A1 | 4/2007 |
| WO | WO 2008/060377 A2 | 5/2008 |
| WO | WO 2011/101760 A1 | 8/2011 |
| WO | WO 2011/120535 A1 | 10/2011 |

OTHER PUBLICATIONS

Carvalho et al, Current Stem Cell Research & Therapy, 2011, vol. 6, pp. 221-228. (Year: 2011).*
Sarugaser et al, Stem Cells, 2005, vol. 23, pp. 220-229. (Year: 2005).*
Xu et al, Stem Cells International, 2017, Article ID 3175748, 15 pages. (Year: 2017).*
Advisory Action for U.S. Appl. No. 13/667,370, "Wharton's Jelly Mesenchymal Stem Cells and Uses Thereof"; dated Feb. 5, 2015.
Applicant Initiated Interview Summary for U.S. Appl. No. 13/667,370, "Wharton's Jelly Mesenchymal Stem Cells and Uses Thereof"; dated Feb. 26, 2015.
Applicant Initiated Interview Summary for U.S. Appl. No. 14/069,557, "Methods of Freezing Stem Cells"; dated Aug. 10, 2015.
Final Office Action for U.S. Appl. No. 14/069,557, "Methods of Freezing Stem Cells"; dated Dec. 8, 2015.
Notice of Allowance for U.S. Appl. No. 13/667,370, "Wharton's Jelly Mesenchymal Stem Cells and Uses Thereof"; dated Dec. 15, 2015.
Notice of Allowance for U.S. Appl. No. 14/069,557, "Methods of Freezing Stem Cells"; dated Apr. 20, 2016.
Notification Concerning Transmittal of International Preliminary Report on Patentability for International Patent Application No. PCT/SG2013/000348, "Wound Dressing Nanomesh Impregnated with Human Umbilical Cord Wharton's Jelly Stem Cells", dated Feb. 26, 2015.
Final Office Action for U.S. Appl. No. 13/667,370, "Wharton's Jelly Mesenchymal Stem Cells and Uses Thereof", dated Oct. 21, 2014.
Non-Final Office Action for U.S. Appl. No. 13/667,370, "Wharton's Jelly Mesenchymal Stem Cells and Uses Thereof", dated Mar. 13, 2014.
Non-Final Office Action for U.S. Appl. No. 13/667,370, "Wharton's Jelly Mesenchymal Stem Cells and Uses Thereof", dated May 14, 2015.
Non-Final Office Action for U.S. Appl. No. 14/069,557 "Methods of Freezing Stem Cells" dated May 8, 2015.
Akino, K., et al., "Human Mesenchymal Stem Cells May Be Involved in Keloid Pathogenesis", *International Journal of Dermatology*, 47(11): 1112-1117 (2008).
Al-Anazi, K., "Autologous Hematopoietic Stem Cell Transplantation for Multiple Myeloma Without Cryopreservation", *Bone Marrow Research*, Article ID 971361: 7 pages (2012).
Ayuzawa, R., et al., "Naïve Human Umbilical Cord Matrix Derived Stem Cells Significantly Attenuate Growth of Human Breast Cancer Cells In Vitro and In Vivo", *Cancer Letters*, 280: 31-37 (2009).
Azari, O., et al., "Effects of Transplanted Mesenchymal Stem Cells Isolated from Wharton's Jelly of Caprine Umbilical Cord on Cutaneous Wound Healing: Histopathological Evaluation," *Veterinary Research Communications*, vol. 35, pp. 211-222 (2011).
Badiavas, E.V. and Falanga, V., "Treatment of Chronic Wounds With Bone Marrow-Derived Cells", *Arch Dertmatol*, 139 510-516 (2003).
Badiavas, E.V., et al., "Participation of Bone Marrow Derived Cells in Cutaneous Wound Healing", *Journal of Cellular Physiology*, 196: 245-250 (2003).
Baharvand, H., et al., "An Efficient and Easy-To-Use Cryopreservation Protocol for Human ES and iPS Cells", *Nat Protoc*, 5(3): 588-594 (2010).
Bakhshi, T., et al., "Mesenchymal Stem Cells From the Wharton's Jelly of Umbilical Cord Segments Provide Stromal Support for the Maintenance of Cord Blood Hematopoietic Stem Cells During Long-Term Ex Vivo Culture", *Transfusion*, 48(12): 2638-2644 (2008).
Bao P, et al., "The Role of Vascular Endothelial Growth Factor in Would Healing", *J Surg Res*, 153:347-358 (2009).
Berz, D., et al., "Cryopreservation of Hemaotpoietic Stem Cells", *American Journal of Hematology*, 82: 463-472 (2007).
Bey, E., et al., "Emerging Therapy for Improving Wound Repair of Severe Radiaiton Burns Using Local Bone Marro-Derived Stem Cell Administrations", *Wound Repair and Regeneration*, 18:50-58 (2010).
Bielefeld, K.A., et al., "Fibronectin and β-Catenin Act in a Regulatory Loop in Dermal Fibroblasts to Modulate Cutaneous Healing", *J Biol Chem*, 286(31) :27687-27697 (Aug. 5, 2011).
Bissel, M.J. and RAdisky, D., "Putting Tumours in Context", *Nat Rev Cancer*, 1(1): 45-54 (2001).
Blankenstein, T., "The Role of Tumor Stroma in the Interaction Between Tumor and Immune System", *Current Opinion in Immunology*, 17: 180-186 (2005).
Blit, P.H. and Jeschke, M.G., "Keloids: Whe Do We Know and What Do We Do Next?", *Transl Res*, 159(3): 173-174 (2012).
Bongso, A, et al., "The Therapeutic Potention, Challenges and Future Clinical Directions of Stem Cells from the Wharton's Jelly of the Human Umbilical Cord", *Stem Cell Reviews and Reports*, 9:226-240 (2013).

(56) References Cited

OTHER PUBLICATIONS

Borne, X., et al., "Bone Marrow-Derived Cells Contribute to Epithelial Engraftment During Wound Healing", *American Journal of Pathology*, 165(5): 1767-1772 (2004).
Brower, J., et al.,"Mesenchymal Stem Cell Therapy and Delivery Systems in Nonhealing Wounds", *Advances in Skin & Wound Care*, 24:524-532 (2011).
Broxmeyer, H.E., "Insights Into the Biology of Cord Blood Stem/Progenitor Cells", *Cell Proliferation*, 44: 55-59 (2010).
Bueno, C., et al., The ROCK Inhibitor Y-27632 Negatively Affects the Expansion/Survival of Both Fresh and Cryopreserved Cord Blood-Derived CD34+ Hematopoietic Progenitor Cells, *Stem Cell Rev and Rep*, 6: 215-223 (2010).
Cabrera, C., et al., The Role of Biologically Active Peptides in Tissue Repair Using Umbilical Cord Mesenchymal Stem Cells, *Annals of the New York Academy of Sciences*, 1270: 93-97 (2012).
Cardone. A., et al., "Prognoostic Value of Desmoplastic Reaction and Lyphocytic Infiltration in the Management of Breast Cancer", *Panminerva Med*, 39(3):174-177 (1997).
Chao, K.C., et al.,"Human Umbilical Cord MEsenchymal Stem Cells Suppress Breast Cancer Tumourigenesis Through Direct Cell-Cell Contact and Internalization", *J Cell Mol Med*, 16(8): 1803-1815 (2012).
Chao, K.C., et al., "Islet-Like Clusters Derived From Mesenchymal Stem Cells in Wharton's Jelly of the Human Umbilical Cord for Transplantation to Control Type I Diabetes" *PlosOne*, e1451: 9 pages (2008).
Chen, L, et al., "Analysis of Allogenicity of Mesenchymal Stem Cells in Engraftment and Wound Healing in Mice", *PLOS One*, 4(9): e7119; 7 pgs. (2009).
Chithra, P., et al., "Influence of Aloe Vera on Collagen Characteristics in Healing Dermal Wounds in Rats", *Molecular and Cellular Biochemistry* 181: 71-76 (1998).
Chithra, P., et al., "Influence of Aloe Vera on the Healing of Dermal Wounds in Diabetic Rats", *J Ethnopharmacol*, 56(3): 195-201 (1998).
Clark, R., "Fibronectin Matrix Deposition and Fibronectin Receptor Expression in Healing and Normal Skim", *J Invest Dermatol*, 94(6):128S-134S (Jun. 1990).
Clarke, D.M., et al., "Improved Post-Thaw Recovery of Peripheral Blood Stem/Progenitor Cells Using a Novel Intracellular-Like Cryopreservation Solution", *Cytotherapy*, 11(4): 472-479 (2009).
Cory, G., "Scratch-Wound Assay", *Methods Mol Biol*, 769: 25-30 (2011).
de Boer, F., et al., "Early Apoptosis Largely Accounts for Functional Impairment of CD34+ Cells in Frozen-Thawed Stem Cell Grafts", *J Hematother Stem Cell Res*, 11(6): 951-963 (2002).
de Boer, F., et al., "Extensive Early Apoptosis in Frozen-Thawed CD24-positive Stem Cells Decreases Threshold Doses for Haematological Recovery After Autologous Peripheral Blood Progenitor Cell Transplantation", *Bone Marrow Transplantation*, 29: 249-255 (2002).
Dominici, M., et al., "Minimal Criteria for Defining Multipotent Mesenchymal Stromal Cells. The International Society for Cellular Therapy Position Statement", *Cytotherapy*, 8(4): 315-317 (2006).
Durand, E.M. and Zon, L.I., "Newley Emerging Roles for Prostaglandin $E_2$ Regulation of Hematopoiesis and Hematopoietic Stem Cell Engraftment", *Current Opinion in Hematology*, 17: 308-312 (2010).
Ehrlich, H.P., et al., "Morphological and Immunochemical Differences Between Keloid and Hypertrophic Scar", *American Journal of Pathology*, 145(1): 105-113 (1994).
Estes, J.M., et al., "Hyaluronate Metabolism Undergoes an Ontogenic Transiton During Fetal Development: Implications for Scar-Free Wound Healing", *J Pediatr Surg*, 28(10): 1227-1231 (1993).
Fan, C.G., et al., "Therpeutic Potentials of Mesenchymal Stem Cells Derived From Human Umbilical Cord", *Stem Cell Rev and Rep*, 7(1): 195-207 (2011).
Fathke, C. et al., "Contribution of Bone Marrow-Derived Cells to Skim: Collagen Deposition and Wound Repair", *Stem Cells*, 22:812-822 (2004).

Fernandes, K.J.L., et al., "A Dermal Niche for Multipotent Adult Skin-Derived Precursor Cells", *Nature Cell Biology*, 6(11):1082-1093 plus 5 pages of Supplemental Information (2004).
Fleming, K.K. and Hubel, A., "Cryopreservation of Hematopoietic STem Cells: Emerging Science, Technology and Issues", *Transfusion Medicine and Hemotherapy*, 34: 268-275 (2007).
Fong, C., et al., "Comparative growth behavior and characterization of stem cells from Human Wharton's Jelly", *Reprod Biomed online*, 15(6):708-718 (2007).
Fong, C., et al., "Derivation efficiency, cell proliferation, freeze-thaw survival, stem-cell properties and differentiation of human Wharton's jelly stem cells" *Reprod Biomed Online*, 21:391-401, (2010).
Fong, C., et al., "Human Umbilical Cord Wharton's Jelly Stem Cells and Its Conditioned Medium Support Hematopoietic Stem Cell Expansion Ex Vivo", *J Cell Biochem*, 113:658-668 (2012).
Fong, C., et al., "Human Umbilical Cord Wharton's Jelly Stem Cells Undergo Enhanced Chondrogenic Differentiation when Grown on Nanofibrous Scaffolds and in a Sequential Two-stage Culture Medium Environment", *Stem Cell Rev and Rep*, 8:195-209 (2012).
Fong, C.Y., et al., "Human Wharton's Jelly Stem Cells Have Unique Transciptome Profiles Compared to Human Embryonic Stem Cells and Other Mesenchymal Stem Cells", *Stem Cell Rev*, 7(1): 1-16 (2011).
Fonseka, M., et al., "Human Umbilical Cord Blood-Derived Mesenchymal Stem Cells (hUCB-MSC) Inhibit the Proliferation of K562 (Human Erythromyeloblastoid Leukaemic Cell Line)", *Cell Biol Int*, 36: 793-801 (2012).
Ganta, C., et al., "Rat Umbilical Cord Stem Cells Completely Abolish Rat Mammary Carcinomas With No Evidence of Metastasis or Recurrence 100 Days Post-Tumor Cell Inoculation", *Cancer Res*, 69(5): 1815-1820 (2009).
Garin, M.I., et al., "Ex Vivo Expansion and Charachtersation of CD34+ Cells Derived From Chronic Myeloid Leukaemia Bone Marrow and Peripheral Blood, and From Normal Bone Marrow and Mobilised Peripheral Blood", *Eur J Haematol*, 64(2): 85-92 (2000).
Gauglitz, G.G., "Management of Keloids and Hypertrophic Scars: Current and Emerging Options", *Clinical, Cosmetic and Investigational Dermatology*, 6: 103-114 (2013).
Gauglitz, G.G., et al., Hypertrophic Scarring and Keloids: Pathomechanisms and Current and Emerging Treatment Strategies, *Mol Med*, 17: 113-125 (2011).
Gauthaman K, et al., "Extra-embryonic human Wharton's jelly stem cells do not induce tumorigenesis, unlike human embryonic stem cells", *Reprod BioMed Online*, 24:235-246 (2012).
Gauthaman, K., et al, "Human Wharton's Jelly Stem Cell Conditioned Medium and Cell-Free Lysate Inhibit Human Osteosarcoma and Mammary Carcinoma Cell Growth In Vitro and in Xenograft Mice", J Cell Biochem, 114(2): 366-377 (2013).
Gauthaman, K., et al., "Human Umbilical Cord Wharton's Jelly Stem Cell (hWJSC) Extracts Inhibit Cancer Cell Growth in Vitro", et al., *J Cell Biochem*, 113:2027-2039 (2012).
Gauthaman, K., et al., "Osteogenic Differentiation of Human Wharton's Jelly Stem Cells on Nanofibrous Substrates In Vitro", Tissue Engineering Part A, 17 (1-2): 71-81 (2011).
Gauthaman, K., et al., "ROCK, Inhibitor Y-27632 Increase Thaw-Survival Rates and Preserves Stemness and Differentiation Potential of Human Wharton's Jelly Stem Cells After Cryopreservation", Stem Cell Rev and Rep, 6(4): 665-676 (2010).
Gay, A.N., et al., "Wound Healing Characteristics of ICAM-1 Null Mice Devoid of All Isoforms of ICAM-1", *J Surg Res*, 171(1):e1-e7 (2011).
Gluckman, E., et al., "Cord Blood Transplantation: State of the Art", *Haematologica*, 94(4): 451-454 (2009).
Gluckman, E., et al., "Outcome of cord-Blood Transplantation From Related and Unrelated Donors", *NEJM*, 337(6): 373-381 (1997).
Hamann, K.J., et al., "Hyaluronic Acid Enhances Cell Proliferation During Eosinopoiesis Through the CD44 Surface Antigen", *J Immunol*, 154(8): 4073-4080 (1995).
Hanna, J. and Hubel, A., "Preservation of Stem Cells", *Organogenesis*, 5(3): 134-137 (2009).
Harris, D.T., et al., "Cell-Based Therapy for Epithelial Wounds", *Cytotherapy*, 14(7): 802-810 (2012).

(56) References Cited

OTHER PUBLICATIONS

Hayakawa, J., et al., "5% Dimethyl Sulfoxide (DMSO) and Pentastarch Improves Cryopreservation of Cord Blood Cells Over 10% DMSO", *Transfusion*, 50(10): 2158-2166 (2010).

Heng, B.C., "Effect of Rho-Associated Kinase (ROCK) Inhibitor Y-27632 on the Post-Thaw Viability of Cryopreserved Human Bone Marrow-Derived Mesenchymal Stem Cells", *Tissue Cell*, 41(5): 376-380 (2009).

Hoggatt, J., et al., "Prostaglandin $E_2$ Enhances Hematopoietic Stem Cell Homing, Survival, and Proliferation", *Blood*, 113(22): 5444-5455 (2009).

Huang, Y.C., et al., "Umbilical Cord Versus Bone Marrow-Derived Mesenchymal Stromal Cells", *Stem Cells and Development*, 21(15): 2900-2903 (2012).

International Search Report for International Application No. PCT/SG2013/000348, "Wound Dressing Nanomesh Impregnated with Human Umbilical Cord Wharton's Jelly Stem Cells", dated Oct. 22, 2013, consisting of 13 pages.

Iqbal, S.A., et al., "Identification of Fibrocytes From Mesenchymal Stem Cells in Keloid Tissue: A Potential Source of Abnormal Fibroblasts in Keloid Scarring", *Arch Dermatol Res*, 304(8): 665-671 (2012).

Irvine, A., et al., "Human Umbilical Cord Conditioned Medium: A Stimulus for Human CFU-G", *Exp. Hematol.* 12: 19-24 (1984).

Jackson, W.M., et al., "Concise Review: Clinical Translation of Wound Healing Therapies Based on Mesenchymal Stem Cells", *Stem Cells Translational Medicine*, 1: 44-50 (2012).

Jager, R., and Fearnhead, H, ""Dead Cells Talking": The Silent Form of Cell Death is Not So Quiet", *Biochem Res Intl*, 2012/453838, 8 pgs (2012).

Jeon, Y.K., et al., Mesenchymal Stem Cells' Interaction With Skin: Wound-Healing Effect on Fibroblast Cells and Skin Tissue:, *Wound Repair Regen*, 18(6): 655-661 (2010).

Ji R., et al., "MicroRNA Expression Signature and Antisense-Mediated Depletion Reveal an Essential Rose of MicroRNA in Vascular Neointimal Lesion Formation", *Circ Res.*, 100:1579-1588 (2007).

Jin, G., et al., "Stem Cell Differentiation to Epidermal Lineages on Electrospun Nanofibrous Substrates for Skin Tissue Engineering", *Acta Biomater*, 7(8): 3113-3122 (2011).

Jodele, S., et al., "The Contribution of Bone Marrow-Derived Cells to the Tumor Vasculature in Neuroblastoma Is Matrix Metalloproteinase-9 Dependent" *Cancer Res*, 65(8): 3200-3208 (2005).

Karahuseyinoglu, S., et al., "Biology of Stem Cells in Human Umbilical Cord Stroma: In Situ and In Vitro Surveys", *Stem Cells*, 25:319-331 (2007).

Karolina, D.S., et al., "MicroRNA 144 Impairs Insulin Signaling by Inhibiting the Expression of Insulin Receptor Substrate 1 in Type 2 Diabetes Mellitus", *Plos One*, e22839, 6(8): 19 pages (2011).

Kawachi, Y., et al., "Superficial Epithelioma With Sebaceous Differentiation: Immunohistochemical Study of Keratinocyte Differentiation Markers", *Eur J Dermatol*, 21(6): 1016-1017 (2011).

Kieran, T., et al., "Interleukin-10 Reduces Scar Formation in Both Animal and Human Cutaneous Wounds: REsults of Two Preclinical and Phase II Randomized Control Studies", *Wound Repair Regen*, 21(3): 428-436 (2013).

Kim, JY, et al., "Human Cord Blood-Derived Endothelial Progenitor Cells and Their Conditioned Media Exhibit Therapeutic Equivalence for Diabetic Would Healing," *Cell Transplantation*, vol. 19, pp. 1635-1644 (2010).

Krishnan, A. and Forman, S.J., "Hematopoietic STem Cell Transplantation for AIDS Related Malignancies", *Curr Opin Oncol*, 22(5): 456-460 (2010).

Kuo, Y.R., et al., "Bone Marrow-Derived Mesenchymal Stem Cells Enhanced Diabetic Wound Healing Through Recruitment of Tissue Regeneration in a Rat Model of Streptozotocin-Induced Diabetes", *Plas Reconstr Surg*, 128: 872-880 (2011).

Kuzuya, H., et al., "Determination of Aloenin, Barbaloin and Isobarbaloin in *Aloe* Species by Micellar Electrokinetic Chromatography", *J Chromatogr B Biomed Sci Appl*, 572: 91-97 (2001).

LaRocca, G., et al., "Isolation and Characterization of Oct-4+/HLA-G+ Mesenchymal Stem Cells From Human Umbilical Cord Matrix: Differntiation Potential and Detection of New Markers", *Histochem Cell Biol*, 131(2): 267-282 (2009).

Lemoli, R.M., et al., "Interleukin-11 Stimulates the Proliferation of Human Hematopoietic CD34+ and CD34+CD33-DR-Cells and Synergizes With Stem Cell Factor, Interleukin-3, and Granulocyte-Macrophage Colony-Stimulating Factor", *Exp Hematology*, 31: 1668-1672 (1993).

Li, F., et al., "Apoptotic Cells Activate the Phoenix Rising" Pathway to Promote Would Healing and Tissue Regeneration, *Sci Signal*, 3(110): 11 pgs (2010).

Liang, C.C., et al., "In Vitro Scratch Assay: A Convenient and Inexpensive Method for Analysis of Cell Migration In Vitro", *Nature Protocols*, 2(2): 329-333 (2007).

Liao, B., et al., "MicroRNA Cluster 302-367 Enhances Somatic Cell Reprogramming by Accelerating a Mesenchymal-to-Epithelial Transition", *J Biol Chem*, 286(19):17359-17364 (May 13, 2011).

Limaye, L.S. and Kale, V.P., "Cryopreservation of Human Hematopoietic Cells With Membrane Stabilizers and Bioantioxidants as Additives in the Conventional Freezing Medium", *J Hematother Stem Cell Res*, 10(5): 709-718 (2001).

Liu, C., et al., "A Novel PTEN Gene Promoter Mutation and Untypical Cowden Syndrome", Clin *J Cancer Res*, 25(3): 306-311 (2013).

Liu, J., et al., "Suppression of Cholangiocarcinoma Cell Growth by Human Umbilical Cord Mesenchymal Stem Cells: A Possible Rold of Wnt and Akt Signaling", *PlosOne*, 8(4): e62844, 11 pages (2013).

Liu, Y, "Increased Matrix Metalloproteinase-9 Predicts Poor Wound Healing in Diabetic Foot Ulcers", *Diab Care*, 32:117-119 (2009).

Lorenz, H.P., et al., "Scarless Wound Repair: A Human Fetal Skin Model", *Development*, 114: 253-259 (1992).

Luo, G., et al., "Promotion of Cutaneous Wound Healing by Local Application of Mesenchymal Stem Cells Derived From Human Umbilical Cord Blood", *Wound Repair Regen*, 18(5): 506-513 (2010).

Ma, K., et al., Effects of Nanofiber/Stem Cell Composite on Wound Healing in Acute Full-Thickness Skin Wounds, *Tissue Eng Part A*, 17(9-10): 1412-1424 (2011).

Ma, Y., et al., "The In Vitro and In Vivo Effects of Human Umbilical Cord Mesenchymal Stem Cells on the Growth of Breast Cancer Cells", *Breast Cancer Res Treat*, 133(2): 473-485 (2012).

Madhyastha, R., et al., "MicroRNA Signature in Diabetic Wound Healing: Promotive Role of miR-21 in Fibroblast Migration", Int Wound J, 9(4): 355-361 (2012).

Magin, A.S., et al., "Primary Cells as Feeder Cells for Coculture Expansion of Human Hematopoietic Stem Cells from Umbilical Cord Blood—A Comparative Study", *Stem Cells and Development*, 18(1): 173-185 (2009).

MaHam, A., et al., "Protein-Based Nanomedicine Platforms for Drug Delivery", *Small*, 5(15): 1706-1721 (2009).

Mannello, F., et al., "Concise Review: No Breakthroughs for Human Mesenchymal and Embryonic Stem Cell Culture: Conditioned Medium, Feeder Layer, or Feeder-Free: Medium with Fetal Calf Serum, Human Serum, or Enriched Plasma; Serum-Free, Serum Replacement Nonconditioned Medium, or Ad Hoc Formula? All That Glitters is Not Gold!", *Stem Cells*, 25: 1603-1609 (2007).

Mansilla, E., et al., "Human Mesenchymal Stem Cells ARe Tolerized by Mice and Improve Skin and Spinal Cord Injuries", *Transplant Proc*, 37(1): 292-294 (2005).

Mareschi, K., et al., "Isolation of Human Mesenchymal Stem Cell: Bone Marrow Versus Umbilical Cord Blood", *Haematologica*, 86: 1099-1100 (2001).

Martin, P., et al., "Wound Healing in the PU.1 Null Mouse-Tissue Repair Is Not Dependent on Inflammatory Cells", *Current Biology*, 13: 1122-1128 (2003).

Maurya, D.K., et al., "Therapy With Un-Engineered Naïve Rat Umbilical Cord Matrix Stem Cells Markedly Inhibits Growth of Muring Lung Adenocarcinoma", *BMC Cancer*, 10: 10 pages (2010).

Maxson, S., et al., "Concise Review: Role of Mesenchymal Stem Cells in Wound Repair", *Stem Cells Translational Medicine*, 1: 142-149 (2012).

(56) References Cited

OTHER PUBLICATIONS

Mendonca, F.A.S., et al., "Effects of the Application of Aloe Vera (1.) and Microcurrent on the Healing of Wounds Surgically Induced in Wistar Rats", *Acta Cir Brasileira*, 24(2): 150-155 (2009).
Mogili, N.S., et al., "Altered Angiogenic Balance in Keloids: A Key to Therpeutic Intervetion", *Transl Res*, 159(3): 182-189 (2012).
Moon, J.H., et al., "Isolation and Characterization of Multipotent Human Keloid-Derived Mesenchymal-Like Stem Cells", *Stem Cells Dev*, 17(4): 713-724 (2008).
Moshref, S.S. and Mufti, S.T., "Keloid and Hypertrophic Scars: Comparative Histopathological and Immunohistochemical Study", *JKAU: Med. Sci.*, 17(3): 3-22 (2010).
Muller M, et al., Matrix metalloproteinases and diabetic foot ulcers: the ratio of MMP-1 to TIMP-1 is a predictor of wound healing, *Diab Med*, 25:419-426 (2008).
Murphy, G. and Nagase, H., "Progress in Matrix Metalloproteinase Research", *Mol. Aspects Med*, 29(5): 290-308 (2008).
Musina, R.A., et al., "Umbilical Cord Blood Mesenchymal Stem Cells", *Bull Exp Biol Med*, 143(1): 127-131 (2007).
Nagaoka, T., et al., "Delayed Wound Healing in the Absence of Intracellular Adhesion Molecule-1 or L-Selectin Expression", American Journal of Pathology, 157(1): 237-247 (2000).
Nekanti, U., et al., "Lone-Term Expansion and Pluripotent Marker Array Analysis of Wharton's Jelly-Derived Mesenchymal Stem Cells", *Stem Cell Dev*, 19(1): 117-130 (2010).
Pappa, K.I. and Anagnou, N.P., "Novel Sources of Fetal Stem Cells: Where Do They Fit on the Developmental Continuum?", *Regen Med*, 4(3): 423-433 (2009).
Pastrana, E., et al., "Eyes Wide Open: A Critical Review of Sphere-Formation as an Assay for Stem Cells", *Cell Stem Cell*, 8(5): 486-498 (2011).
Pezzolesi, M.G., et al., "Mutation-Positive and Mutation-Negative Patients With Cowden and Bannayan-Riley-Ruvalcaba Syndromes Associated With Distinct 10q Haplotypes", *The American Journal of Human Genetics*, 79: 923-934 (2006).
Prasanna, S.J. and Jahnavi, V.S., "Wharton's Jelly Mesenchymal Stem Cells as Off-The-Shelf Cellular Therapeutics: A Closer Look Into Their Regenerative and Immunomodulatory Properties", *The Open Tissue Engineering and Regenerative Medicine Journal*, 4: 28-38 (2011).
Rachakatla, R.S., et al., "Development of Human Umbilical Cord Matrix Stem Cell-Based Gene Therapy for Experimental Lung Tumors", *Cancer Gene Therapy*, 14: 828-835 (2007).
Rebulla, P., "Cord Blood Banking 2002: 112,010 of 7,914,773 Chances", *Transfusion*, 42(10): 1246-1248 (2002).
Rnjak, J., et al., "Severe Burn Injuries and the Role of Elastin in the Design of Dermal Substitutes", *Tissue Eng Part B Rev*, 17(2): 81-91 (2011).
Robinson, S.N., et al., "Mesenchymal Stem Cells In Ex Vivo Cord Blood Expansion", *Best Pract Res Clin Haematol*, 24: 83-92 (2011).
Romanov, Y., et al., "Searching for Alternative Sources of Postnatal Human Mesenchymal Stem Cells: Candidate MSC-Like Cells from Umbilical Cord", *Stem Cells*, 21:105-110 (2003).
Salama, H., et al., "Autologuous Hematopoietic Stem Cell Transplantation in 48 Patients With End-Stage Chronic Liver Disease", *Cell Transplantation*, 16: 1475-1486 (2010).
Sarugaser, R., et al., "Human Umbilical Cord Perivascular (HUCPV) Cells: A Source of Mesenchymal Progenitors", *Stem Cells*, 23:220-229 (2005).
Sasaki, M., et al., "Mesenchymal Stem Cells Are Recruited Into Wounded Skin and Contribute to Wound Repair by Transdifferentiation Into Multiple Skin Cell Type", *The Journal of Immunology*, 180: 2581-2587 (2008).
Sasnoor, L.M., et al., "A Combination of Catalase and Trehalose as Additives to Conventional Freezing Medium Results in Improved Cryoprotection of Human Hematopoietic Cells With REference to In Vitro Migration and Adhesion Properties", *Transfusion*, 45(4): 622-633 (2005).
Sasnoor, L.M., et al., "Prevention of Apoptosis as a Possible Mechanism Behind Improved Cryoprotection of Hematopoietic Cells by Catalase and Trehalose", *Transplantation*, 80: 1251-1260 (2005).
Sasnoor, L.M., et al., "Supplementation of Conventional Freezing Medium With a Combination of Catalasc and Trehalose Results in Better Protection of Surface Molecules and Functionality of Hematopoietic Cells", *J Hemathother Stem Cell Res*, 12:553-564 (2003).
Schneider, R.K., et al., "Long-Term Survival and Characterisation of Human Umbilical Cord-Derived Mesenchymal Stem Cells on Dermal Equivalents", *Differentiation*, 79(3): 182-193 (2010).
Seshareddy, K., et al., "Method to Isolate Mesenchymal-Like Cells From Wharton's Jelly of Umbilical Cord", *Method Cell Biol*, 86: 101-119 (2008).
Shaw, T.J. and Martin, P., "Wound Repair at a Glance", *Journal of Cell Science*, 122(18): 3209-3213 (2009).
Shilo, S., et al., "Cutaneous Wound Healing AFter TReatment With Plant-Derived Human Recombinant Collagen Flowablc Gel", *Tiss Eng Part A*, 19(13-14): 1519-1526 (2013).
Shin, L. and Peterseon, D.A., "Human Mesenchymal Stem Cell Grafts Enhance Normal and Impaired Wound Healing by Recruiting Existing Endogenous Tissue Stem/Progenitor Cells", *Stem Cells Translational Medicine*, 2: 33-42 (2013).
Shohara, R., et al., "Mesenchymal Stromal Cells of Human Umbilical Cord Wharton's Jelly Accelerate Wound Healing by Paracrine Mechanisms," *Cytotherapy*, vol. 14, pp. 1171-1181 (2012).
Spaeth, E.L., et al., "Mesenchymal Stem Cell Transition to Tumor-Associated Fibroblasts Contributes to Fibrovascular Network Expansion and Tumor Progression", *PlosOne*, 4(4): e4992: 11 pages (2009).
Stevens, L.J. and Page-McCaw, A., "A Secreted MMP Is Required for Reepithelialization During Wound Healing", *Molecular Biology of the Cell*, 23: 1068-1079 (2012).
Stoff, A., et al., "Promotion of Incisional Wound Repair by Human Mesenchymal Stem Cell Transplantation", *Exp. Dermatol*, 18(4): 362-369 (2009).
Stroh, C., et al., "The Role of Caspases in Cryoinjury: Caspase Inhibition Strongly Improves the Recovery of Cryopreserved Hematopoietic and Other Cells", *The FASEB Journal*, 16: 1651-1653 (2002).
Suarez, Y., et al., "Dicer-dependent endothelial microRNS are necessary for postnatal angiogenesis", *PNAS*, USA, 105(37):14082-14087 (2008).
Subramanian, A., et al., "Human Umbilical Cord Wharton's Jelly Mesenchymal Stem Cells Do Not Transform to Tumor-Associated Fibroblasts in the Presence of Breast and Ovarian Cancer Cells Unlike Bone Marrow Mesenchymal Stem Cells", *J Cell Biochem*, 113(6): 1886-1895 (2012).
Sudo, K., et al., "Mesenchymal Progenitors Able to Differentiate Into Osteogenic, Chondrogenic, and/or Adipogenic Cells In Vitro Are Present in Most Primary Fibroblast-Like Cell Populations", *Stem Cells*, 25: 1610-1617 (2007).
Sullivan, S.R., et al., "Validation of a Model for the Study of Multiple Wounds in the Diabetic Mouse (db/db)", *Plast Reconstr Surg*, 113(3): 953-960 (2004).
Sun, B., et al., "Human Umbilical Cord Blood Mesenchymal Stem Cell-Derived Extracellular Matrix Prohibits Metastic Cancer Cell MDA-MB-231 Proliferation", *Cancer Lett*, 196(2): 178-185 (2010).
Szulgit, G., et al., "Alterations in Fibroblast α1β1 Integrin Collagen Receptor Expression in Keloids and Hypertrophic Scars", *Journal of Investigative Dermatology*, 118: 409-415 (2002).
Taghizadeh, R.R., et al., "Wharton's Jelly Stem Cells: Future Clinical Applications", *Placenta*, 32: S311-S315 (2011).
Takzare, N., et al., "Influence of Aloe Vera Gel on Dermal Wound Healing Process in Rat", *Toxicology Mechanisms and Methods*, 19: 73-77 (2009).
Tocco, I., et al., "Nanotechnology-Based Therapies for Skin Wound Regeneration", *Journal of Nanomaterials*, Article ID 714134: 11 Pages (2012).
Toma, J.G., et al., "Isolation and characterization of Multipotent Skin-Derived Precursors From Human Skin", *Stem Cells*, 23: 727-737 (2005).

(56) References Cited

OTHER PUBLICATIONS

Toma, J.G., et al., "Isolation of Multipotent Adult Stem Cells From the Dermis of Mammalian Skin", *Nature Cell Biology*, 3: 778-784 (2001).

Troyer, D.L. and Weiss, M.L., "Concise Review: Wharton's Jelly-Derived Cells Are a Primitive STromal Cell Population", *Stem Cells*, 26: 591-599 (2008).

Vazquez, B., et al., "Antiinflammatory Activity of Extracts From Aloe Vera Gel", *J Ethnopharmacol*, 55: 69-75 (1996).

Venugopal, P., et al., "Isolation, characterization, and gene expression analysis of Wharton's jelly-derived mesenchymal stem cells under xeno-free culture conditions", *Stem Cells and Closing: Advances and Applications*, 4: 39-50 (2011).

Walter, M.N., et al., "Mesenchymal Stem Cell-Conditioned Medium Accelerates Skin Wound Healing: An Invitro Study of Fibroblast and Keratinocyte Scratch Assays", *Exp Cell Res*, 316(7): 1271-1281 (2010).

Wang, H.S., et al., "Mesenchymal Stem Cells in the Wharton's Jelly of the Human Umbilical Cord", *Stem Cells*, 22: 1330-1337 (2004).

Wang, X.Y., et al., "Identification of Mesenchymal Stem Cells in Aorta-Gonad-Mesonephros and Yolk Sac of Human Embryos", *Blood*, 111(4): 2436-2443 (2008).

Wang, Y., et al., "A Toxicity Study of Multiple-Administration Human Umbilical Cord Mesenchymal Stem Cells in Cynomolgus Monkeys", *Stem Cells and Development*, 21(9): 14011408 (2012).

Weiss, M.L., et al., "Human Umbilical Cord Matrix Stem Cells: Preliminary Characterization and Effect of Transplantation in a Rodent Model of Parkinson's Disease", *Stem Cells*, 24: 781-792 (2006).

Weiss, M.L., et al., "Immune Properties of Human Umbilical Cord Wharton's Jelly-Derived Cells", *Stem Cells*, 26:2865-2874 (2008).

Welch, W.J., et al., "Response of Mammalian Cells to Metabolic Stress; Changes in Cell Physiology and Structure/Function of Stress Proteins", *Curr Top Microbiol Immunol*, 167: 31-55 (1991).

Weis, J., et al., "Migratory Neighbors and Distant Invaders: Tumor-Associated Niche Cells", *Genes & Development*, 22:559-574 (2008).

Wexler, S.A., et al., "Adult Bone Marrow Is a Rich Source of Human Mesenchymal Stem Cells but Umbilical Cord and Mobilized Adult Blood Are Not", *British Journal of Haematology*, 121: 368-374 (2003).

White-Chu, E.F., et al., "Pressure Ulcers in Long-Term Care", *Clin Geriatr Med*, 17(2): 241-258 (2011).

Wu, S., et al., "Microvesicles Derived From Human Umbilical Cord Wharton's Jelly Mesenchymal Stem Cells Attenuate Bladder Tumor Cell Growth In Vitro and In Vivo", *PlosOne*, 8(4): e61366: 12 pages (2013).

Wu, Y., et al., "Mesenchymal Stem Cells Enhance Would Healing Through Differentiation and Angiogenesis", *Stem Cells*, 25:2648-2659 (2007).

Yang, F., et al., "Genetic Engineering of Human Stem Cells for Enhanced Angiogenesis Using Biodegradable Polymeric Nanoparticles", *PNAS*, 107(8): 3317-3322 (2010).

Yew, T.L., et al., "Enhancement of Wound Healing by Human Multipotent Stromal Cell Conditioned Medium: The Paracrine Factors and p38 MAPK Activation", *Cell Transplantation*, 20: 693-706 (2011).

Yukami, T., et al., "Endothelial Selectins Regulate Skin Wound Healing in Cooperation With L-Selectin and ICAM-1", *Journal of Leukocyte Biology*, 82:519-531 (2007).

Zhang, K, et al., "Increased Types I and III Collagen and Transforming Growth Factor-$\beta$1 mRNA and Protein in Hypertrophic Burn Scar" *J Invest Dermatol*, 104:750-754 (1995).

Zhang, Q., et al., "Tumor-Like Stem Cells Derived From Human Keloid Are Governed by the Inflammatory Niche Driven by IL-17/IL-6 Axis", *PlosOne*, 4(11): c7798: 16 pages (2009).

Zhang, Y., et al., "Co-Culture of Umbilical Cord Blood CD34+ Cells With Human Mesenchymal Stem Cells", Tissue Engineering, 12(8): 2161-2170 (2006).

Zhang, Y.Z., et al., "Biomimetic and Bioactive Nanofibruous Scaffolds From Electrospun Composite Nanofibers", *International Journal of Nanomedicine*, 2(4): 623-638 (2007).

Notice of Allowance for U.S. Appl. No. 13/667,370, entitled "Wharton's Jelly Mesenchymal Stem Cells and Uses Thereof"; dated Dec. 15, 2015.

\* cited by examiner

15A Adherent culture

15B Sphere culture

15C

15D

Scratch-wound assay

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 1
gcaccgtcaa ggctgagaac                                              20

<210> SEQ ID NO 2
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 2
ggatctcgct cctggaagat g                                            21

<210> SEQ ID NO 3
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 3
cacagaggtt tcagtggttt gg                                           22

<210> SEQ ID NO 4
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 4
gcaccagtag caccatcatt tc                                           22

<210> SEQ ID NO 5
<211> LENGTH: 22
<212> TYPE: DNA
<213> ORGANISM: Artificial Sequence
```

<220> FEATURE:
<223> OTHER INFORMATION: oligonucleotide primer

<400> SEQUENCE: 5
ctgaaattct gccatcctga ac						22

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 6
ggattgccgt agctaaactg aa						22

<210> SEQ ID NO 7
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 7
aagattggag agaagtggga cc						22

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
ggagcaaatg gcaccgagat a							21

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 9
ctgaaattct gccatcctga ac						22

<210> SEQ ID NO 10
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 10
ggattgccgt agctaaactg aa						22

<210> SEQ ID NO 11
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 11
aagattggag agaagtggga cc						22

```
<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
gagcaaatgg caccgagata                                             20

<210> SEQ ID NO 13
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 13
ttgagaaagc cttccaactc tg                                          22

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 14
ccgcaacacg atgtaagttg ta                                          22

<210> SEQ ID NO 15
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 15
gcaccgtcaa ggctgagaac                                             20

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 16
ggatctcgct cctggaagat g                                           21
```

WOUND DRESSING NANOMESH IMPREGNATED WITH HUMAN UMBILICAL CORD WHARTON'S JELLY STEM CELLS

RELATED APPLICATION

This application is a U.S. National Stage of International Application No. PCT/SG2013/000348, filed on Aug. 15, 2013, published in English, which claims the benefit of U.S. Provisional Application No. 61/683,391, filed on Aug. 15, 2012. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 44591049002SEQUENCELISTING.TXT; created Jul. 20, 2015, 4 KB in size.

BACKGROUND OF THE INVENTION

Non-healing wounds are a chronic problem in patients suffering from diabetes, kidney failure, burns and bed sores. Diabetic wounds lead to foot ulcers which eventually end up in lower limb amputations and some individuals are prone to abnormal wound healing leading to ugly scars called keloids which are a cosmetic nuisance and psychosocial burden. Current methods to accelerate wound healing have met with limited success and keloids when treated recur frequently. Keloids behave like benign tumors making them even more challenging to treat. In the US alone, an estimated US$25 billion is spent annually on treatment of chronic wounds and the problem is growing worldwide due to an aging population and rise in the incidence of diabetes and obesity.

SUMMARY OF THE INVENTION

Shown herein is the use of stem cells from the human umbilical cord Wharton's jelly (hWJSC) that possess certain unique properties that can be used to heal wounds and suppress scars (e.g., keloid suppression). Also shown herein is the ability of WJSCs/extracts to (1) destroy tumorigenic cells and (2) promote cell proliferation which provides for a medical dressing (e.g., a wound dressing patch) comprising WJSCs/extracts (e.g., an aloe vera-nanofibrous mesh impregnated with the WJSCs/extracts) which are applied to wounds to deliver specific molecules resulting in suppression of scar formation (e.g., keloid formation) and/or wound healing.

Accordingly, in one aspect, the invention is directed to a method of treating a wound in an individual in need thereof comprising contacting the wound with an effective amount of a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof.

In another aspect, the invention is directed to a method of treating a wound to suppress scar formation in an individual in need thereof comprising contacting the wound with an effective amount of a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof.

In yet another aspect, the invention is directed to a medical dressing comprising Wharton's jelly stem cells (WJSCs), a cell culture medium that has been conditioned with WJSCs, a lysate of WJSCs, a cell culture medium that has been conditioned with WJSCs exposed to apoptotic skin cells and keloid cells, or a combination thereof.

In other aspects, the invention is directed pharmaceutical compositions comprising the medical dressing described herein.

Wharton's jelly stem cells and extracts thereof have several advantages over other stem cell sources and are an attractive stem cell for varied cell based therapies. Additionally, hWJSCs release hyaluronic acid (HA) and glycosaminoglycans (GAGs) in large quantities and these are the essential building blocks for tissue repair.

BRIEF DESCRIPTION OF THE DRAWINGS

FIGS. 13A-13D: (13A) Digitized images of diabetic wounds in db/db mice showed complete wound closure in the GFP-hWJSCs+AV/PCL and hWJSC-CM+AV/PCL treatment arms compared to controls by day 28. (13B) On day 7, the mean±SEM percentage wound closure rates of the GFP-hWJSCs+AV/PCL treatment arm of diabetic wounds was significantly greater than the controls while on day 14 that of the hWJSC-CM+AV/PCL treatment group was significantly greater than the controls (p<0.05). (13C) On day 7, histological examination of diabetic wound biopsies showed reepithelialization, sebaceous glands and hair follicles in the GFP-hWJSCs+AV/PCL and hWJSC-CM+AV/PCL treatment groups compared to controls. On days 14 and 28 the same treatment groups showed the formation of stratified squamous epithelium, increased cellularity and vasculature and increased sebaceous gland and hair follicle numbers compared to controls. On day 28 the diabetic wounds of controls not receiving any treatment had no stratified squamous epithelium, only a few sebaceous glands and hair follicles and did not display the typical normal skin phenotype. D: dermis; E: epidermis; HF: hair follicle; SG: sebaceous gland; S: stroma; SSE: stratified squamous epithelium. Scale bar: 100 µm. (13D) a, d: Positive staining for human cytokeratin was present on days 14 and 28 in diabetic wounds while human involucrin was evident on day 14 and human filaggrin was present on day 28. Long arrows: Viable GFP-hWJSCs in diabetic wound biopsies. Short arrows: Positive human keratinocyte markers (cytokeratin, involucrin and filaggrin).

DETAILED DESCRIPTION OF THE INVENTION

Figure 1:
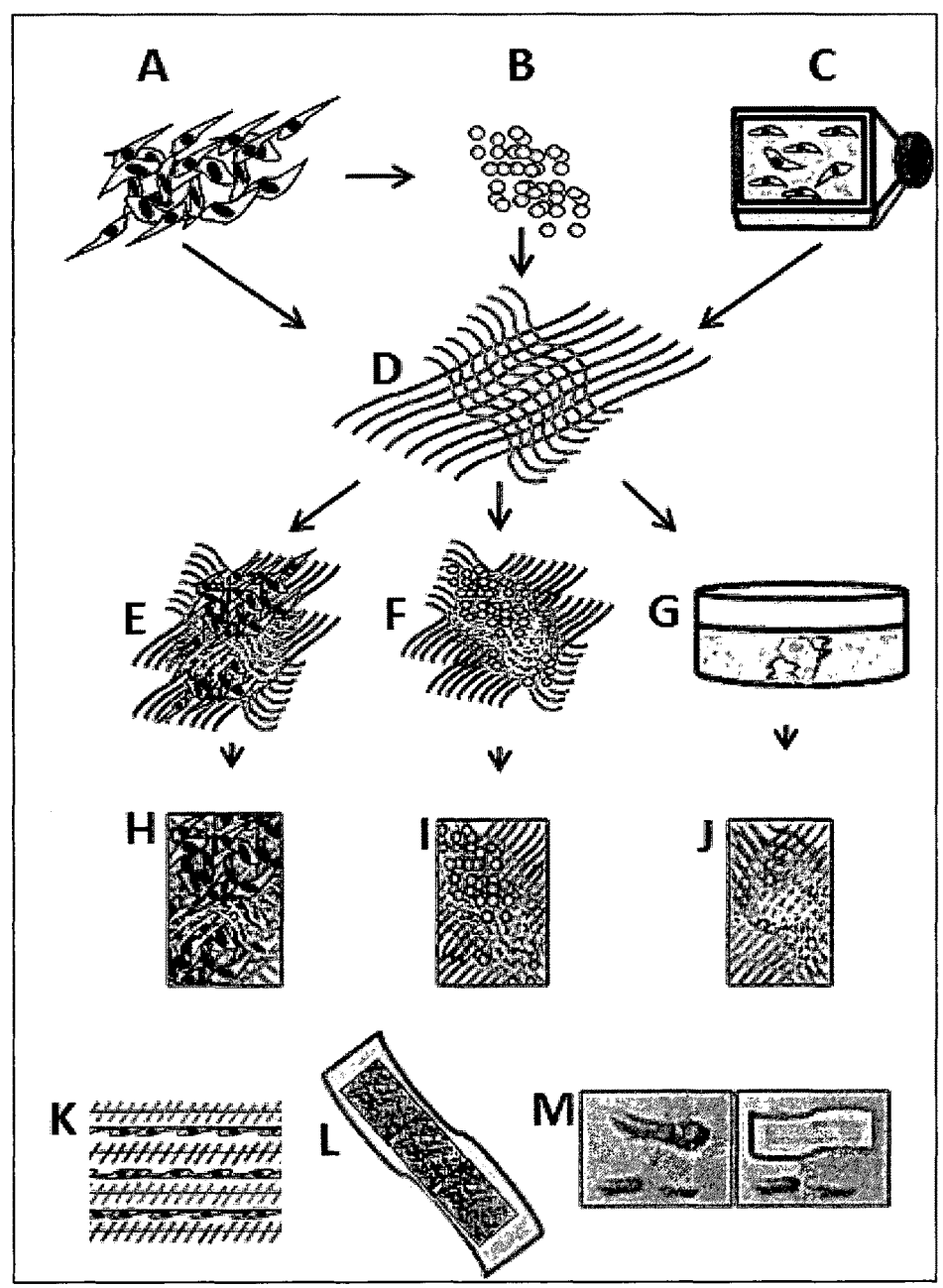
FIG. 1 shows a diagrammatic representation of a wound dressing patch for keloid/wound healing. A: hWJSCs; B: hWJSC-extract; C: hWJSC-PCM; D: Aloe vera-nanofibrous mesh; E: Aloe vera-nanofibrous mesh impregnated with hWJSCs; F: Aloe vera-nanofibrous mesh impregnated with hWJSC-extract; G: Aloe vera-nanofibrous mesh impregnated with hWJSC-PCM; H, I, J: Final wound dressing patches; K: Cross section of wound dressing patch showing alternating layers of aloe vera-nanofibres and hWJSCs; L: Wound dressing patch; M: Application of the wound dressing patch on a keloid.

Described herein are compositions and methods that allow for the suppression of scar formation (e.g., keloid formation) such as in individuals prone to this condition and the encouragement of wound healing (e.g., in diabetic and non-diabetic individuals).

Accordingly, in one aspect, the invention is directed to a method of treating a wound in an individual in need thereof comprising contacting the wound with an effective amount of a composition comprising (consisting essentially of, consisting of) (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof.

Any number of wounds can be treated using the methods described herein. Examples of wounds include a surgical incision, a non-healing wound from a disease or condition (e.g., a diabetic wound (ulcer), a wound due to kidney dysfunction or failure; venous and arterial ulcers), a traumatic injury wound, an ulcer, a burn, a bed sore, an excised keloid wound. In a particular aspect, the wound being treated is at risk of becoming a scar or a keloid. In another aspect, the wound being treated is a diabetic wound.

In another aspect, the invention is directed to a method of treating and/or inhibiting a scar and/or excessive scar formation and/or growth. In a particular aspect, the invention is directed a method of treating a wound to suppress scar formation in an individual in need thereof comprising contacting the wound with an effective amount of a composition comprising (consisting essentially of, consisting of) (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof. In a particular aspect, the scar is an abnormal scar such as a keloid or hypertrophic scar (excessive scar growth).

As described in further detail herein, the wound is maintained under conditions in which wound healing is encouraged (e.g., enhanced) and/or scar formation is suppressed (e.g., partially; completely).

In yet another aspect, the invention is directed to a composition comprising a medical dressing comprising (consisting essentially of, consisting of) (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or a combination thereof.

In the methods and compositions described herein, the wound and/or scar is contacted with a composition comprising (consisting essentially of, consisting of) Wharton's jelly stem cells (WJSCs) and/or extracts thereof. As used herein, "Wharton's jelly" refers to a mucilaginous jelly-like substance that occurs in the umbilical cord. Large numbers of bona fide, fully characterized mesenchymal stem cells (MSCs) with high proliferation rates and low population doubling times have been reported in the human umbilical cord Wharton's Jelly (referred to herein as "WJSCs", and in particular embodiments, human WJSCs ("hWJSCs") by several workers. In some aspects, it has been shown that about $4.6 \times 10^6$ fresh live hWJSCs can be harvested from about 1 cm of umbilical cord and the stemness properties of these hWJSCs lasted longer than bone marrow MSCs in vitro (10 vs 3 passages). hWJSCs were also shown to be hypoimmunogenic, thus allowing their use in both autologous and allogeneic settings without the concerns of graft versus host disease, and thaw survival rates of hWJSCs after cryopreservation were greater than 90%.

A variety of methods can be used to obtain WJSCs from umbilical cord (e.g., Weiss et al., *Stem Cells,* 24:781-792 (2006), Fong et al., *Reprod Biomed Online,* 15:708-718 (2007), Fong et al., *Reprod Biomed Online,* 21:391-401 (2010), Wang et al., *Stem Cells,* 22:1330-1337 (2004), Romanov et al., *Stem Cells,* 21:105-110 (2003), Sarugaser et al., *Stem Cells,* 23:220-229 (2005), Karahuseyinoglu et al., *Stem Cells,* 25:319-331 (2007), all of which are incorporated herein by reference). For example, as exemplified herein WJSCs can be obtained from one or more pieces of umbilical cord that have been slit open and inverted onto a Petri dish containing an enzymatic solution and incubated at about 37° C. in about 5% $CO_2$ in air atmosphere for about 45 minutes to allow loosening and separation of the Wharton's jelly from the umbilical cord. The separated Wharton's jelly can then be syringed through a needle (e.g., an 18G needle; a 21G needle) to further break up, and release the WJSCs from, the Wharton's jelly. Alternatively, the pure mucilaginous Wharton's jelly itself can be frozen immediately after isolation, thawed and healthy hWJSCs recovered from the thawed Wharton's jelly which can be grown in culture and propagated.

The WJSCs for use in the methods can be obtained from a single donor or multiple donors. In addition, the WJSCs used in the methods described herein can be freshly isolated, frozen (e.g., cryopreserved), or a combination thereof.

Typically, the WJSCs are of mammalian origin. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). Examples of mammals include primates (e.g., human, monkeys, chimpanzees), rodents (e.g., rats, mice, guinea pigs), canines, felines, and ruminants (e.g., cows, pigs, horses). In a particular aspect, the WJSCs are human WJSCs (hWJSCs).

The WJSCs for use in the methods provided herein can be isolated, pure, or substantially pure. As used herein, "isolated" (e.g., isolated WJSCs) refers to substantially isolated with respect to the complex (e.g., cellular) milieu in which it occurs such as isolated from an organ, body, tissue, blood, or culture medium. In some instances, the isolated material will form part of a composition (for example, a crude extract containing other substances), buffer system, culture system or reagent mix. In other circumstances, the material can be purified to essential homogeneity. For example, an isolated composition of WJSCs can comprise at least about 50%, at least about 55%, at least about 60%, at least about 65%, at least about 70%, at least about 75%, at least about 80%, at least about 85%, at least about 90%, at least about 95%, or at least about 99% (on a total cell number basis) of all cells present.

The methods and compositions described herein can also comprise an extract of WJSCs. As used herein, an extract of WJSCs include a composition that has been contacted (e.g., cultured) with WJSCs such as a lysate of WJSCs, a cell culture medium (e.g., a WJSCs conditioned medium) and the like. In one aspect, the wound and/or scar is contacted with a lysate of WJSCs. In another aspect, the wound and/or scar is contacted with a lysate of WJSCs and WJSCs. A lysate of WJSCs, also referred to herein as a WJSC lysate(s), refers to the contents of a (one or more) lysed WJSC. As known in the art, lysed cells (e.g., lysed WJSCs) refer to cells that have had their membranes disintegrated or ruptured causing the release of the cells' contents, which is referred to as a cell lysate. A variety of methods can be used to lyse cells (e.g., by viral, enzymic, and/or osmotic mechanisms). For example, as shown herein, the cells are lysed by contacting the cells with a lysis buffer.

In the methods and compositions described herein, the wound and/or scar can also be contacted with a cell culture medium that has been conditioned with WJSCs. A cell culture medium that has been conditioned with WJSCs, referred to herein as WJSC-conditioned medium (WJSCs-CM (e.g., hWJSC-CM), is a cell culture media containing biologically active components obtained from the WJSCs that are or were cultured (e.g., grown) in the medium and have released into the media substances affecting certain cell functions (e.g., growth, lysis). The WJSC-CM can, but typically does not, contain the WJSCs that were previously cultured in the medium. The WJSCs can be cultured in culture media for one or more passages (e.g., about 1, 2, 3, 4, 5, 6, 7, 8, 9, 10, 11, 12, 13, 14, 15, 16, 17, 18, 19, 20 or more passages), and the WJSCs can be passaged after reaching about 20%, 30%, 40%, 50%, 60%, 70%, 80%, 90% or 100% confluency. In addition, in aspects in which the WJSC-CM does not contain WJSCs, the WJSCs can be removed after minutes (e.g., about 5, 10, 15, 20, 25, 30, 35, 40, 45, 50, 55 minutes), hours (e.g., about 1, 2, 3, 4, 5, 6, 7, 8, 9, 10, 15, 20, 25 hours), days (e.g., about 1, 2, 3, 4, 5, 6, 7 days), weeks (e.g., about 1, 2, 3, 4 weeks), months (e.g., 1, 2, 3, 4, 5, 6, 7, 8, 9, 10, 11, 12 months), or years (e.g., about 1, 2, 3, 4, 5 years) from culture. In addition, as described herein, depending upon the indication for which it is being used, the WJSC-CM can be further manipulated e.g., filtered, sterilized (e.g., filter sterilization), adjusted for pH and/or osmolality, diluted, concentrated, lyophilized, freeze dried etc.

As is known in the art, a medium or cell culture medium is a preparation made specifically for the growth, storage, or transport of cells. The variety of media that exist allow for the culturing of cells in general (e.g., basal medium) or specific cell types (e.g., differential media, selective media, test media, and defined media). The medium can be in a liquid or solid form. In one aspect, solid medium is a liquid medium that has been solidified with an agent such as AGAR or GELATIN.

In the methods and compositions described herein, the wound and/or scar can also be contacted with a cell culture medium that has been conditioned with WJSCs exposed to apoptotic skin cells and/or keloid cells, referred to herein as "WJSC-primed conditioned medium (WJSC-PCM). As described herein, primed conditioned medium was prepared by exposing hWJSCs to normoxic (e.g., about 5% $O_2$) or specific hypoxic (e.g., low oxygen such as less than about 5% including about 4%, 3%, 2%, 1%, 0.5% or less oxygen) and/or apoptotic culture medium environments (e.g., wound environments) before collecting the conditioned medium.

As used herein, apoptotic cells are cells that are undergoing or have undergone apoptosis, a form of programmed cell death, and have a DNA content less than 2n ("sub-G1 cells"). Such cells are usually the result of apoptotic DNA fragmentation, wherein during apoptosis, the DNA is degraded by cellular endonucleases. Therefore, nuclei of apoptotic cells contain less DNA than nuclei of healthy G0/G1 cells.

For example, a medium (e.g., a medium containing DMEM high glucose supplemented with knockout serum replacement (KOSR) medium, L-glutamine and/or antibiotic/antimycotic mixture) can be exposed to WJSCs, dying/living apoptotic primary skin (e.g., commercial foreskin fibroblasts (ATCC, Maryland USA)) and/or keloid (e.g., obtained from patients undergoing surgery to remove keloids after receiving informed consent and IRB approval) cultures in different oxygen environments (e.g., less than or equal to about 5%) and the conditioned medium separated from the WJSCs (e.g., after about 24-72 hours). The purpose was to take advantage of any useful ingredients released by the skin and keloid cells.

As will be appreciated by those of skill in the art, various concentrations of conditioned medium and/or primed conditioned medium can be used in the methods. For example, in the methods described herein, about 40%, 50%, 60%, 70%, 80%, 90% or 100% volume/volume (v/v) conditioned medium diluted in, for example, other media, can be used.

As will also be appreciated by those of skill in the art, the WJSCs, apoptotic skin cells and/or keloid cells can be maintained in media and under a variety of conditions in order to prepare the WJSC-CM and/or WJSCS-PCM. For example, the conditions can comprise maintaining the culture at about 37° C. in about 5% $CO_2$. Further, the WJSCs, apoptotic skin cells and/or keloid cells can be cultured for a number of hours or days. In some aspect, the WJSCs, apoptotic skin cells and/or keloid cells are cultured for about 1 hour, 5 hours, 10 hours, 15 hours, 20 hours, 24 hours, 2 days, 3 days, 4 days, 5 days, 6 days, 7 days, 8 days, 9 days, 10 days 11 days, 12 days, 14 days, etc.

The WJSCs, apoptotic skin cells and/or keloid cells for use in the compositions and methods provided herein can be obtained from different individuals (e.g., syngeneic, xenogeneic), different individuals of the same species (e.g., allogeneic), or from the same individual (e.g., autologous).

As shown herein, the (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof can be implanted, "seeded" or "impregnated" into an artificial structure capable of supporting three-dimensional tissue formation. These structures, typically called extracellular matrices or scaffolds, are used, for example, to recapitulate the in vivo milieu and allow cells to influence their own microenvironments. Scaffolds can serve one or more purposes such as allowing cell attachment and migration, delivering and retaining cells and biochemical factors, enabling diffusion of vital cell nutrients and expressed products, and/or exerting certain mechanical and biological influences to modify the behavior of the cell phase.

As will be appreciated by those of skill in the art, a variety of methods for impregnating the scaffold with the composition can be used. For example, the composition can be injected into the scaffold e.g., either before or after the scaffold is contacted with the wound. If the scaffold is impregnated with the composition before contact with the wound, the scaffold comprising the composition can be maintained under conditions in which the composition is allowed to recapitulate the in vivo milieu and allow cells to influence their own microenvironments. As will be appreciated by those of skill in the art, such scaffolds can be stored (e.g., frozen) until needed.

Thus, in certain aspects, the wound can be contacted with a composition comprising (consisting essentially of, consisting of) (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof, wherein the composition further comprises a scaffold. In one aspect, the wound is contacted with a scaffold comprising the composition. In other aspects, the wound can be first contacted with the scaffold and then the composition can be added to the scaffold that is already present in the wound. The composition can be added to a scaffold present in a wound either immediately after the scaffold has been contacted with the wound or after a period of time has elapsed (e.g., the composition can be introduced into the scaffold minutes, hours, days, or weeks after the scaffold has been contacted with the wound).

The scaffolds for use in the compositions and methods can have a number of features which make it suitable for use in wound healing. An example of such features includes a pore size that facilitates cell seeding and diffusion throughout the whole structure of both cells and nutrients. Another feature is biodegradability e.g., wherein the scaffold is absorbed by the surrounding tissues without the necessity of a surgical removal). In certain aspects, the rate at which degradation occurs coincides as much as possible with the rate of tissue formation: this means that while cells are fabricating their own natural matrix structure around themselves, the scaffold is able to provide structural integrity within the body and eventually break down leaving the neotissue, newly formed tissue, which will take over the mechanical load. Alternatively, it may be desirable to have a scaffold that is permanent. Other useful features of a scaffold include non-immunogenicity, transparency, nano-scale fibers, low concentration, resorption rates, etc.

As described herein, in particular aspects, a nanofibrous scaffold is used. A variety of nanofibrous scaffolds can be used. In one aspect, the scaffold has a pore size of about 0.5 µm to about 10 µm. In other aspects, the nanofibrous scaffold has a fiber diameter of about 250 nm to about 650 nm, and a fiber thickness of about 250 nm to about 650 nm.

A variety of materials (e.g., natural, synthetic, biodegradable, permanent and combinations thereof) can be used to form the scaffold. Examples of natural materials include proteic materials, such as collagen or fibrin, and polysaccharidic materials, like chitosan or glycosaminoglycans (GAGs). Among GAGs, hyaluronic acid e.g., in combination with cross linking agents (e.g. glutaraldehyde, water soluble carbodiimide, etc . . . ), can be used as scaffold material. Functionalized groups of scaffolds may be useful in the delivery of small molecules (drugs) to specific tissues. Another form of scaffold includes decellularised tissue extracts whereby the remaining cellular remnants/extracellular matrices act as the scaffold.

Commonly used synthetic materials include polycaprolactone (PCL), polylactic acid (PLA), and poly (L-lactic acid-co-e-caprolactone) which degrade within the human body to form lactic acid, a naturally occurring chemical which is easily removed from the body.

A number of different methods have been described in literature for preparing porous structures to be employed as tissue engineering scaffolds. Examples of such methods include nanofiber self-assembly to produce hydrogel scaffolds; textile technologies; fiber bonding; solvent casting and particulate leaching (SCPL) for the preparation of porous structures with regular porosity, but limited thickness; gas foaming which uses gas as a porogen; emulsification/freeze-drying techniques which do not require the use of a solid porogen; thermally induced phase separation (TIPS) which involves the use of a solvent with a low melting point; and CAD/CAM technologies using computer assisted design and manufacturing techniques.

In a particular aspect, electrospinning is used to prepare a scaffold (e.g., a nanofibrous scaffold). Electrospinning is a highly versatile technique that can be used to produce continuous fibers from submicron to nanometer diameters with a high surface area (e.g., Zhang et al., *Int J Nanomed*, 2(4):623-638 (2007)). Typically, electrospinning involves the use of a solution fed through a spinneret and application of a high voltage to the tip. The buildup of electrostatic repulsion within the charged solution causes it to eject a thin fibrous stream. A mounted collector plate or rod with an opposite or grounded charge draws in the continuous fibers, which form a highly porous network. Advantages of this technique include its simplicity and ease of variation. At a laboratory level, a typical electrospinning set-up only requires a high voltage power supply (up to 30 kV), a syringe, a flat tip needle and a conducting collector. By modifying variables such as the distance to collector, magnitude of applied voltage, or solution flow rate the overall scaffold architecture can be varied.

As will be appreciated by those of skill in the art, a variety of additional components can be added to the scaffold. For example, one or more cosmetic ingredients can be used. In a particular aspect, aloe vera is combined with a nanofibrous scaffold to mechanically hold cells and encourage the release of their products into the micro-environment. In yet another aspect, aloe vera and PCL are used to generate a nanofibrous scaffold. In certain aspects, the ratio of PCL to aloe vera in the nanofibrous scaffold is about 10:5. Aloe vera and PCL in the scaffold are both biodegradable.

As will also be appreciated by those of skill in the art, the composition can include other components that aid in wound healing. For example, the composition can further comprise one or more antibiotics, silver, fibrin or combinations thereof.

The amount of time the wound can be contacted with a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof will vary depending on a number of factors which include the type of wound, the condition of the individual, etc. Thus, the amount of time can vary from minutes, hours, days, weeks, months and years. In certain aspects, the wound is contacted with the composition for about 24 hours to about 21 days.

In other aspects, the invention is directed pharmaceutical compositions comprising the medical dressing described herein. The pharmaceutical compositions for use in the methods described herein can be formulated with a physiologically acceptable carrier or excipient to prepare a pharmaceutical composition. The carrier and composition can be sterile. The formulation should suit the mode of administration.

Methods of introduction of these compositions include, but are not limited to, intradermal, intramuscular, intraperitoneal, intraocular, intravenous, subcutaneous, topical, oral and intranasal administration. The administration can occur locally, such as at the site (e.g., margin(s)) of the wound and/or systemically. The pharmaceutical compositions of this invention can also be administered as part of a combinatorial therapy with other compounds.

As shown herein, the compositions and methods can be used to treat a wound or a scar (e.g., a keloid). As used herein, "treat" and "treatment" refer to either healing the wound or scar. In one aspect, the wound or scar is healed completely. In other aspects, the wound or scar is healed partially, e.g., the wound heals but with lessened or minimal scarring; the amount of scarring is lessened or reduced.

In addition, in the methods described herein, the wound is contacted with an effective amount (a therapeutically effective amount) of the composition (i.e., an amount that is sufficient to treat the wound or scar, such as by ameliorating symptoms associated with the wound or scar, and/or also lessening the severity of the wound or scar). The amount that will be therapeutically effective in the treatment of a particular individual's wound or scar and will depend on the symptoms and severity of the wound or scar, and can be determined by standard clinical techniques. The precise dose to be employed in the formulation will also depend on the route of administration, and the seriousness of the wound or scar, and should be decided according to the judgment of a practitioner and each individual's circumstances. Effective doses may be extrapolated from dose-response curves derived from in vitro or animal model test systems.

For example, as described herein, for hWJSCs about 0.5 to $10 \times 10^6$ cells/100 l were used; for hWJSC-CM and hWJSC-PCM about 50-200 l at concentrations of about 50-100% w/v and conditioned for about 24-72 hours were used; for hWJSC-CL about 50-200 µl at about 10-50 µg/ml protein were used.

The compositions and methods described herein can be used for a variety of individuals. In a particular aspect, the individual is a mammal. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). Examples of mammals include primates (e.g., human, monkeys, chimpanzees), rodents (e.g., rats, mice, guinea pigs), canines, felines, and ruminants (e.g., cows, pigs, horses). In a particular aspect, the individual is a human. In other aspects, the individual is a canine (e.g., dog), feline (e.g., cat), a bovine (e.g., a caw), an equine (e.g., a horse) and the like.

Thus, the compositions and methods described herein can be used for individuals in hospitals going through any form of surgery which includes a surgical incision (e.g., to encourage wound healing and suppress any keloid formation) or for individuals undergoing trauma. Additionally, the compositions and methods described herein can be used for individuals who suffer from slow-healing diabetic and non-diabetic wounds; patients prone to keloid formation after accidents/surgery, individuals who are immobile on bed suffering from bed-sores; burn victims; and trauma victims. The compositions and methods could also be used for individuals going through cosmetic surgery to prevent keloid formation and in the animal care (veterinary) industry.

The invention is also directed to use of an effective amount of a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof for treating (the treatment of) a wound in an individual in need thereof. In another aspect, the invention is also directed to use of an effective amount of a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof for the manufacture of a medicament for treating (the treatment of) a wound in an individual in need thereof.

In another aspect, the invention is directed to use of an effective amount of a composition comprising (i) Wharton's jelly stem cells (WJSCs), (ii) a cell culture medium that has been conditioned with WJSCs, (iii) a lysate of WJSCs, (iv) a cell culture medium that has been conditioned with WJSCs exposed to apoptotic skin cells and keloid cells, or (v) a combination thereof for the manufacture of a medicament for treating (the treatment of) a wound to suppress scar formation in an individual in need thereof.

EXEMPLIFICATION

Example 1

Methods/Materials
Experimental Designs

Two dimensional (human Wharton's jelly stem cells (hWJSCs), hWJSC-conditioned medium (hWJSCs-CM), hWJSC-primed conditioned medium (hWJSCs-PCM) or hWJSC-cell lysate (hWJSCs-CL) with no aloe vera nanomesh and three dimensional (hWJSCs, hWJSC-CM, hWJSC-PCM, or hWJSC-CL with aloe vera nanomesh) studies were carried out in vitro and in vivo in animal models. For the in vitro studies, linear scratches were made on skin fibroblast monolayers grown in Petri dishes to mimic wounds (conventional scratch assay (Linag et al., *Nature Protocols*, 2:329-333 (2007)). Morphological changes, proliferation rates, collagen, elastin and genomic assays were carried out on the scratched monolayers exposed to hWJSCs, hWJSC-CM, hWJSC-PCM, or hWJSC-CL with or without the aloe vera nanomesh. For the animal studies, straight and circular wounds were created on the dorsal skin in immunodeficient (Animal Resource Centre, Australia) and diabetic mice (Jackson Laboratories, USA). The wounds in the animals were exposed (by injection at several sites in the wound) separately to hWJSCs/hWJSC-CM/hWJSC-PCM/hWJSC-CL with/without the aloe vera nanomesh (hWJSCs: about 0.5 to $10 \times 10^6$ cells/100 µl; hWJSC-CM and hWJSC-PCM: 50-200 µl at concentrations of about 50-100% w/v and conditioned for about 24-72 hours; hWJSC-CL: 50-200 µl at about 10-50 µg/ml protein). Healing rates (time for wound closure) were measured together with histopathological and immunohistochemistry examination of wound biopsies to get more detailed information on wound healing and closure. There were two sets of controls for all in vitro and in vivo animal experiments. (Control 1: Untreated wounds; Control 2: Wounds treated the same way as the experimental arms but with skin fibroblasts and the skin fibroblasts' conditioned medium (CM), primed conditioned medium (PCM) or cell lysate (CL).

Isolation of Pure Human Wharton's Jelly from Umbilical Cords and its Storage

Pieces of human umbilical cord (1.5 cm) were slit open with sterile scissors and the inner surface exposed to a cocktail of enzymes (collagenase type 1, collagenase type 4, hyaluronidase) for 45 mins at 37° C. in a 5% $CO_2$ in air atmosphere. The cord pieces were then washed in Dulbecco's modified Eagle's medium (DMEM) high glucose medium to get rid of all traces of enzymes and then placed in a 60 mm sterile Petri dish containing 5 ml of fresh DMEM high glucose medium. The blunt back surface of a pair of watchmaker forceps was used to gently scrape off the gelatinous Wharton's jelly from the inner surface of each cord piece into the medium. After removal of Wharton's jelly, the remaining cord pieces were discarded and the gelatinous Wharton's jelly in medium was transferred to a 15 ml Falcon tube. The gelatinous Wharton's jelly was then syringed through a 21 gauge needle attached to a 10 ml syringe to break up the jelly and release the hWJSCs. The cell suspension was centrifuged at 300×g for 5 mins and supernatant (cell-free Wharton's jelly) collected. This jelly can be used fresh to impregnate the nano-aloe vera mesh or frozen at −80° C. for future use. For example, gelatinous masses of Wharton's jelly could be frozen and after thawing, the hWJSCs from the Wharton's jelly can be separated and grown in culture.

Preparation of hWJSCs, hWJSC-Conditioned Medium (CM), hWJSC Lysate and hWJSC Primed Conditioned Medium (PCM)

Human Wharton's jelly stem cells. (hWJSCs) were derived and propagated from discarded umbilical cords according to the method of Fong et al., *Reprod Biomed* 15:708-718 (2007); Fong et al., *Reprod Biomed* 21:391-401 (2010), both of which are incorporated herein by reference).

hWJSC-conditioned medium (CM) (extracts) was prepared by first growing the hWJSCs in a complex culture medium comprised of 80% DMEM high glucose supplemented with 20% fetal bovine serum (FBS), 1% non-essential amino acids, 2 mM L-glutamine, 0.1 mM β-mercaptoethanol, 1% insulin-transferrin-selenium (ITS), antibiotic/antimycotic mixture (Invitrogen) and 16 ng/ml basic fibroblast growth factor (FGF) (Millipore Bioscience Research Agents, Temecula, Calif.). When the hWJSC monolayer reached 80% confluency, the culture medium was replaced with a simple medium comprised of DMEM high glucose supplemented with L-glutamine and antibiotic/ antimycotic solution with/without knockout serum replacement medium (KOSR). After about 24 hours, 48 hours or 72 hours this simple medium was separated, filtered and referred to as hWJSC-CM.

Separately hWJSC lysates were prepared from early passages of hWJSCs (P3-P7) grown to 80% confluence, using a mammalian cell extraction kit (BioVision, Mountain View, Calif.) that contained protease inhibitor cocktail and dithiothreitol. Briefly, the cultured cells were washed once with phosphate buffered saline that contained no calcium and magnesium, i.e. PBS (−), dissociated with TrypLETM express and centrifuged at 500 g×5 min to obtain a cell pellet. The pellet was resuspended in 100 µl of the cell lysis buffer and pipetted up and down several times and then incubated on ice for 15 min. The contents were then centrifuged at 12000 g×5 min (Eppendorf, Germany) and the clear supernatant (cell lysate) was separated, and stored in −80° C. until use.

Primed conditioned medium was prepared by exposing the hWJSCs to specific hypoxic and/or apoptotic culture medium environments before collecting the conditioned medium. Separately, simple medium containing DMEM high glucose supplemented with L-glutamine and antibiotic/antimycotic solution with/without knockout serum replacement medium (KOSR) was exposed to WJSCs, dying/living apoptotic primary skin and keloid cultures in different oxygen environments (e.g., less than or equal to about 5%) and the conditioned medium separated from the WJSCs after about 24-72 hours. The purpose was to take advantage of any useful ingredients released by the skin and keloid cells. This CM is referred to as primed conditioned medium (PCM).

Preparation of the Nano-Aloe Vera Mesh

Fresh Aloe Vera leaves were collected and washed thoroughly with water and air-dried. The air dried Aloe Vera plant was pulverized and subjected to extraction with methanol. The residual methanol was evaporated using a rota vapour and the final product was then freeze-dried. Polycaprolactone (PCL) (Mol Wt, 80,000) and the crude extract of Aloe Vera was dissolved in hexafluropropanolol by continuous stirring for 24 hrs. The mixed polymer solutions of PCL/Aloe Vera was fed at a flow rate of 1.0 mL/h and high voltage into a 3 ml standard syringe attached to a 22G needle and electrospun as nanofibers on glass cover slips, sterilized and used as scaffolds for growth of the hWJSCs. Separately the same scaffolds were soaked in CM/PCM/lysate.

Fabrication of Aloe Vera/Polycaprolactone Nanofibrous Membrane

Figure 2:
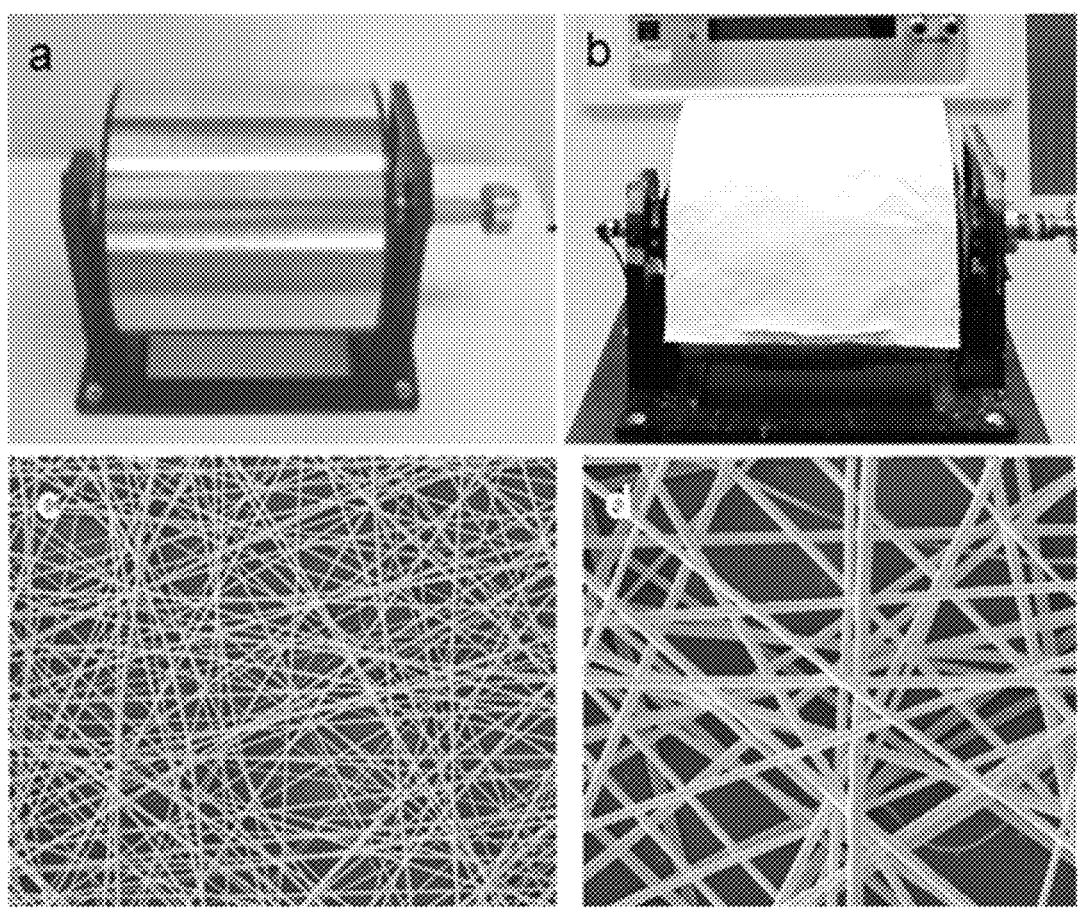
FIGS. 2A-2D show fabrication of PCL/Aloe vera nanofibrous membrane. a) rotating drum, b) rotating drum with nanofibrous membrane, c) SEM image of PCUAloe vera (2500×), d) higher magnification of nanofibers (10000×). The fiber diameter was 400-425 nm, thickness 0.5-1 mm and the membrane porosity of 85% to 95%.

Polycaprolactone (PCL, mol wt, 80,000), chloroform and methanol were purchased from Sigma-Aldrich (USA) and Aloe vera dried powder was a kind gift from Textile engineering at Anna University, Chennai, India. PCUAloe vera (about 15% w/v: about 10:5 ratio) was dissolved in chloroform/methanol (3:1) by stirring with even distribution up to 24 hrs. Electrospinning was conducted in an automated electrospinning machine (Nanon-01A, MECC Co. Ltd. Japan) Nanon for fabricating nanofibrous membranes. A rotating drum covered with aluminum foil as a backing material was used for the collection of nanofibrous membrane. The rotating speed was fixed at 150 rpm for even spraying of nanofibers on the rotating drum. PCL/Aloe vera samples were fed into a 10 ml standard syringe attached to a 18 G blunt stainless steel needle using a syringe pump at a flow rate of 3.0 ml/hr with an applied voltage of 24 kV using a high-voltage power supply. FIG. 2 illustrates the membranes that were developed and morphology of nanofibers. After electrospinning, the developed membrane was exposed to mild convective air flow in a fume hood overnight to remove any residual solvent. The nanofibers were dried under vacuum at room temperature overnight to remove the residual solvent present in the nanofibrous scaffolds. The membrane was cut into 10×10 cm pieces and stored in a desiccator. Cover slips of different sizes (10 to 15 mm) were spread on the rectangular stainless steel stage covered with aluminum foil to collect nanofibers to investigate the biocompatibility with cultured cells as well as to observe the structure and properties of nanofibers. Electrospun nanofibers were sputter-coated with gold (JEOL JFC-1600 Auto Fine Coater, Japan) and visualized by field emission scanning electron microscopy (SEM; FEI-OUANTA 200 F, Czech Republic) at an accelerating voltage of 10 kV for characterization.

The PCL/Aloe vera scaffolds were of a random mesh design and had high porosity (about 85%-95%) with a fiber diameter of about 400-425 nm and thickness of about 0.5 to 1 mm (FIG. 1). High porosity of the nanofibrous scaffold provided more structural space for cells to facilitate exchange of nutrients and metabolic waste between the scaffold and environment more efficiently. Moreover, the scaffold provided a larger surface for cell adhesion and also helped to maintain mechanical stability to protect the wound bed from invasion of microorganisms. These characteristics are preferred criteria for tissue engineered nanofibrous scaffolds. The scaffold provides a surface for cell adhesion and also maintains mechanical stability. The scaffold retains its structural integrity and stability when the physician handles and implants it into the wound. The scaffold (e.g., aloe vera nanomesh) provides sufficient biomechanical support in the wound. PCL/Aloe vera samples were tested for absorbability and biocompatibility using a device (Instron USA) that evaluated mechanical properties of materials. The results which were measured in megapascals showed good absorbability and biocompatibility. The materials used in the fabrication of scaffold involve the integration of both synthetic and natural polymers, e.g., to provide a favorable substrate for the growth of cells such as hWJSCs, epidermal and dermal fibroblasts.

Impregnation of hWJSCs/hWJSC-CM/hWJSC Lysate/hWJSC-PCM into Nano-Aloe Vera Mesh

The nano-aloe vera meshes were impregnated with the following and prepared as a wound dressing patch for applying onto wounds: (1) hWJSCs alone (2) hWJSC-CM, hWJSC lysates or hWJSC-PCM (3) hWJSCs or hWJSC-CM or hWJSC lysate or hWJSC-PCM with or without fibrin.

Labeling of hWJSCs with Green Fluorescent Protein (GFP) or Red Fluorescence Protein (RFP)

The hWJSCs were labeled with GFP or RFP for tracking in the in vitro and animal studies using conventional lentiviral transfection methods. The green or red colors observed in the hWJSCs under fluorescence microscopy aided in their identification.

Cell proliferation ((3-(4,5-Dimethylthiazol-2-yl)-2,5-diphenyltetrazolium bromide (MTT) Assay)

Skin fibroblasts were cultured in basal media at the seeding density of $2 \times 10^4$ cells/well in 0.1% gelatin coated 24-well tissue culture plates (BD, Franklin Lakes, N.J.) and their cell proliferation rates were evaluated following treatment with either hWJSCs, hWJSC-CM, hWJSC-PCM or hWJSC-CL with or without the nanogel mesh for 72 h. Cell proliferation was evaluated using the conventional MTT (3-(4,5-dimethylthiazolyl-2)-2,5-diphenyltetrazolium bromide) assay.

Scratch Assay

Skin fibroblasts were cultured in basal (KOSR) medium at the seeding density of $0.5\times10^6$ in 0.1% gelatin coated 60 mm Petri dish (Nalgene NUNC International, Rochester, N.Y.) and cultured for 24 h. $0.25\times10^6$ cells each of skin fibroblasts and hWJSCs were seeded together in the dishes. Uniform scratches were made in both the control and experimental arms with a 2 ml graduated serological pipette, vertically from top to the bottom of the Petri dish in the midline to mimic a wound. The cell debris were washed gently with PBS and the control and mixed cells arms were cultured in basal (KOSR) medium. Similar scratches were made on confluent monolayers of skin fibroblasts in Petri dishes and the cells exposed separately to hWJSC-CM, hWJSC-PCM, hWJSC-CL with or without nanogel at 37° C. in a 5% $CO_2$ atmosphere for 72 hours. Migration of cells (hWJSCs and in particular skin fibroblasts to show that the presence of hWJSC-CM, hWJSC-PCM or hWJSC-CL sped up the proliferation of skin fibroblasts and hence closure of the scratch) into the scratch (wound) was monitored regularly and imaged using an Olympus inverted phase contrast microscope every 24 h and continued until 72 h or full closure of the scratch (wound), whichever was earlier. Markings on the Petri dishes were used as reference points to obtain the same field during imaging.

Collagen (Sircol) Assay

Skin fibroblasts were cultured in basal medium at the seeding density of $0.5-1\times10^6$ cells in 0.1% gelatin coated T-25 tissue culture flasks (BD, Franklin Lakes, N.J.) for both control and treatment arms. The control arms were cultured in basal (KOSR) medium, while the treatment arms were cultured with hWJSCs, hWJSC-CM, hWJSC-PCM, or hWJSC-CL with or without nanogel mesh at 37° C. in a 5% $CO_2$ atmosphere for 72 hours. The secreted collagen levels from both control and treatment arms were evaluated using Sircol™ (collagen assay) kit (Bioclour, Carrickfergus, UK) according to the manufacturer's instructions. Briefly, 1 ml of the Sircol reagent was added to the 100 μl of the standards and samples (1:20, diluted in distilled water) in 1.5 ml microcentrifuge tubes (Eppendorf); mixed well and placed on a mechanical shaker for 30 min to enable collagen-dye complex precipitation. The contents were then centrifuged at 12000 rpm for 10 min and the supernatant carefully drained taking care to avoid loss of pellet. The unbound dye was removed by layering 750 μl of ice-cold acid-salt wash reagent (Kit content) followed by centrifugation at 12000 rpm for 10 min. The supernatant was carefully removed and 250 μl of alkali reagent (kit content) was added and vortexed to dissolve the bound dye. Absorbance at 555 nm was spectrophotometrically measured using a microplate ELISA reader (μQuant-BioTek, Winooski, Vt.) and collagen concentration calculated based on the concentration of the standards.

Elastin Assay

As described above for the Sircol assay, control and treatment arm dishes were prepared and cultured as above for 72 h. The elastin content of the cells was analyzed using Fastin™ (Elastin assay) kit (Bioclour, Carrickfergus, UK) according to the manufacturer's instructions. Briefly, following culture in respective media the cells were trypsinized, pelleted and treated with 0.25M oxalic acid at (100° C.) for 2 h to convert the native hydrophobic elastin into water soluble α-elastin. To both standards and samples (50 μl) elastin precipitating reagent (kit content) was added and incubated at RT for 15 min, followed by centrifugation at 10000×g for 10 min. The tube contents were carefully drained and 1 ml of Dye reagent (kit content) was added and mixed using vortex and mechanical shaker for 90 min. The contents were again centrifuged at 10000×g for 10 min and the supernatant drained completely. The bound elastin was then released by addition of 250 μl Dye Dissociation reagent (kit content) and absorbance at 513 nm was spectrophotometrically measured using a microplate ELISA reader (μQuant-BioTek, Winooski, Vt.) and elastin concentration calculated based on the concentration of the standards.

Quantitative Real Time Polymerase Chain Reaction (qRT-PCR)

Skin fibroblasts were cultured in basal (KOSR) medium at the seeding density of $0.5-1\times10^6$ cells in 0.1% gelatin coated T-25 tissue culture flasks (BD, Franklin Lakes, N.J.) for both control and treatment arms. The control arms were cultured in basal (KOSR) medium, while the treatment arms were cultured in either hWJSCs/hWJSC-CM/hWJSC-PCM/ hWJSC-CL at 37° C. in a 5% $CO_2$ atmosphere for 72 hours. Total RNA was extracted from the cells using RNeasy PLUS minikit (Qiagen, USA) and subjected to qRT-PCR.

Evaluation of Successful Healing

Healing rate was evaluated by time taken for wound closure using digital photographs and a NIH image analysis program. Wound biopsies were collected and subjected to histopathology for re-epithelialization, vascularity, thickness of granulation tissue, mitotic figures using wound healing models (Yew et al., *Cell Transplantation*, 20.693-706 (2011); Chen et al., *PLoS One*, 4:7119 (2009)).

From both in vitro and in vivo experiments, surgical and diabetic wounds healed much faster than wounds treated with skin fibroblasts/keratinocytes (or their CM/PCM/CL) or untreated controls. There was increased cell proliferation in the wounds following exposure to hWJSCs, hWJSCs-CM, hWJSCs-PCM, or hWJSCs-CL compared to controls (treatment with skin fibroblasts/keratinocytes (or their CM/PCM/CL) or untreated controls). Cell migration into skin fibroblast scratches (wounds) increased following exposure to hWJSCs, hWJSC-CM, hWJSC-PCM, or hWJSC-CL compared to controls. Secretion of collagen was increased by greater than 50% and elastin by 125%-150% following treatment of wounds with hWJSCs, hWJSC-CM, hWJSC-PCM or hWJSC-CL. Additionally, gene expression using qRT-PCR showed increases of collagen type I, collagen type II and fibronectin in the wounds. The presence of the aloe vera nanomesh encouraged wound healing and healing time was faster than the use of hWJSCs, hWJSC-CM, hWJSC-PCM or hWJSC-CL alone.

Immunohistochemistry was carried out on wound biospies to identify survival of GFP/RFP labeled hWJSCs and hWJSC-derived keratinocyte markers (e.g., filaggrin, involucrin, pancytokeratin).

Methods of Application of Dressing

Examples of ways in which the dressing can be applied to wounds and dosages are provided below:

i. Injected hWJSCs (at doses of about 0.5 to $10\times10^6$ cells or more in 100 μl of PBS or in one or multiple injections periodically into the epidermis and dermis of the wound).

ii. Injected hWJSC-CM/hWJSC/PCM/hWJSC-CL (at doses of about 100 μl in one or multiple injections periodically into the epidermis and dermis of the wound. hWJSC-CM/hWJSC-PCM can be conditioned for about 24-72 h and used at concentrations of about 50%-100%. The protein content in the hWJSC-CL can range from about 15-30 μg/L).

iii. The hWJSCs/hWJSC-CM/hWJSC-PCM/hWJSC-CL can also be administered to the wound in the forms of aerosol sprays, gels, creams, masques or fresh/frozen-thawed solutions.

iv. The hWJSCs/hWJSC-CM/hWJSC-PCM/hWJSC-CL can be impregnated into a mesh (e.g., an aloe vera nanomesh) (wet and dry dressings) and then applied to wounds or the mesh can be applied to the wound first and then the hWJSCs/hWJSC-CM/hWJSC-PCM/hWJSC-CL impregnated into the mesh. Dosing of the nanomesh can be once or multiple times. The mesh can biodegrade (e.g., in about 1-4 weeks).

Results

From both the in vitro and animal experiments, surgical and diabetic wounds healed much faster than wounds treated with skin fibroblasts/keratinocytes (or their CM/PCM/CL) or untreated controls. There was increased cell proliferation in the wounds following exposure to hWJSCs/hWJSC-CM/hWJSC-PCM/hWJSC-CL compared to controls (treatment with skin fibroblasts/keratinocytes (or their CM/PCM/CL) or untreated controls). Cell migration into skin fibroblast scratches (wounds) increased following exposure to hWJSCs/hWJSC-CM/hWJSC-PCM/hWJSC-CL compared to controls. Secretion of collagen was increased by greater than 50% and elastin by 125%-150% following treatment of wounds with hWJSCs/hWJSC-CM/hWJSC-PCM/hWJSC-CL. Additionally, gene expression using qRT-PCR showed increased collagen type I, collagen type III and fibronectin in the wounds. The presence of the aloe vera nanomesh encouraged wound healing and healing time was faster than the use of hWJSCs/hWJSC-CM/hWJSC-PCM/hWJSC-CL alone.

Discussion

1. The dressing is useful for a variety of wound types such as (a) surgical incisional wounds (b) traumatic wounds (c) diabetic wounds and ulcers (d) burns (e) suppression of keloids.

2. hWJSCs differentiated into keratinocytes (new skin cells) in the wounds that helped in healing and wound closure. This was confirmed by the presence of GFP-labeled hWJSCs in wound biopsies as well as increases in keratinocyte markers (e.g., filaggrin, involucrin, pancytokeratin) in the GFP-labeled cells in wound biopsies.

3. The increased production of PGE2 (ELISA kit from i-DNA Biotechnology, Singapore) in wounds was an indication of tissue regeneration.

4. hWJSCs/hWJSC-CM/hWJSC-PCM/hWJSC-CL reduced wound inflammation and improved re-modelling compared to controls (skin fibroblasts/keratinocytes or its CM/PCM/CL and untreated wounds).

5. Scanning electron microscopy showed that the aloe vera nanomesh provided niches for the hWJSCs to attach, proliferate and differentiate into keratinocytes. The aloe vera nanomesh acted like a sieve for even distribution and slow release of molecules from the impregnated hWJSCs/hWJSC-CM/hWJSC-PCM/hWJSC-CL into all parts of the wound to encourage healing. The aloe vera nanomesh biodegrades in about 1-4 weeks.

6. It has previously been reported that hWJSCs secrete microRNAs and several bioactive soluble molecules such as cytokines, glycosaminoglycans, collagen and hyaluronic acid. hWJSCs/hWJSC-CM/hWJSC-PCM/hWJSC-CL promote wound healing by secretion of various cytokines and growth factors that stimulate fibroblast proliferation (Fong et al., *J Cell Biochem*, 113:658-668 (2012); Fong et al., *Stem Cell Rev and Rep*, 8:195-209 (2012); Gauthaman et al., *J Cell Biochem*, 113:2027-2039 (2012)).

7. Collagen released by hWJSCs/hWJSC-CM/hWJSC-PCM/hWJSC-CL helped wound healing, tissue reconstitution, fibroblast formation and tissue remodelling.

8. The secretion of elastin by hWJSCs/hWJSC-CM/hWJSC-PCM/hWJSC-CL provided mechanical strength, elasticity and resilience to the wound.

9. hWJSCs are hypoimmunogenic, non-tumorigenic and do not become transformed into tumor associated fibroblasts and therefore their use in wound healing is both advantageous and safe.

10. The aloe vera nanomesh and hWJSCs/hWJSC-CM/hWJSC-PCM/hWJSC-CL can be refined and prepared under cGMP conditions for human application. hWJSCs are non-controversial and available in abundance from discarded umbilical cords. They are highly proliferative and can be scaled up in large numbers. The aloe vera nanomesh is inexpensive to produce and hence the final dressing is cost-effective and can be produced on a large scale for application.

11. The aloe vera nanomesh impregnated with hWJSCs/hWJSC-CM/hWJSC-PCM/hWJSC-CL can be further impregnated with antibiotics, silver particles or any other useful molecules to treat stubborn wounds.

Example 2

Human Umbilical Cord Wharton's Jelly Stem Cells and its Conditioned Medium Enhance Healing of Excisional and Diabetic Wounds Poor healing of wounds is a challenging problem in patients and current treatments have met with limited success. This problem is growing worldwide due to an aging population and rise in diabetes and obesity. The treatment of excisional and diabetic wounds using a stem cell isolated from the human umbilical cord Wharton's jelly (hWJSC) that shares unique properties with embryonic and adult mesenchymal stem cells was evaluated. hWJSCs are non-controversial, available in abundance, hypo-immunogenic, non-tumorigenic, differentiate into keratinocytes and secrete important molecules for tissue repair. When conventional scratch-wound assays of human skin fibroblasts (CCD) were exposed to hWJSC-conditioned medium (hWJSC-CM) the skin fibroblasts at the wound edge proliferated and migrated into the wound space significantly faster and showed increased secretion of collagen, elastin and fibronectin compared to controls. When a single application of green fluorescent protein (GFP)-labelled hWJSCs (GFP-hWJSCs) or hWJSC-CM was administered to full-thickness murine excisional and diabetic wounds, healing rates and wound closure were significantly faster compared to controls. Wound biopsies collected at various time points showed the presence of green GFP-labelled hWJSCs, positive human keratinocyte markers (cytokeratin, involucrin, filaggrin) and expression of ICAM-1, TIMP-1 and VEGF-A. On histology, the GFP-hWJSCs and hWJSC-CM treated wounds showed reepithelialisation, increased vascularity and cellular density and increased sebaceous gland and hair follicle numbers compared to controls. hWJSCs showed increased expression of several miRNAs associated with wound healing compared to CCDs. The studies herein demonstrated that hWJSCs and extracts thereof enhance healing of excisional and diabetic wounds via differentiation into keratinocytes and release of important molecules.

Described herein is the evaluation of hWJSCs and its conditioned medium (hWJSC-CM) in wound healing using conventional in vitro scratch-wound migration assays and in vivo full-thickness excisional and diabetic wounds created in immunodeficient and diabetic mice. Since skin cell turnover is under the cont rol of MSCs this was the theoretical basis for this study.

Materials and Methods

Ethical Approval for Use of Human Cells and Animals

Ethical approval with informed patient consent for the use of human umbilical cords for this study was given by the Institutional Domain Specific Review Board (DSRB), Singapore. hWJSCs were derived, propagated and characterized according to our earlier published protocols [Bongso, A and Fong C Y et al. *Stem Cell Reviews and Reports*, 9:226-240 (2013)]. Commercial skin fibroblasts (CCD-1112sk) (abbreviated as CCD) were purchased from the American Type Culture Collection (ATCC—Rockville, Md., USA) and ethical approval for their use was given by the National University of Singapore, Institutional Review Board (NUS-IRB). All animal procedures were approved by the National University of Singapore Institutional Animal Care and Use Committee (IACUC).

Cell Culture

Umbilical cords were collected at full term delivery in transport medium (Hank's Balanced Salt Solution supplemented with antibiotic-antimycotic solution, Invitrogen Life Technologies, Carlsbad, Calif.), stored at 40° C. and processed within 12 h after collection. Each cord was cut first into 2 cm pieces and each of the pieces cut open lengthwise and placed with its inner surface facing down in a 60 mm Petri dish containing an enzymatic solution. The enzymatic solution comprised of 2 mg/ml collagenase type I, 2 mg/ml collagenase type IV and 100 IU/ml hyaluronidase (Sigma, Mo.) in DMEM High glucose medium (Invitrogen). The umbilical blood vessels were not removed. The dishes were then incubated at 37° C. for 30-45 min to facilitate detachment and loosening of the Wharton's jelly into culture medium. The gelatinous Wharton's jelly was then collected into sterile syringes and the hWJSCs then separated from the Wharton's jelly by syringing the gelatinous masses through a hypodermic needle. The isolated hWJSCs were cultured in sterile tissue culture flasks [Becton Dickinson (BD) Franklin Lanes, N.J.] using hWJSC culture medium comprising DMEM-high glucose medium supplemented with 20% fetal bovine serum (FBS), 16 ng/ml basic fibroblast growth factor (Millipore Bioscience Research agents, Temecula, Calif.), 1% non-essential amino acids, 2 mM L-glutamine, 0.1 mM β-mercaptoethanol, 1% insulin-transferrin-selenium and 1% antibiotic-antimycotic mixture [penicillin (100 units/ml), streptomycin (100 μg/ml) and amphotericin B (0.25 μg/ml)] (Invitrogen). The commercial frozen CCDs were thawed and cultured in sterile tissue culture flasks (BD) in DMEM-high glucose medium supplemented with 10% FBS, 2 mM L-glutamine and antibiotic-antimycotic mixture. After establishment of confluent monolayers the hWJSCs and CCDs were detached from the plastic dishes with trypsin-EDTA (TrypLETM Express, Invitrogen), dissociated, washed and seeded on 0.1% gelatin-coated tissue culture plates in a basal medium devoid of proteins comprised of DMEM-high glucose, 10% knockout serum replacement (KOSR), 1% L-glutamine and 1% antibiotic-antimycotic mixture (KOSR medium, Invitrogen) for the in vitro experiments and DMEM-high glucose, 1% L-glutamine and 1% antibiotic-antimycotic mixture for the in vivo experiments of the present study. A protein-free basal medium was used in both in vitro and in vivo studies so as to take advantage of the various proteins released by the hWJSCs and CCDs.

Labelling of hWJSCs with Green Fluorescence Protein (GFP)

The hWJSCs were infected with a lentiviral vector for GFP. Briefly, lentiviral vectors were produced by transient transfection of Lenti-X™ 293 T Cells (Clontec Laboratories Inc, Mountain View, Calif.). hWJSCs ($5 \times 10^6$ cells/plate) were seeded in 10 cm tissue culture plates 24 h before transfection. Transfection was performed using the calcium phosphate precipitation method. Cells were replaced with fresh medium at 14-16 h after transfection. The supernatant was filtered through a 0.45 mm filter and the titer of the supernatant of the 293T cells was determined using flow cytometry. The hWJSCs were infected with unconcentrated lentiviral supernatant at a multiplicity of infection (MOI) of 5-10.

Conditioned Medium hWJSCs and CCDs at passages 3-4 (P3-P4) were grown to 80% confluence in basal medium with/without KOSR and the medium separated after 72 h as hWJSC conditioned medium (hWJSC-CM) and CCD conditioned medium (CCD-CM) respectively. The conditioned media were filter-sterilized using a 0.22 μm Millex-GP syringe filter (Millipore, Billerica, Mass.) and the pH and osmolality of the media standardised before use in experiments. The mean±SEM pH and osmolality of the hWJSC-CM and CCD-CM were 7.75±0.26 and 332.67±1.20 and 7.88±0.18 and 332.33±0.88, respectively. Both hWJSC-CM and CCD-CM were diluted 1:1 v/v in basal medium with/without KOSR and used as 50% hWJSC-CM and 50% CCD-CM for all experiments. Our previously published work on the composition of hWJSC-CM showed that it contained a family of cytokines, growth factors, glycosoaminoglycans and cell adhesion molecules [Gauthaman K, et al., *Reprod BioMed Online*, 24:235-246 (2012); Fong C Y, et al., *J Cell Biochem*, 113:658-668 (2012)].

Scratch-Wound Assay

Several dishes were prepared using the same batch of CCDs for conventional scratch-wound assays according to the method of Cory [Cory, G., *Meth Molec Biol*, 769:25-30 (2011)]. Briefly, CCDs were cultured in KOSR medium at a seeding density of $0.5 \times 10^6$ cells on 0.1% gelatin-coated 60 mm Petri dishes (Nalgene NUNC International, Rochester, N.Y.) and incubated at 37° C. in a 5% $CO_2$ in air atmosphere for 24 h to generate confluent monolayers. Linear scratches (0.5 mm width) were made vertically from top to bottom in the midline of the confluent CCD monolayers using a sterile pipette. The scratched dishes were then divided into one treatment arm (hWJSC-CM) and two controls [CCD-CM and unconditioned KOSR medium (UCM)]. The scratched dishes were seeded with 2 ml of hWJSC-CM, CCD-CM and UCM respectively. All treatment and control dishes were then incubated at 37° C. in a 5% CO2 in air atmosphere for 72 h. Three replicates were carried out for each assay. CCD migration from the scratched edges into the vacant scratches and final scratch closure was monitored regularly and digitized images of at least 5 random fields within the scratches were taken every 24 h using inverted phase contrast optics until 72 h or full closure of the scratches. Markings on the Petri dishes were used as reference points to monitor the same fields every 24 h. The mean±SEM percentage extent of closure of the scratches at 24, 48 and 72 h were calculated from the digitized images using an image software program [26]. The MTT assay was used to calculate viable CCD numbers to find out whether the respective treatments had stimulated CCD proliferation and survival in addition to migration. The MTr assay was carried out using a MTT reagent kit [3-(4,5-dimethylthiazolyl-2)-2,5-diphenyltetrazolium bromide](Sigma, St. Louis, Mo.) according to the manufacturer's instructions. Absorbance at 570 nm was spectrophotometrically measured using a microplate ELISA reader (LtQuant-BioTek, Winooski, Vt.) with a reference wavelength of 630 nm.

Sircol (Collagen) and Fastin (Elastin) Assays

The total collagen (Types I to V) and elastin levels in the treatment and control arms were evaluated and compared using the Sircol™ (collagen assay) and Fastin™ (Elastin assay) kits (Bioclour, Carrickfergus, UK) according to the manufacturer's instructions. Absorbance at 555 nm was spectrophotometrically measured using a microplate ELISA reader (tQuant-BioTek, Winooski, Vt.) and collagen concentration calculated based on the concentration of the standards.

Quantitative Real Time Polymerase Chain Reaction (qRT-PCR)

CCDs exposed to treatment and control arms were subjected to qRT-PCR.

Total RNA was extracted using TRIzol™ reagent (Invitrogen). RNA quality and quantity were measured using a Nanodrop™ spectrophotometer (Nanodrop Technologies, Wilmington, DW) and all samples were treated with DNase-I prior to first strand cDNA synthesis with random hexamers using the SuperScript™ first strand synthesis system (Invitrogen). Primer sequences were taken from earlier published studies and are given in Table 1. QRT-PCR analysis was performed with the ABI PRISM 7500 Fast Real-Time PCR System (Applied Biosystems, Foster City, Calif.) using SYBR green as previously described and relative quantification was performed using the comparative CT (2-AACT) method.

Full Thickness Wound Model in SCID and Diabetic Mice

For the evaluation of hWJSCs or hWJSC-CM on the healing of excisional wounds a total of 45 female severely combined immunodeficient (SCID) mice aged 5-6 weeks were obtained from the Animal Resources Centre, Western Australia. After the mice were allowed acclimatization for a week they were anaesthetized using isofluorane, dorsal regions shaved and two 8-mm full-thickness circular wounds created on left and right dorsal sides using a dermal punch (Accusharp Punch, India). All wounds were covered with Tegaderm (3M) and edges sealed with Dermabond™ (Ethicon). Dermabond™ helps in preventing the mice removing the Tegaderm plaster and is an FDA approved adhesive that forms a protective barrier against bacteria. The 45 mice (90 wounds) were divided into 5 groups (9 mice/group; 18 wounds in each group treated as follows [Gp 1 (Treatment): GFP-hWJSCs ($1\times10^6$ cells in KOSR medium); Gp 2 (Treatment): hWJSC-CM (100 µl); Gp 3 (Control): GFP-CCD ($1\times10^6$ cells); Gp 4 (Control): CCD-CM (100 µl) and Gp 5 (Control): Unconditioned KOSR medium (UCM) (100 µl)]. The cells and media were administered intradermally using a 25G hypodermic needle at several sites at the margins of the wounds. The animals were individually housed under a 12:12 h light-dark cycle, under SPF conditions and allowed access to food and drinking water.

For the diabetic wound evaluation, a similar experimental design as above was carried out on full-thickness (6 mm) wounds created in commercial diabetic mice (Strain BKS.Cg-Dock7m+/+Leprdb/J; Stock No: 000642 resembling Type IIDM) obtained from Jackson Laboratories, USA. A smaller sized wound punch was chosen for the diabetic wounds to simulate other published diabetic murine studies [Sullivan S R, et al., *Plast Reconstr Surg*, 113:953-960 (2004); Wu, Y, et al., *Stem Cells*, 25:2648-2659 (2007)]. Glucose levels were measured before, during, and after the experiment to confirm that the mice were diabetic. A total of 36 mice (72 wounds) were divided into 3 groups (12 mice/group; 24 wounds) and the diabetic wounds in each group treated as follows: [Gp 1(Treatment): GFP-hWJSCs ($1\times10^6$ cells); Gp 2 (Treatment): hWJSC-CM (100 µl); Gp 3 (Control): UCM (100 µl)]. Injections were administered intradermally using a 25G hypodermic needle at several sites at the margins of the wounds. Wound healing was visually monitored and documented daily. Digital photographs were taken on days 0, 7 and 14 for excisional wounds by the same operator. Complete wound closure was defined as 100% reepithelialization without remaining scab formation. Healing rates were calculated from the digital images using a NIH recommended formula and Image software by two independent observers blinded to treatments. The formula used was as follows: (original wound area−new wound area)/original wound area×100 [Chen, L, et al. *PLOS One*, 4:e7119 (2009)]. At specific time points wound biopsies were collected and (i) frozen for cryostat sectioning for fluorescent microscopy and immunohistochemistry; (ii) fixed in 10% buffered formalin and 4% buffered paraformaldehyde for histology and fluorescent microscopy respectively; and (iii) snap-frozen in liquid nitrogen for genomic and molecular analysis. Each of these analyses was carried out in a blinded fashion by staff experienced in these areas in their respective laboratories. For histology, at least 4-7 different sections were examined for each arm in treatment and control groups. Normal murine skin samples from SCID and diabetic mice were used as positive controls for comparison.

Identification of GFP Signals and Keratinocyte Markers in Wound Samples

The wound samples collected for fluorescent microscopy that were fixed in 4% buffered paraformaldehyde were washed in PBS for 24 h and perfused in 18% sucrose for 24 h. The samples were then mounted in Tissue-Tek® OCT Compound (Sakura Finetek USA Inc., CA) and stored at −80° C. Cryosections (5 µm) were cut using a cryostat (CM1650; Leica, Germany) and mounted on glass slides coated with polysine (Thermo Scientific). The sections were exposed to a blocking solution of 10% normal goat serum and then incubated with mouse monoclonal anti-human filaggrin (Abcam, Cambridge, UK), anti-human involucrin (Genway, San Diego, Mo., USA) and anti-human cytokeratin (clone AE1/AE3) (Dako, Carpinteria, Calif., USA) overnight. The samples were then washed in PBS three times (10 min each time) and exposed to Cy3-conjugated secondary antibodies (Abcam) for 1 h. Finally, the samples were washed in PBS thrice and mounted with Fluoroshield™ with DAPI (Sigma, St Louis, Mo., USA) together with a cover slip. The sections were examined and photographed with a digital camera under a fluorescent microscope (Nikon Eclipse, Ti-S, Nikon Corporation, Tokyo, Japan) fitted with blue (DAPI), green (GFP) and red (Cy3) filters.

Gene Expression Analysis in Wound Samples

Murine gene expression for VEGF-A, TIMP-1 and ICAM-1 in wound biopsies were analysed by the Quantitative Real-Time PCR TaqMan method. Briefly, total RNA was isolated from treatment and control wound samples (n=3 per arm), homogenized using TissueLyser LT (Qiagen) and a Universal Tissues EZI kit and used as a substrate (1 µg) for reverse transcription using a High Capacity cDNA Reverse Transcription Kit (Applied Biosystems). TaqMan Fast Advance Mastermix (Applied Biosystems) was used for Fast Real-Time PCR. Quantification of VEGF-A expression was performed with the TaqMan Gene expression Assay (Applied Biosystems) for the target VEGF gene (Mm01281449_m1). Quantification of cytokine release (TIMP-1 and ICAM-1) was performed using quantitative real-time PCR. TaqMan Gene Expression Assays (Applied Biosystems) were used for the target genes TIMP-1

(Mm00441818_m1) and ICAM-1 (Mm00516023_m1). The endogenous reference genes (Mm99999915_g1) for GAPDH were used for quantitative real-time PCR.

Statistical Analysis of In Vitro and In Vivo Studies

For the in vitro studies the differences observed between treatment and control groups were compareid and analysed using Students t-test. The results were expressed as mean±SEM from three different replicates for individual assays and a value of p<0.05 was considered to be statistically significant. For the in vivo studies the results were expressed as mean±SEM and analysed by ANOVA and the post-hoc test with least-significant difference (LSD). Statistical significance was determined using SPSS software, version 13.0 (SPSS, Chicago) and P values of <0.05 were regarded as statistically significant.

Total RNA Extraction and Microarrays

Total RNA (+miRNA) was extracted from hWJSCs and CCDs by a single-step method using TRIzol reagent (Invitrogen, Life Technologies, USA) according to manufacturers' protocol. miRNA array was performed [Karolina, D S, et aL, *PLoS ONE,* 6:e22839 (2011)] using total RNA (1 ug) which was 3'-end-labelled with Hy3 dye using the miRCURY LNA™ Power Labeling Kit (Exiqon, Denmark) and hybridized for 16-18 hrs on miRCURY LNA™ Arrays (MirBase version 16) using the MAUI® hybridization system. The microarray chips were then washed and scanned using an InnoScan700, microarray scanner (Innopsys, Carbonne, France) and analysed on Mapix® Ver4.5 software.

The first stage of analysis on microarray data was performed using Partek® 6.6 Genomics Suite software (Copyright, Partek Inc., St Louis, Mo.). Briefly, background-subtracted median signal intensity of miRNAs was used for analysis. First stage of normalization was carried out against a group of endogenous controls and the spike-in controls for each chip to avoid technical and experimental variations for the hWJSCs and the CCD miRNA profiles. The normalized data was subjected to one-way ANOVA and the differentially regulated miRNAs were selected following Benjamini-Hochberg false discovery rate (FDR) correction. All statistical analysis was performed using the statistical tools provided by Partek® 6.6 Genomics Suite software.

Results

Growth and characterization of hWJSCs and CCDs

In-house derived hWJSC and commercial skin fibroblast (CCD1112sk) (abbreviated as CCD) cell lines were successfully established and characterized before their use. When green fluorescent protein (GFP)-labelled hWJSCs and CCDs were cultured in a protein-free basal medium with knock-out serum replacement (KOSR medium) they adhered well to plastic, maintained their typical fibroblastic morphology and became confluent. The GFP-hWJSCs were positive for the CD signature markers (CD10, CD13, CD29, CD44, CD90), and satisfied the criteria for MSCs [Dominici, M, et al. *Cytotherapy,* 8:315-317 (2006)]. They also had low level expression of OCT4, NANOG and SOX2.

Scratch-Wound Assay

Figures 3A, 3B, 3C:
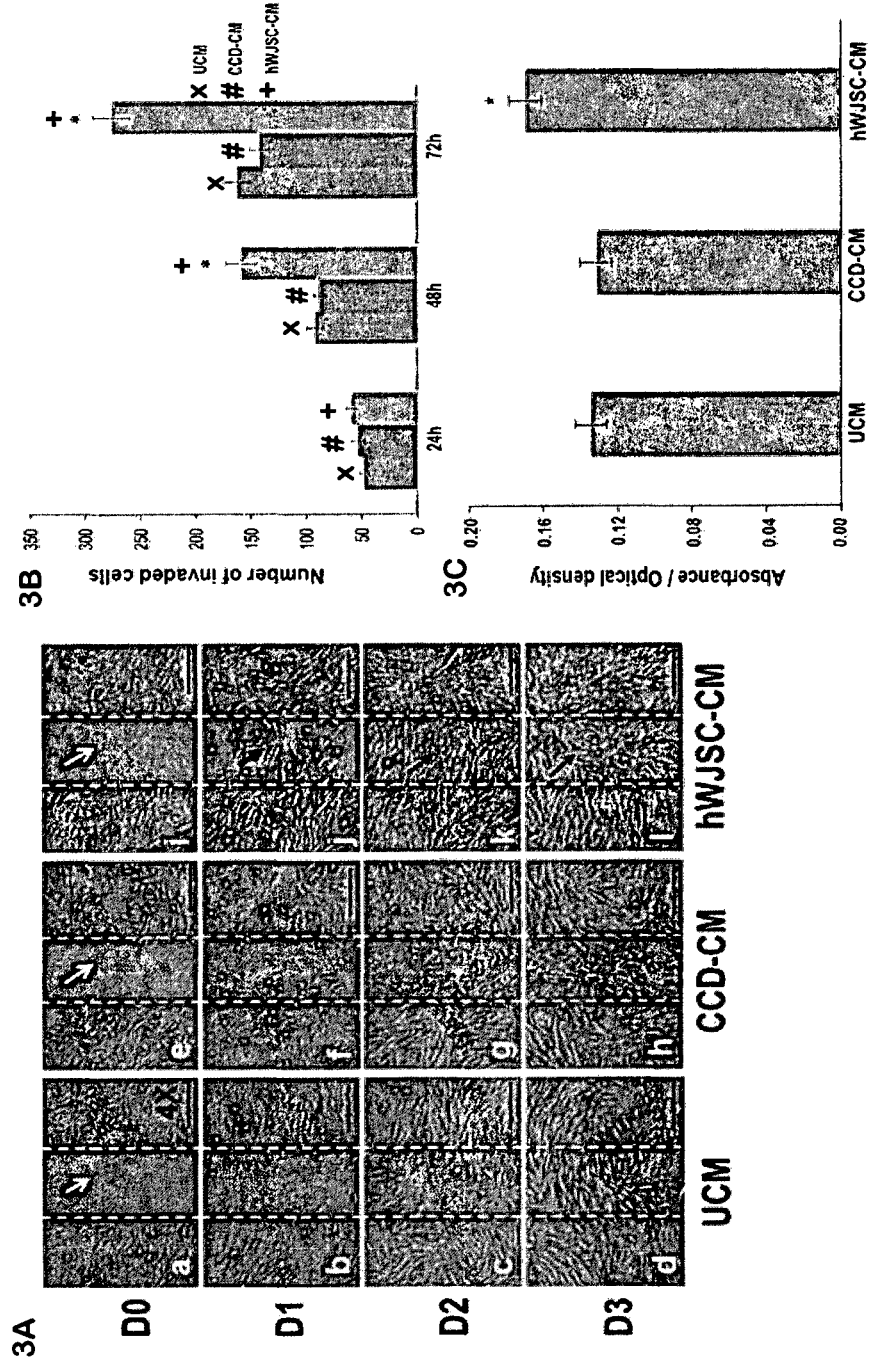
FIGS. 3A-3C: (3A) Scratch-wound assay of CCD fibroblasts exposed to hWJSC-CM (0-72 h) (D0-D3). a-d: CCD fibroblasts grown in unconditioned medium KOSR medium (UCM) (control); e-h: CCD fibroblasts grown in CCD-CM (control); i-l: CCD fibroblasts grown in hWJSC-CM (treatment). White arrows in a, e and i indicate vertical scratches in middle of monolayer with no CCD fibroblasts at D0. Black arrows in j, k and l show faster migration of CCDs into scratches in hWJSC-CM arm compared to controls. The scratches in the hWJSC-CM arm were fully closed by D2. (3B) The mean±SEM number of invaded cells into the scratch-wound were significantly greater in the hWJSC-CM arm compared to both controls at 48 h and 72 h (*$p<0.05$) (3C) The mean±SEM CCD viability (MTT assay) was significantly greater in the hWJSC-CM arm compared to both controls at 72 h (*$p<0.05$).

The skin fibroblasts in scratch-wound assays when exposed to the hWJSC-CM treatment arm started to migrate from the edges of the scratches ('wounds') into the wound spaces as early as 6-8 h and then completely covered the spaces by day 2 (48 h) compared to controls [CCD conditioned medium (CCD-CM) and unconditioned KOSR medium (UCM)](FIG. 3A). The mean t SEM percentage wound closure rates were significantly greater in the hWJSC-CM arm compared to controls (p<0.05) (FIG. 3B). The mean t SEM cell numbers that migrated into the wound areas as determined by two independent observers were 60±04 (hWJSC-CM), 53±06 (CCD-CM) and 48±04 (UCM) at 24 h; 159±13 (hWJSC-CM), 88±05 (CCD-CM) and 92±07 (UCM) at 48 h; and 276±17 (hWJSC-CM), 142±09 (CCD-CM) and 163±12 (UCM) at 72 h respectively. The CCD viability (MTT assay) for the treatment arm (hWJSC-CM) was significantly greater than the controls (FIG. 3C).

Collagen and Elastin (Sircol and Fastin Assays)

Figures 4A, 4B, 4C, 4D, 4E:
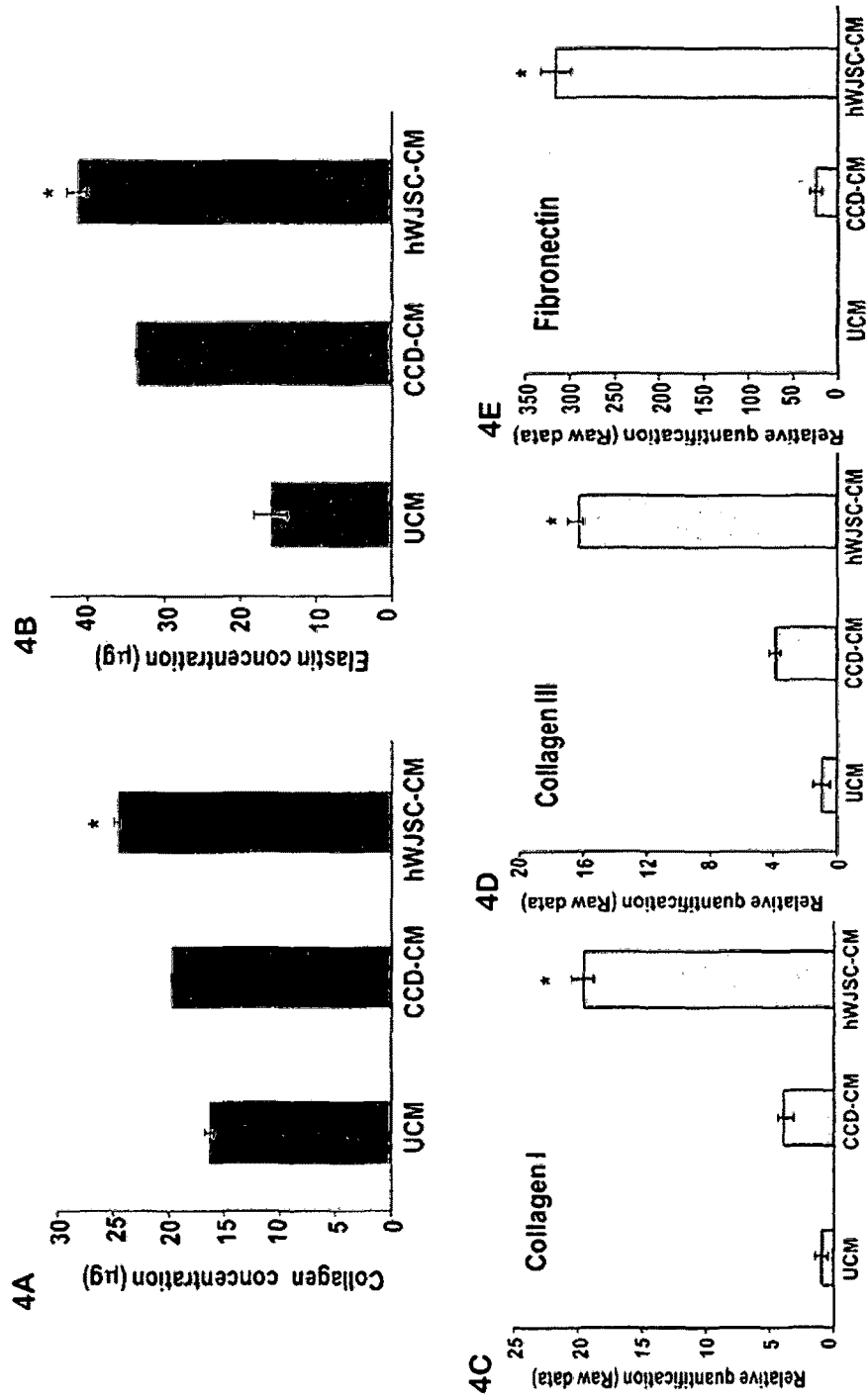
FIGS. 4A-4E: (4A, 4B) The mean±SEM levels of collagen (Sircol assay) and elastin (Fastin assay) were significantly greater in the hWJSC-CM treatment arm compared to controls (*$p<0.05$). (4C-4E) qRT-PCR analysis showed significantly greater expression of (4C) collagen type I, (4D) collagen type II and (4E) fibronectin in the hWJSC-CM arm compared to controls (*$p<0.05$). GAPDH was the internal control. Data analysis and relative quantitation was done using the comparative Ct ($\Delta\Delta CT$) method.

The collagen and elastin concentrations in the scratch-wound assays were significantly greater in the treatment arm (hWJSC-CM) compared to the controls (p<0.05) (FIGS. 4A and 4B).

Collagen Type I, III and Fibronectin (qRT-PCR)

QRT-PCR of the skin fibroblasts in scratch-wound assays exposed to the treatment arm (hWJSC-CM) showed significantly greater expression of collagen type I, collagen type III and fibronectin compared to the controls (CCD-CM and UCM) (p<0.05). The increase in gene expression of fibronectin for the hWJSC-CM arm was 300 fold compared to 40 fold for the CCD-CM arm. Collagen I and III were increased by 17-20 folds for the hWJSC-CM arm compared to 3-4 folds for the CCD-CM arm (FIGS. 4C, 4D and 4E).

Healing Rates and Histology of Excisional and Diabetic Wounds in Mice

Figures 5A, 5B, 5C:
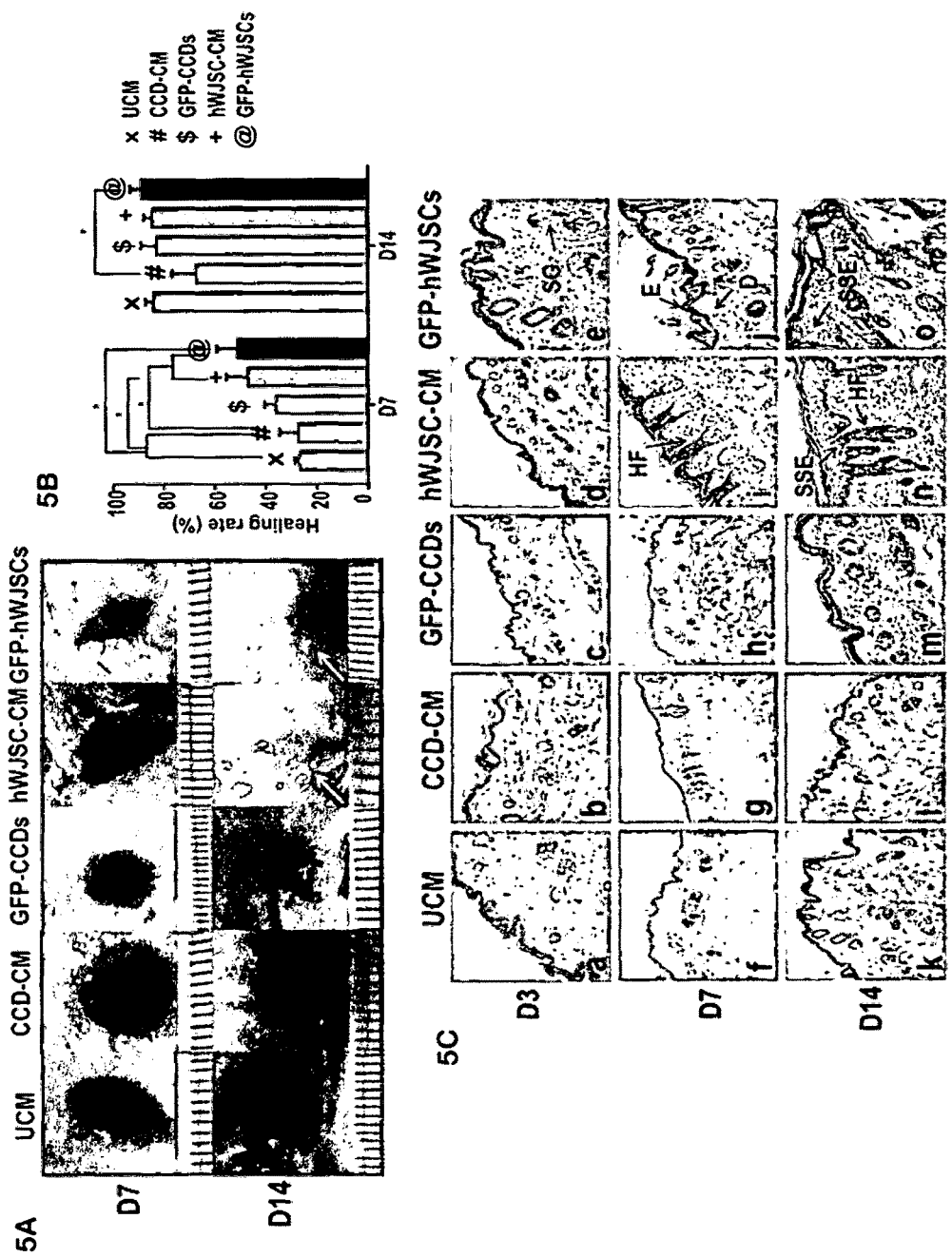
FIGS. 5A-5B: (5A) Digital images of mouse excisional wounds showing faster wound closure by 14 days (D14) in SCID mice exposed to GFP-hWJSCs and hWJSC-CM (treatment arms) (white arrows) compared to controls (GFP- CCDs, CCD-CM and UCM). (5B) Mean±SEM percentage healing rates in excisional wounds in SCID mice were significantly faster in the treatment arms (GFP-hWJSCs and hWJSC-CM) compared to controls on day 7 (*p<0.05). The mean±SEM percentage wound closure rates were significantly faster for the GFP-hWJSCs treatment arm compared to controls on day 14 (*p<0.05).
Figures 5A, 5B:
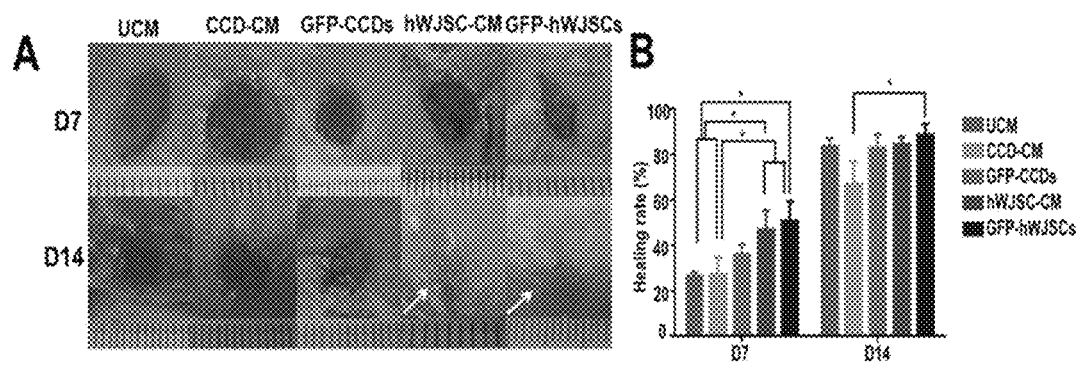
Figures 6A, 6B, 6C:
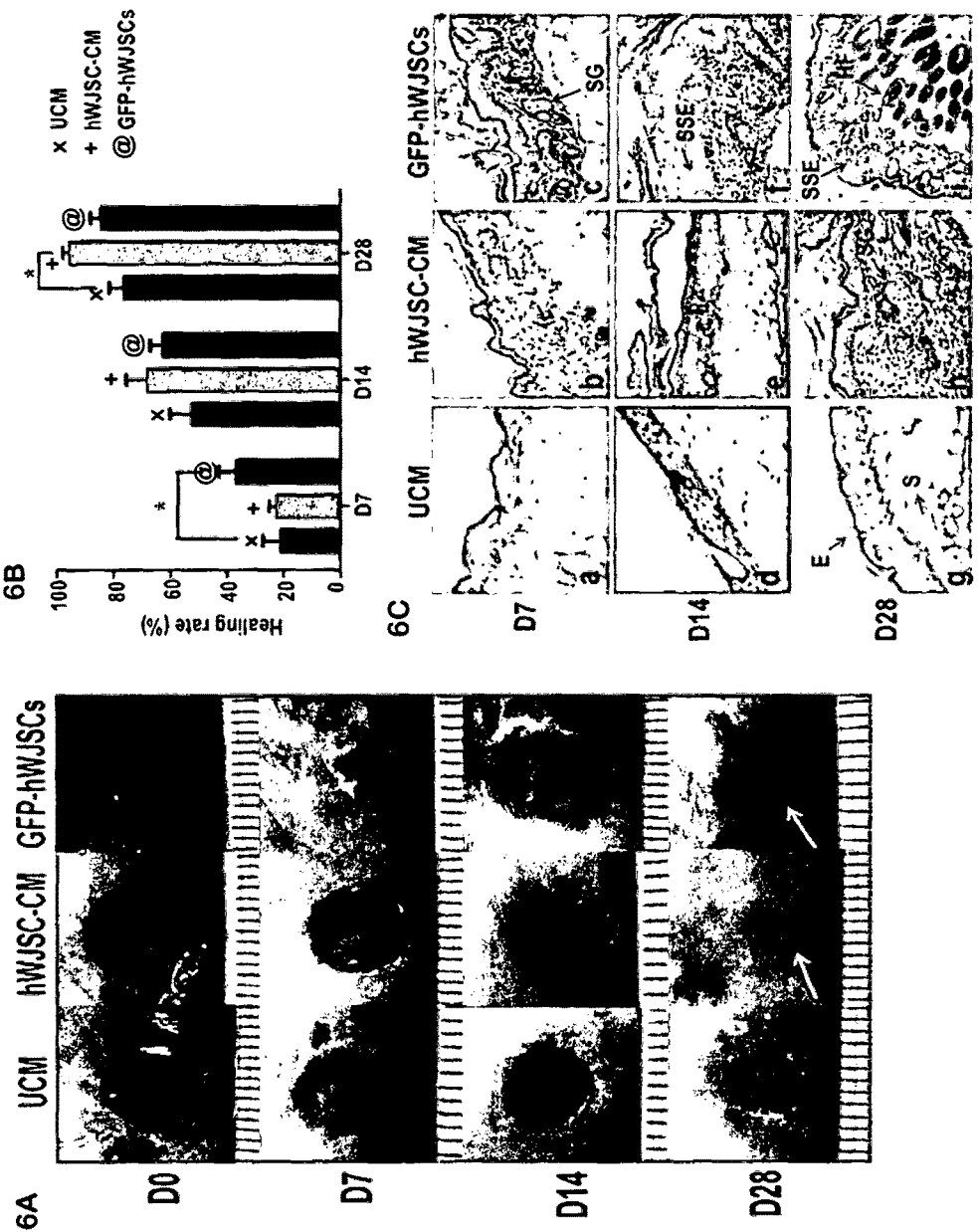
FIGS. 6A-6C: (6A) Digital images of mouse diabetic wounds showing faster wound closure by 28 days (D28) in diabetic mice exposed to GFP-hWJSCs and hWJSC-CM (treatment arms) (white arrows) compared to controls (UCM). (6B) Mean±SEM percentage healing rates in diabetic wounds in diabetic mice were significantly faster in the GFP-hWJSCs treatment arm at D7 and in the hWJSC-CM treatment arm at D28 compared to controls (*p<0.05). (6C) Hematoxylin and eosin histological sections of murine diabetic wound biopsies taken at days 7, 14 and 28 (D7, D14, D28). By D7 the epidermis and dermis of wounds in the treatment groups (GFP-hWJSCs and hWJSC-CM) showed reepithelialization, formation of sebaceous glands and some hair follicles compared to controls. By D14 and D28, the epidermis of wound biopsies of the treatment arms (GFP-hWJSCs and hWJSC-CM) showed the formation of stratified squamous epithelium and the dermis showed increased cellularity, vasculature and sebaceous gland and hair follicle numbers compared to the controls. E: epidermis; HF: hair follicle; SG: sebaceous gland; S: stroma; SSE: stratified squamous epithelium. Scale bar=100 µm.

Macroscopic digitized images of healing of circular full-thickness murine excisional wounds before and after application of GFP-hWJSCs and hWJSC-CM (treatment arms) and CCD-CM and UCM (controls) showed that wound closure was rapid and completed by day 14 in the treatment arms compared to controls (FIG. 5A). Wound closure rates using a NIH recommended wound healing formula on the digital images showed that the GFP-hWJSCs and hWJSC-CM treatment groups exhibited significantly faster wound closure compared to all control groups (GFP-CCDs, CCD-CM and UCM) on day 7. By day 14 the GFP-hWJSCs treated wounds had healed the fastest (p<0.05) (FIG. 5B). Histological analysis of excisional wound biopsies on days 7 and 14 confirmed the macroscopic and wound closure rate observations. On day 7, the epidermis and dermal layers of wound areas in the treatment groups (GFP-hWJSCs and hWJSC-CM) showed increased reepithelialization, cellularity, and vasculature and increased sebaceous gland and hair follicle numbers compared to controls. On day 14, GFP-hWJSCs and hWJSCCM treated wounds had a thicker epidermis and more sebaceous glands and hair follicles compared to the control groups. Macroscopic observations, wound closure rates and histology confirmed that healing of diabetic wounds was also significantly enhanced in GFP-hWJSCs and hWJSC-CM treated mice compared to controls over a 28 day period (FIGS. 6A, 6B and 6C).

Figure 7:
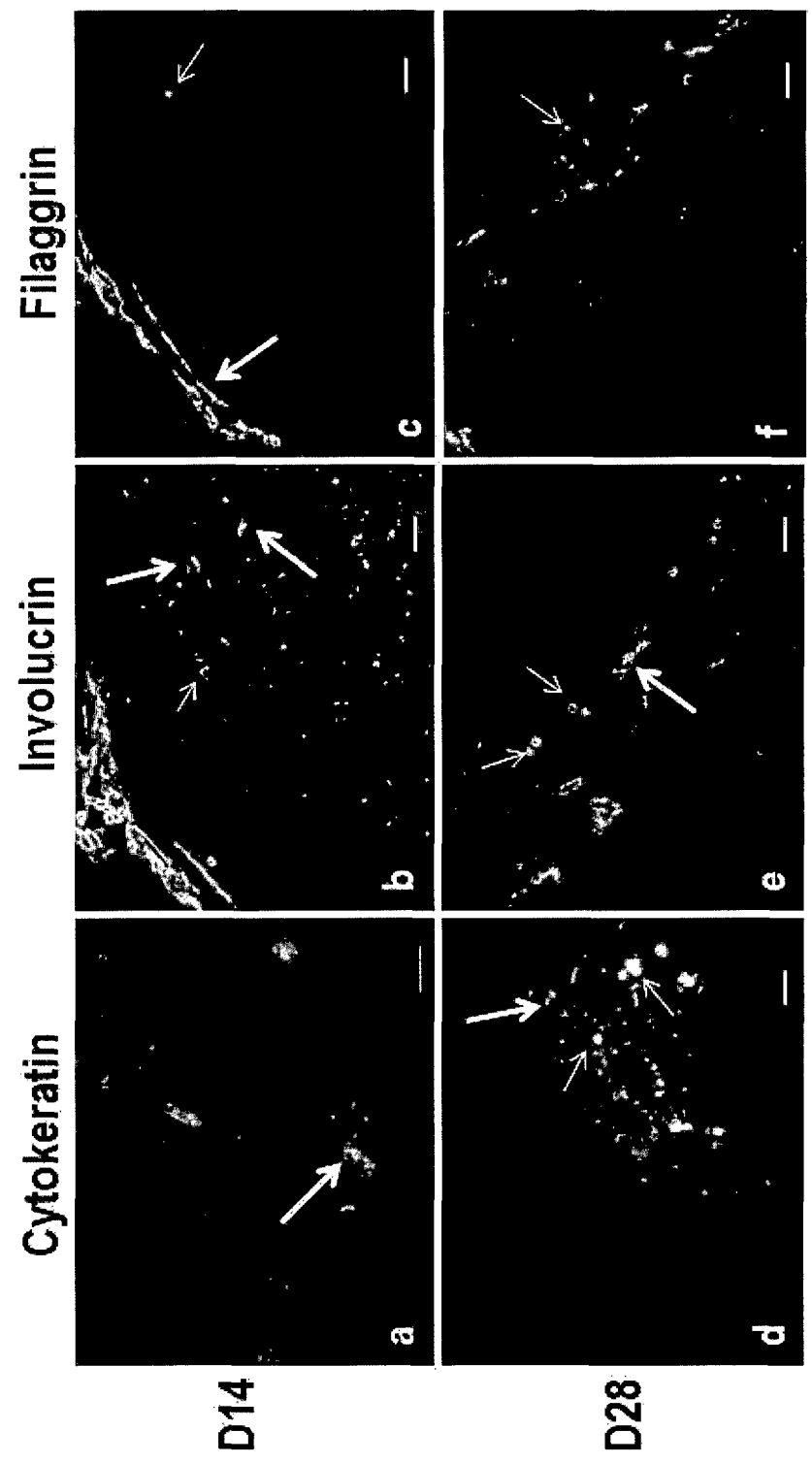
FIG. 7: Fluorescent immunohistochemical images of diabetic mouse wound biopsies on D14 and D28 showing green fluorescent protein (GFP)-labelled hWJSCs (short thin arrows) and positive human keratinocyte markers (red) (thick long arrows). a, d represent cytokeratin clone AE1/AE3; b,e represent involucrin and c,f represent filaggrin DAPI: blue. Scale bar=50 prm.

GFP-hWJSC Survival and Differentiation into Keratinocytes in Murine Excisional and Diabetic Wounds Engraftment and survival of GFP-hWJSCs in the excisional and diabetic wounds at days 7, 14 and 28 were confirmed from green signals via immunofluorescence microscopy (FIG. 7). The number of GFP-hWJSCs in the wound biopsies gradually reduced with wound closure compared to the initial numbers applied to wounds. Immunohistochemistry of excisional and diabetic murine wound biopsies on days 14 and 28 showed the presence of positive human keratinocyte markers (cytokeratin, involucrin and filaggrin) (FIG. 7).

Differential Gene Expression in Excisional and Diabetic Wounds

Figures 8A, 8B:
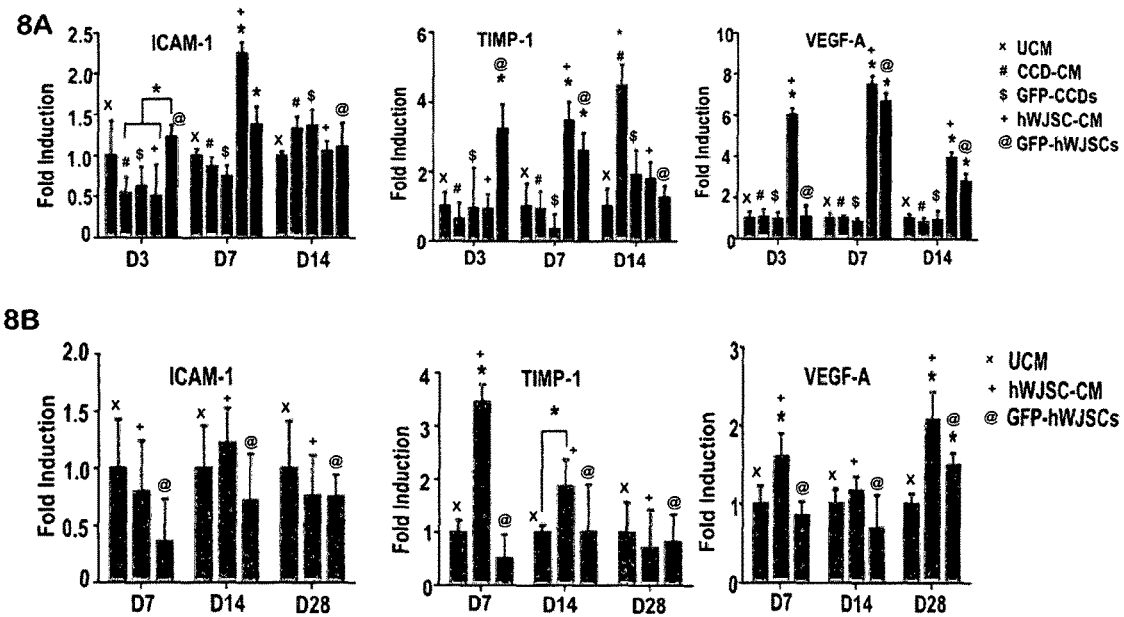
FIGS. 8A-8B: qRT-PCR mRNA expression for mouse ICAM-1, TIMP-1 and VEGF-A using TaqMan probes in (8A) excisional wound biopsies and (8B) diabetic wound biopsies on days 3-28 (D3-D28). (8A) On D3 ICAM-1 mRNA levels in GFP-hWJSC treated excisional wounds were significantly higher than controls (CCD-CM and GFP-CCDs) (*p<0.05). TIMP-1 expression was also significantly upregulated in GFP-hWJSCs treated excisional wounds on D3 compared to controls (*p<0.05). VEGF-A mRNA expression on D3 showed a 6 fold increase in hWJSC-CM treated excisional wounds compared to controls (*p<0.05). On D7, both GFP-hWJSCs and hWJSC-CM treated excisional wounds arms showed significantly greater ICAM-1, TIMP-1 and VEGF-A expression levels compared to controls (*p<0.05). On D14, ICAM-1 levels for excisional wounds were not significantly different between groups but VEGF-A levels were significantly greater in GFP-hWJSCs and hWJSC-CM treated excisional wounds compared to controls (*p<0.05). (8B) For diabetic wounds, the hWJSC-CM treatment arm showed significantly greater levels of TIMP-1 on D7 and D14 and VEGF-A on D7 and D28 compared to controls. VEGF-A levels for the GFP-hWJSCs arm were significantly greater than controls on D28 (*p<0.05).

On day 3 after initiation of wounds, ICAM-1 mRNA levels in excisional wounds in mice treated with GFP-hWJSCs were significantly higher than CCD-CM and GFP-CCDs arms (p<0.05) (FIG. 8A). TIMP-1 expression was also significantly upregulated in excisional wounds on day 3 in the GFP-hWJSCs treatment arm compared to controls (P<0.05) (FIG. 8A). Interestingly, VEGF-A mRNA expression on day 3 showed a 6 fold increase when excisional wounds were exposed to hWJSC-CM (p<0.05) (FIG. 8A). On day 7, both GFP-hWJSCs and hWJSC-CM treatment arms showed significantly greater ICAM-1, TIMP-1 and VEGF-A expression levels compared to controls in excisional wounds (p<0.05). On day 14, the mRNA expression levels of ICAM-1 for excisional wounds were not significantly different between groups but VEGF-A levels remained significantly greater in GFP-hWJSCs and hWJSC-CM treatment arms compared to controls (p<0.05) (FIG. 8A). For diabetic wounds, the hWJSC-CM treatment arm showed significantly greater levels of TIMP-1 on days 7 and 14 and VEGF-A on days 7 and 28 compared to controls. VEGF-A levels for the GFP-hWJSCs arm were significantly greater than controls in diabetic wounds on day 28 (p<0.05) (FIG. 8B).

miRNA Profile in hWJSCs

Among the 487 miRNAs that were found to be differentially regulated between hWJSCs and CCDs, 82 miRNAs were expressed in hWJSCs at significantly higher levels (FDR, p<0.1). Among them only hsa-miR-27a-5p, -98, -181a, -196a-3p, -374a, -601, -622, -920, -3915, and -3924 were found to be upregulated in hWJSCs. The remaining 72 miRNAs were downregulated in hWJSCs compared to CCDs. Nevertheless, several miRNAs that are involved in endothelial function and proliferation processes including wound healing were highly expressed in hWJSCs (Table 2).

Discussion

In the present study the GFP-hWJSCs and hWJSC-CM arms showed significantly greater wound healing compared to controls suggesting that direct and indirect mechanisms of wound healing were taking place by directed differentiation of GFP-hWJSCs into keratinocytes and indirectly by the release of important bioactive molecules that initiate and facilitate the host response to tissue repair. Since the wound biopsies showed the survival of green GFP-hWJSCs signals and species-specific upregulation of human keratinocyte markers (cytokeratin, involucrin and filaggrin), differentiation of the GFP-hWJSCs into new keratinocytes was likely helping reepithelialization in the excisional and diabetic wounds. The results herein show that the introduction of soluble bioactive molecules into wounds via the hWJSC-CM and secretion of the same molecules by the engrafted GFP-hWJSCs creates a niche for the recruitment of native skin MSCs and progenitor cells to the wound site to facilitate healing.

QRT-PCR and species-specific surface marker analysis on wound biopsies in the present study helped to discriminate between the presence of murine and human cells. Based on the upregulation of ICAM-1, TIMP-1 and VEGF-A, it is likely that both hWJSCs and hWJSC-CM modulate differential gene expression in the wounds bringing about cell adhesion, increased angiogenesis and epithelialization during wound healing. VEGF-A is unique for its multiple effects on the wound healing cascade such as angiogenesis, epithelialization and collagen deposition [Bao P, et al, *J Surg Res*, 153:347-358 (2009)]. ICAM-1 is central to the regulation of the inflammatory process during wound healing in the human and mouse [Yukami, T., et al., *J Lec Biol*, 82:519-531 (2007); Gay, A N, et al, *J Surg Res*, 171(1):e1-e7 (2011)] because in the ICAM-1 knockout mouse model there is a delayed response to wound healing [Nagaoka, T et al., *Am J Path*, 157:237-247 (2000)]. Cytokine protein array analysis from our laboratory showed that important cytokines such as ICAM-1, IL-6, IL-8 and TIMP-1 were secreted in large concentrations by hWJSCs in 72 hour hWJSC-CM compared to controls [Fong, C Y, et al., 113:658-668 (2012)]. Such cytokines in the hWJSC-CM thus play a vital role in accelerating wound healing in the early phases. The hWJSCs secretome may help in jumpstarting the wound healing process and subsequent paracrine effects on endogenous mouse cytokine or growth factor secretion. The qRT-PCR results demonstrated that the treatment of hWJSCs to wounds showed increased expression of mouse ICAM-1 and TIMP-1 as early as day 3. Also, ICAM-1 mRNA data on day 14 strongly correlated with the observations of wound closure in vivo and the data indicating that hWJSCs produce adhesion molecules for the acceleration of wound closure during the early phases of wound healing. An increase of TIMP-1 mRNA expression observed on day 14 in CCD-CM treated wounds indicate that the delay in wound healing observed in the CCD-CM treated mice is likely due to the late transcriptional upregulation of TIMP-1. Several published reports have also shown high levels of matrix metalloproteinases (MMPs) and low levels of tissue inhibitors of MMPs (TIMPs) in chronic wound beds indicative of impaired wound healing [Stevens, L J, *Molec Biol of the Cell*, 23:1068-1079 (2012); Liu, Y, et al, *Diab Care*, 32:117-119 (2009)]. MMPs play a major role in wound healing as they can break down all components of the extracellular matrix (ECM) [Stevens, L J, *Molec Biol of the Cell*, 23:1068-1079 (2012)]. In diabetic wounds there are a rise in MMPs and a decrease of TIMPs. High levels of MMP-1 are essential for wound healing while increased levels of MMP-8 and 9 are deleterious. The MMP-1/TIMP-1 ratio was considered a good predictor of healing of diabetic wounds [Muller M, et al., *Diab Med* 25:419-426 (2008)]. It is interesting to note that in the present study excessive levels of secreted TIMP-1 was evident in hWJSC-CM at 72 h and was consistent on a transcriptional level with significant increases in gene expression of fibronectin, collagen I and III indicating that hWJSCs secrete endogenous proteins which affect ECM remodelling.

Collagen is normally produced during the inflammatory phase of wound healing and the ECM secreted by the dermal fibroblasts helps wound remodelling. Fathke et al [Fathke, C et al, *Stem Cells*, 22:812-822 (2004)] demonstrated that MSC populations produce collagen types I and III providing long-term reconstitution of the cutaneous wound. Collagen type III was also reported to be expressed in early healing processes of skin [Zhang, K, et al, *J Invest Dermatol*, 104:750-754 (1995)]. The upregulation of collagen I and III by the CCDs following exposure to hWJSC-CM in the present study also indicates that hWJSC-CM supports wound healing. In the present study hWJSC-CM also stimulated increases in fibronectin and elastin. Fibronectin is another important ECM protein secreted by dermal fibroblasts during the proliferative phase of wound healing [Bielefeld, K A, *J Biol Chem*, 286:27687-27697 (2011)] and is essential in providing the necessary mechanical strength to wounds [Clark, R A F, *J Invest Dermatol*, 94:128S-134S (1990)]. Elastin confers the elasticity and resilience to the skin and these fibres are usually interwoven among collagen bundles. Elastin is also involved in cell signalling and migration in the wound healing process [Rnjak, J et al., *Tissue Engineering, Pat B, Reviews*, 17:81-91 (2011)].

It has been suggested that bioactive molecules released by apoptotic cells stimulate endogenous native and engrafted exogenous MSCs in wounds to initiate the regenerative process of wound healing [Li, F, et al., *Sci Signal*, 3(110) ra13 (2010)]. Caspase 3/7 and prostaglandin E2 (PGE2)

released from damaged apoptotic cells in wounds stimulate the MSCs at the damaged site to proliferate, differentiate and eventually replace the damaged tissue ('Phoenix rising' pathway) [Li, F, et al., Sci Signal, 3(110) ral3 (2010)]. Mice lacking in these caspases were deficient in skin wound healing [Li, F, et al., Sci Signal, 3(110) ral3 (2010)]. More recent evidence confirmed the idea that dying cells signal their presence to the surrounding tissue and in doing so elicit repair and regeneration via stem or progenitor cells that compensate for any loss of function caused by cell death [Jager and Fearnhead, Biochem Res Intl, doi: 1155/2012/453838 (2012)]. These molecules likely play important roles in stimulating the hWJSCs applied to the wounds in the present study to enhance healing.

Specific miRNA clusters (miR-106a-363, miR-17-92, miR-106b-25, miR-302-367 and miR-21) were highly expressed in hWJSCs. The miR-106a-363 and miR-17-92 clusters that were overexpressed are involved in cell proliferation and growth thus likely playing a role in the wound healing process. Functionally, miR-106b-25 promotes cell-cycle progression and hyperproliferation via inhibition of the pro-apoptotic genes such as E2F1, Bim, Fas-activated kinase, CASP7 and PTEN. Combined inhibition of pro-apoptotic genes further provides miR-106b-25-expressing cells with a survival and progression or proliferation benefit. MiR-106b-25 upregulation may lead to enhanced binding to collagen therefore increasing ECM binding. The miR-302-367 cluster targets TGFβ receptor 2 to increase E-cadherin expression and accelerates mesenchymal-to-epithelial transition [Liao, B et al., J Biol Chem, 286:17359-17364 (2011)]. This cluster may be involved in the enhanced reepithelialization in the wounds in the present study. In the normal wound healing process miR-21 is upregulated on day 8 and downregulated in diabetic wounds [Madhyastha, R et al., Intl Wound J, 9:355-361 (2012)]. MiR-21 exhibits a dual function (proliferative and anti-apoptosis) on vascular smooth muscle cells (VSMCs) [Ji R, et al., Circ Res., 100:1579-1588 (2007)]. The role of apoptotic miRNA in promoting tissue regeneration in wound healing was emphasized by Li et al [Li, F, et al., Sci Signal, 3(110) ral3 (2010)] in their 'Phoenix rising' mechanism of wound healing. The VEGF-induced miRNAs (miR-191, -155, -31, -17-5p, -18a and -20a) [Suarez, Y et al., PNAS, USA, 105:14082-14087 (2008)] were also significantly upregulated in hWJSCs compared to CCDs and hBMMSCs. VEGF is an important player in the wound healing process [Bao, P et al., J Surg Res, 153:347-358 (2009)]. Based on the microarray data analysis described herein, besides, the specific miRNAs that have been found to be involved in proliferation, wound healing and pro-angiogenic processes (Table 1), the miR-NAs belonging to the clusters described above were also significantly overexpressed in hWJSCs. Thus, the enhanced wound healing observed in the presence of hWJSCs and hWJSC-CM is likely guided by several miRNAs that provide beneficial effects to the wound healing process.

TABLE 1

The ECM-related genes and primer sequences used for qRT-PCR

| Gene | Primer Sequence |
|---|---|
| GAPDH | F: 5'-GCACCGTCAAGGCTGAGAAC-3' |
|  | R: 5'-GGATCTCGCTCCTGGAAGATG-3' |
| Collagen Type I | F: 5'-CACAGAGGTTTCAGTGGTTTGG-3' |
|  | R: 5'-GCACCAGTAGCACCATCATTTC-3' |
| Collagen Type III | F: 5'-CTGAAATTCTGCCATCCTGAAC-3' |
|  | R: 5'-GGATTGCCGTAGCTAAACTGAA-3' |
| Fibronectin | F: 5'-AAGATTGGAGAGAAGTGGGACC-3' |
|  | R: 5'-GGAGCAAATGGCACCGAGATA-3' |

TABLE 2

Comparison of miRNA expression in hWJSCs and CCDs

| hsa-miRNA | Average fold change | p-value | Function/Implication |
|---|---|---|---|
| let-7a-2-3p | 1.141 | 0.533 | Endothelial |
| let-7d | 1.077 | 0.651 | Endothelial |
| let-7e | 1.269 | 0.474 | endothelial |
| let-7f | 2.061 | 0.453 | endothelial |
| let-7f-1-3p | 1.088 | 0.845 | endothelial |
| let-7g | 1.165 | 0.316 | endothelial |
| let-7i | 1.087 | 0.301 | endothelial |
| let-7i-3p | 1.164 | 0.541 | endothelial |
| miR-100 | 1.125 | 0.499 | endothelial |
| miR-106a | 2.501 | 0.075 | miR-106a-363 |
| miR-106b | 1.241 | 0.31 | miR-106b-25 |
| miR-125a-3p | 1.343 | 0.485 | endothelial |
| miR-125a-5p | 1.078 | 0.819 | endothelial |
| miR-126 | 16.957 | 0.523 | angiomiRs, endothelial |
| miR-146a | 10.998 | 0.514 | wound healing |
| miR-17 | 1.954 | 0.22 | miR-17-92 |
| miR-181a | 2.184 | 0.043 | endothelial |
| miR-18b | 2.567 | 0.062 | miR-106a-363 |
| miR-196a-3p | 1.861 | 0.05 |  |
| miR-19a | 1.771 | 0.157 | miR-17-92 |
| miR-19b | 2.011 | 0.062 | miR-17-92; miR-106a-363 |
| miR-200b | 1.229 | 0.434 | VEGF induced |
| miR-20a | 1.948 | 0.315 | miR-17-92; endothelial; angiomiRs |
| miR-20b | 2.985 | 0.199 | miR-106a-363; angiomiRs |
| miR-21 | 1.717 | 0.264 | endothelial; angiomiRs |
| miR-210 | 1.748 | 0.346 | angiomiRs; VEGF induced |
| miR-25 | 1.359 | 0.519 | miR-106b-25 |
| miR-27a-5p | 3.481 | 0.033 |  |
| miR-29b | 1.114 | 0.854 | pro-apoptotic |
| miR-302a | 1.013 | 0.741 | miR-302-367 |
| miR-302b-5p | 1.423 | 0.61 | miR-302-367 |
| miR-302c-5p | 1.016 | 0.913 | miR-302-367 |
| miR-30c | 1.137 | 0.568 | endothelial |
| miR-31 | 1.078 | 0.822 | endothelial; angiomiRs; VEGF induced |
| miR-32 | 1.343 | 0.684 | miR-25 homolog |
| miR-335 | 22.354 | 0.481 | angiomiRs |
| miR-34a | 1.315 | 0.502 | pro-apoptotic |
| miR-374a | 1.739 | 0.039 |  |
| miR-378 | 1.638 | 0.371 | angiomiRs |
| miR-3915 | 1.8 | 0.019 |  |
| miR-3924 | 1.691 | 0.029 |  |
| miR-601 | 2.882 | 0.044 |  |
| miR-622 | 1.776 | 0.043 |  |
| miR-920 | 4.199 | 0.002 |  |
| miR-92a | 1.556 | 0.372 | miR-17-92 |
| miR-93 | 1.246 | 0.699 | miR-106b-25 |
| miR-98 | 1.515 | 0.006 |  |

Total RNA was extracted from three different hWJSC lines and subjected to miRNA microarray analysis. Fold-change of miRNA expression was calculated with reference to CCD (hWJSC vs CCD). Functional annotations of the respective miRNAs were extracted from the published data.

Example 3

An Aloe Vera-Polycaprolactone Nanoscaffold Impregnated with Human Umbilical Cord Wharton's Jelly Stem Cells or its Conditioned Medium Improves Healing of Excisional and Diabetic Wounds In Vitro and In Vivo Described herein is the use of MSCs from the Wharton's jelly of human umbilical cords (hWJSCs) that have several advantages over hBMMSCs which include painless harvest, availability in large numbers, hypoimmunogenicity, non-tumorigenicity, prolonged sternness properties in vitro and their ability to differentiate into keratinocytes. Since, as shown herein, nanoscaffolds provide three dimensional architectural patterns that mimic in vivo stem cell niches and aloe vera has antibacterial properties, the use of an aloe vera-polycaprolactone (AV/PCL) nanoscaffold impregnated with green fluorescent protein (GFP)-labeled hWJSCs (GFP-hWJSCs+AV/PCL) or its conditioned medium (hWJSC-CM+AV/PCL) was evaluated for healing of excisional and diabetic wounds in vitro and in vivo. In scratch-wound assays, skin fibroblasts migrated significantly faster from the edges of the wounds into the wounds together with increased secretion of collagen I and III, elastin, fibronectin, superoxide dismutase and metalloproteinase-1 (MMP-1) when exposed to GFP-hWJSCs+AV/PCL and hWJSC-CM+AV/PCL compared to controls. With one application of GFP-hWJSCs+AV/PCL or hWJSC-CM+AV/PCL, murine excisional and diabetic wounds showed faster wound closure, reepithelialization, formation of stratified squamous epithelium and increased numbers of sebaceous glands and hair follicles compared to controls. Excisional and diabetic wounds exposed to GFP-hWJSCs+AV/PCL or hWJSC-CM+AV/IPCL also showed positive keratinocyte markers (cytokeratin, involucrin, filaggrin) and expression of ICAM-1, TIMP-1 and VEGF-A compared to controls. The results described herein show that wound healing was via bioactive soluble molecules secreted by the hWJSCs. AV/PCL nanoscaffolds in combination with hWJSCs appear to have synergistic benefits for wound healing.

Described herein is the evaluation of a wound dressing patch made up of an aloe vera-PCL (AV/PCL) nanoscaffold impregnated with hWJSCs or its conditioned medium (hWJSC-CM) for healing of excisional and diabetic wounds in in vitro and animal studies.

Materials and Methods

Cell Culture and Preparation of Conditioned Media

Ethical approval for the use of discarded human umbilical cords for this study was given by the Institutional Domain Specific Review Board (DSRB), Singapore. hWJSCs were derived and characterized according to published protocols [Fong Fong et al, *Reprod Biomed online*, 15:708 (2007); Fong C Y, et at, *Reprod Biomed Online*, 21:391 (2010)]. Human foreskin fibroblasts (CCD-112sk) (abbreviated as CCD) were obtained from the American Type Culture Collection (ATCC, MD) to act as controls and ethical approval for their use was given by the National University of Singapore Institutional Review Board (NUS-IRB). hWJSCs and CCDs were transfected with a lentiviral vector for green fluorescence protein (GFP-hWJSCs, GFP-CCDs) for cell identification and tracking purposes. GFP-hWJSCs and GFP-CCDs (passages 3-4) were grown in a serum-free knock-out basal medium supplemented with/without serum replacement substitute (KOSR medium) to avoid contamination by serum proteins. After 72 h the conditioned media (hWJSC-CM, CCD-CM) were separated, sterilized with a 0.22 µm filter (Millipore, Billerica, Mass.) and diluted with basal medium with/without KOSR to 50%.

Fabrication and Characterization of AV/PCL Nanoscaffold

Polycaprolactone (PCL) (MW: 80,000) (Sigma-Aldrich, Mo.) and aloe vera freeze dried powder (Zhang Peng International, Singapore) were dissolved (10% PCL:5% aloe vera) in chloroform:methanol (3:1) (Sigma-Aldrich, Mo.) by stirring over 24 h. To prepare topographically randomized nanoscaffolds, the aloe vera-PCL mixture was electrospun after feeding into a 3 ml syringe attached to a 18G blunt stainless steel needle and using a syringe pump at a flow rate of 3.0 ml/h with an applied voltage of 25 kV (Nanon, Mecc, Japan). The nanofibers were collected and spread at 23° C. and 45% humidity from a rotating drum on to 15 mm cover slips. The mean±SEM diameter of the nanofibers was calculated using scanning electron microscopy (SEM). Nanoscaffolds were vacuum-dried and sterilized before use.

Preparation of Wound Dressing Patches

Figure 9:
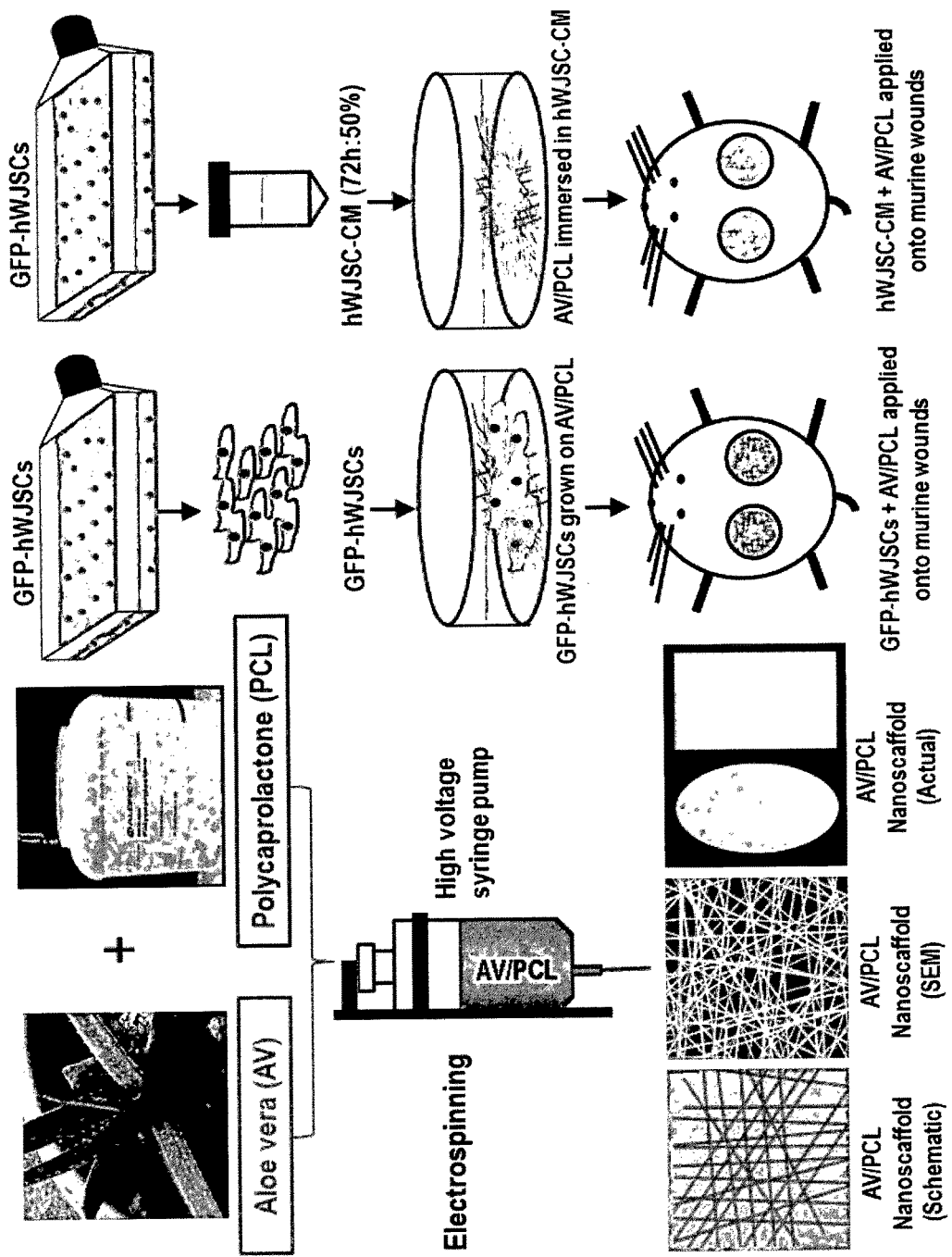
FIG. 9: Schematic diagram showing preparation of wound dressing patch. AV/PCL nanoscaffolds were prepared by electrospinning and the impregnated with either GFP-hWJSCs or hWJSC-CM.

Wound dressing patches were made by seeding sterile nanoscaffolds with GFP-hWJSCs or GFP-CCDs ($5\times10^5$ cells) followed by incubation for 72 h at 37° C. in a 5% $CO_2$ in air atmosphere (FIG. 9). They were then examined under confocal microscopy (Olympus FV 1000) to ensure that the cells had attached and migrated into the nanoscaffolds. The patches were photographed and z-stack images compiled to provide 3D images. Separately, nanoscaffolds were impregnated with hWJSC-CM or CCD-CM over 72 h (FIG. 9).

In Vitro Studies

Scratch-Wound Assays

The conventional scratch-wound assay of Cory (2011) for wound healing was adopted [Cory G, *Meth Mol Biol*, 769:25 (2011)]. Firstly, CCDs were cultured on 0.1% gelatin-coated 60 mm Petri dishes (Nalgene NUNC International, Rochester) in KOSR medium at 37° C. in a 5% $CO_2$ in air atmosphere for 24 h to produce confluent monolayers. Linear scratches (0.5 mm width) to mimic wounds were made vertically from top to bottom along the midline of the confluent CCD monolayer using a sterile pipette. The spent KOSR culture medium from the Petri dish was then removed together with the detached CCD cells. Nanoscaffolds that were pre-soaked in hWJSC-CM, or CCD-CM, or unconditioned KOSR medium were then placed over the respective wounds. Each Petri dish was then filled with 2 ml of its respective culture medium as follows: (i) hWJSC-CM+AV/PCL (treatment arm); (ii) CCD-CM+AV/PCL (control) and (iii) Unconditioned KOSR medium (UCM)+AVIPCL (control). Treatment and control dishes were then incubated at 37° C. in a 5% $CO_2$ in air atmosphere for 72 h. Three replicates were carried out for each assay. CCD migration from the edges of the wounds into the vacant areas was monitored regularly and digitized images of at least 5 random fields within the wounds were taken every 24 h using inverted phase contrast optics for 72 h or until full closure of the wounds. Markings on the Petri dishes were used as reference points to monitor the same fields every 24 h. The mean±SEM percentage extent of closure of the wounds at 24, 48 and 72 h were calculated from the digitized images using an image software program [Walter, M N, et al., *Exp Cell Res*, 316:1271 (2010)]. The number of viable CCDs in the scratch wounds was measured using the MTT assay to find out whether the respective treatments had stimulated CCD proliferation and survival in addition to migration. The MTT assay was carried out using a MTT reagent kit [3-(4,5-dimethylthiazolyl-2)-2,5-diphenyltetrazolium bromide](Sigma, St. Louis, Mo.) according to the manufacturer's instructions. Absorbance at 570 nm was spectrophotometrically measured using a microplate ELISA reader (ptQuant-BioTek, Winooski, Vt.) with a reference wavelength of 630 nm.

Collagen, Elastin, Superoxide Dismutase (SOD) and qRT-PCR Analysis

Total collagen, elastin and SOD levels in treatment and control dishes were evaluated using Sircol™, Fastin™ (Biocolor, Carrickfergus) and SOD (Sigma) kits respectively according to the manufacturer's instructions. The CCDs of treatment and control dishes were also subjected to conventional qRT-PCR using SYBR green and the ABI PRISM 7500 Fast Real-Time PCR System (Applied Biosystems, Foster City, Calif.) and relative quantification was performed using the comparative CT (2-AACT) method. Primer sequences were taken from earlier published studies and are shown in Table 3.

Animal Studies
Excisional and Diabetic Wound Healing Models

Approval for all animal procedures was given by the Institutional Animal Care and Use Committee (IACUC) of the National University of Singapore. For the excisional wound study, female severely combined immunodeficient (SCID) mice (5-6 weeks) (Animal Resources Centre, Western Australia) were shaved after isofluorane anesthesia and two circular punch biopsy (Accusharp punch, India) full-thickness wounds (8 mm diameter) were created on the left and right dorsal regions. Fifty-four mice (108 wounds) were divided into 6 groups [9 mice (18 wounds) per group] and the wounds in each group treated as follows [Gp 1 (Treatment): GFP-hWJSCs ($1 \times 10^6$ cells)+AV/PCL; Gp 2 (Treatment): hWJSC-CM (100 µl)+AV/PCL; Gp 3 (Control): GFP-CCDs ($1 \times 10^6$ cells)+AV/PCL; Gp 4 (Control): CCD-CM (100 µl)+AV/PCL; Gp 5 (Control): PBS (100 µl)+AV/PCL and Gp 6 (Control): Untreated (No AV/PCL)]. The wounds of all 6 groups were covered with Tegaderm (3M) and the edges sealed with Dermabond™ (Ethicon) to prevent the animals from removing the Tegaderm. The animals were individually housed under a 12:12 h light-dark cycle under SPF conditions.

For the diabetic wound study, similar full-thickness circular (6 mm diameter) wounds were created on the shaved dorsal regions (left and right) of diabetic mice (Strain BKS.Cg-Dock7m+/+Leprdb/J; Stock No: 000642 resembling Type IIDM) (The Jackson Laboratory, Bar Harbor). A smaller sized wound punch was chosen to mimic other published murine diabetic wound studies [Wu Y, et al., Stem Cells, 25:2648 (2007); Sullivan S R, et al., Plast Reconstr Surg, 113:953 (2004)]. Glucose levels were measured before and after the experiment to confirm that the mice were diabetic. A total of 36 mice (72 wounds) were divided into 3 groups [12 mice per group (24 wounds)] and the wounds in each group treated as follows: [Gp 1 (Treatment): GFP-hWJSCs ($1 \times 10^6$ cells)+AV/PCL; Gp 2 (Treatment): hWJSC-CM (100 µl)+AV/PCL; Gp 3 (Control): UCM (100 µl)+AV/PCL]. Four mice from each group were randomly sacrificed on days 7, 14 and 28 for wound healing analysis.

Digitized photographs were taken on days 0, 7 and 14 for excisional and on days 0, 14 and 28 for diabetic wounds. Healing rates until wound closure were calculated from the digitized images using a NIH recommended formula and image software (original wound area−new wound area)/original wound area×100) [Chen L, et al., PLoS ONe, 4:e7119 (2009)] by two independent observers blinded to treatments.

At specific time points, wound biopsies were collected and frozen for fluorescent microscopy for the presence and survival of green-labelled hWJSCs or CCDs and for immunohistochemistry of human keratinocyte markers (filaggrin, involucrin and cytokeratin) using mouse monoclonal anti-human filaggrin (Abcam, Cambridge), anti-human involucrin (Genway, San Diego) and anti-human cytokeratin (clone AE1/AE3) (Dako, Carpinteria, Calif.). Biopsies were also fixed in 10% buffered formalin for histology and snap-frozen in liquid nitrogen for genomic and molecular analysis.

Quantitative Real-Time PCR of Wound Biopsies

The mRNA expression of ICAM-1, TIMP-1 and VEGF-A in wound biopsies was examined using the TaqMan qRT-PCR protocol. Briefly, wound biopsies were homogenized using the TissueLyser LT (Qiagen, Valencia, Calif.) machine. Total RNA was then extracted using the EZI RNA Universal tissues kit (Qiagen) and reverse transcribed using a high capacity cDNA Reverse Transcription Kit (Applied Biosystems, Carlsbad, Calif.). TaqMan Fast Advance Mastermix (Applied Biosystems) was used for quantification of cytokine release and VEGF expression (TIMP-1: Mm00441818_m1, ICAM-1: Mm00516023_m1 and VEGF-A: Mm01281449_m1) respectively. All TaqMan Gene Expression Assays were performed against the endogenous reference gene GAPDH: Mm99999915_g1.

Statistical Analysis

The results of in vitro studies were expressed as mean±SEM from three different replicates for individual assays and the differences between treatments and controls were compared using Students t-test. For in vivo analyses, the mean±SEM percentages of wound closure were analyzed by ANOVA and post-hoc test with Tukey's Honestly Significant Difference (HSD). A p value of <0.05 was regarded as statistically significant. Statistical significance was determined using SPSS software, version 13.0 (SPSS, Chicago, Ill.).

Results
Interaction of AV/PCL and hWJSCs

Figures 10A, 10B, 10C, 10D, 10E, 10F:
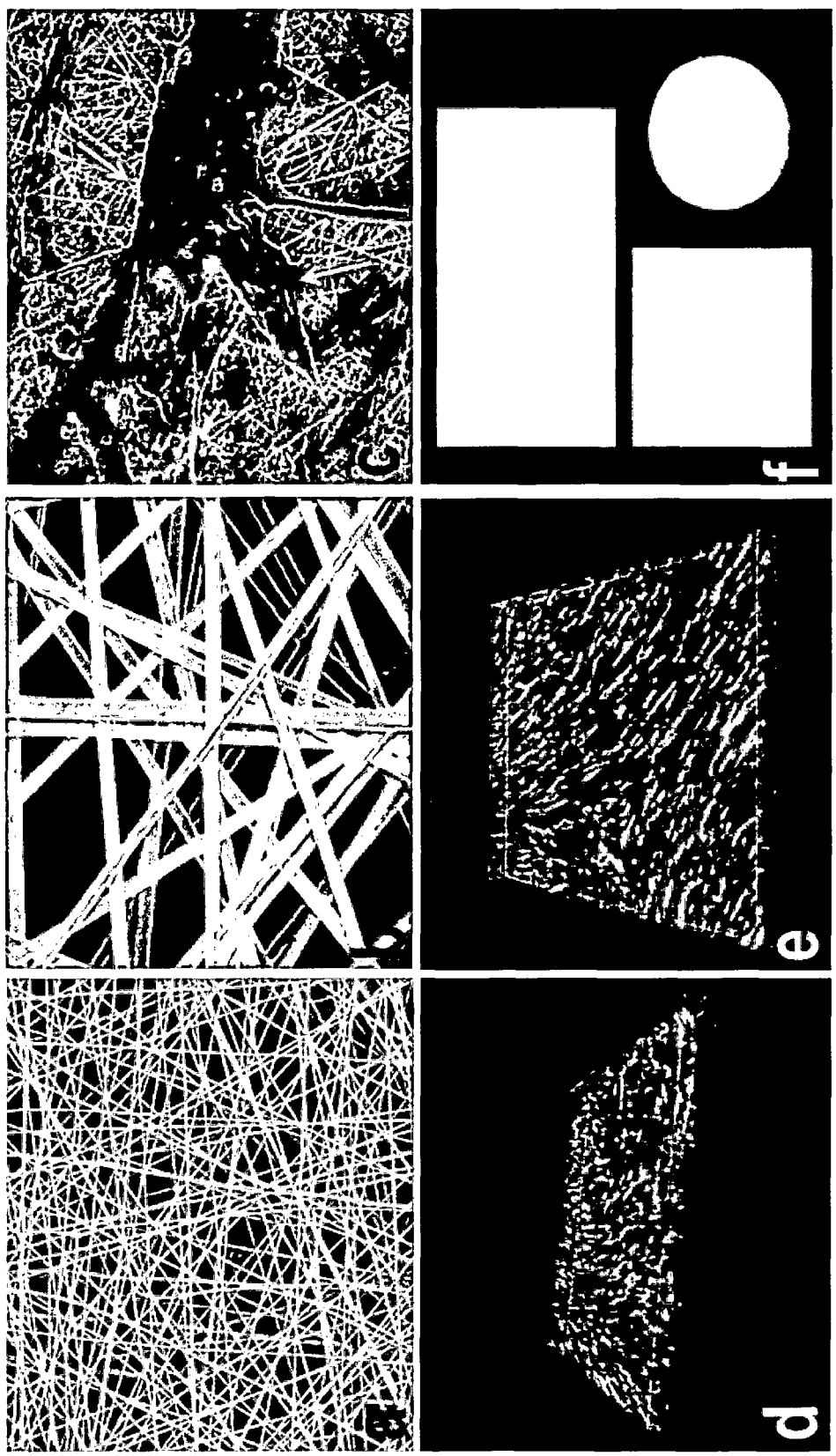
FIGS. 10A-10F: (10A, 10B) Low and high magnification scanning electron micrographs of AV/PCL randomly aligned nanofibers showing pores and niches (2500×; 15,000×). (10C): Scanning electron micrograph showing hWJSCs attached and growing on nanofibers (2500×). (10D, 10E): Confocal fluorescent images of side and surface views of AV/PCL nanoscaffolds impregnated with GFP-hWJSCs after 72 h. Note GFP-hWJSCs growing into nanoscaffold. (10F): Final actual wound dressing patches of different shapes.

Scanning electron micrographs showed that AV/PCL nanofibers electrospun on a rotating drum in our laboratories yielded a randomized mesh-like topography with mean±SEM fiber diameters of 448±65 nm, thickness of 0.5 mm and 90% porosity (FIG. 10A, 10B). There were adequate niches for the hWJSCs to attach, migrate and grow (FIG. 10C). Compilation of z-stack images via confocal laser microscopic imaging showed that after 48-72 h in culture GFP-hWJSCs were able to migrate into a depth of 51.3 µm into the nanoscaffold (FIG. 10D, 10E). The nanoscaffolds could be fabricated into different shapes for different sized wounds (FIG. 10F).

Scratch-Wound Assay

Figures 11A, 11B, 11C, 11D, 11E, 11F, 11G, 11H, 11I:
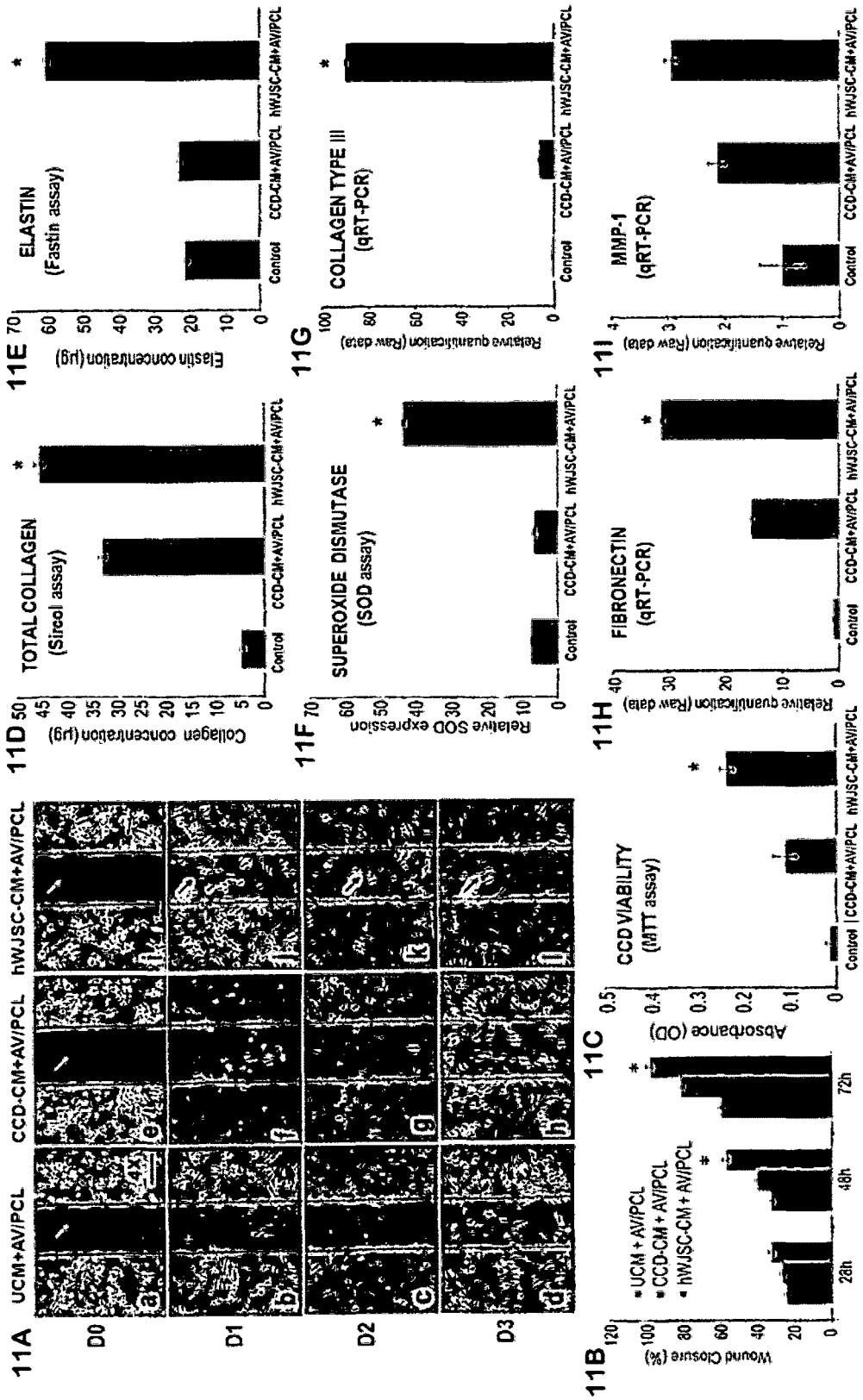
FIGS. 11A-11I: (11A) Scratch-wound assays of CCD fibroblasts (72 h; D0-D3) exposed to hWJSC-CM+AV/PCL (Treatment), CCD-CM+AV/PCL (Control) and UCM+AV/PCL (Control). a-i: Note vacant linear scratches (wounds) with no cells (white arrows) in treatment and controls assays on D0. b-j: Note CCDs migrating from edges of wounds into vacant areas on D1 with greatest migration in hWJSC-CM+AV/PCL treatment group (black arrow). c-k and d-l: Note faster migration of CCDs on D2 and D3 in hWJSC-CM+AV/PCL treatment group with wounds fully covered by D2 and D3 compared to controls. (11B) Histogram showing that mean±SEM wound closure percentages were significantly greater in the hWJSC-CM+AV/PCL treatment group compared to controls (p<0.05). (11C, 11D, 11E, 11F) Histogram showing that cell viability, total collagen, elastin and SOD concentrations in scratch-wound assays were significantly greater in the hWJSC-CM+AV/PCL treatment group compared to controls (p<0.05). (11G, 11H, 11I) Histogram showing that the qRT-PCR cDNA expression levels of collagen III and fibronectin in scratch-wound assays were significantly greater in the hWJSC-CM+AV/PCL treatment groups compared to controls (p<0.05) while MMP-1 although greater were no significantly different from controls.

CCDs started to migrate from the edges of the wounds into the vacant areas as early as 6-8 h in treatment and control dishes (FIG. 11A). Cell migration was more pronounced and the wounds were completely covered by 48-72 h in the hWJSC-CM+AV/PCL treatment arm compared to controls (FIG. 11A). Wound closure rates (mean±SEM %) were significantly greater in the hWJSC-CM+AV/PCL treatment arm compared to controls (p<0.05) (FIG. 11B). The actual mean±SEM CCD numbers that migrated into the scratch areas for hWJSC-CM+AV/PCL (treatment), CCD-CM+AV/PCL (control) and UCM+AV/PCL (control) as determined by two independent observers were (24 h): 22±02, 19±02, 17±02; (48 h): 58±05, 32±02, 33±03; (72 h): 322±04, 255±04 and 158±05 respectively. The viability of CCDs (MTT assay) from the hWJSC-CM+AV/PCL treatment arm was significantly greater than the controls (FIG. 11IC).

The secreted total collagen, elastin and SOD concentration levels in scratch-wound assays were significantly greater in the treatment group (hWJSC-CM+AV/PCL) compared to the controls (p<0.05) (FIG. 11D, 11E, 11F).

CCDs of scratch-wound assays in the treatment arm (hWJSC-CM+AV/PCL) showed significantly greater expression of collagen III and fibronectin compared to controls (p<0.05) with 90- and 31-fold increases respectively (FIG. 11G, 11H). Although MMP-1 expression was increased for the hWJSC-CM+AV/PCL treatment arm, the increase was not significantly different from controls (FIG. 11).

Wound Healing In Vivo

Figures 12A, 12B:
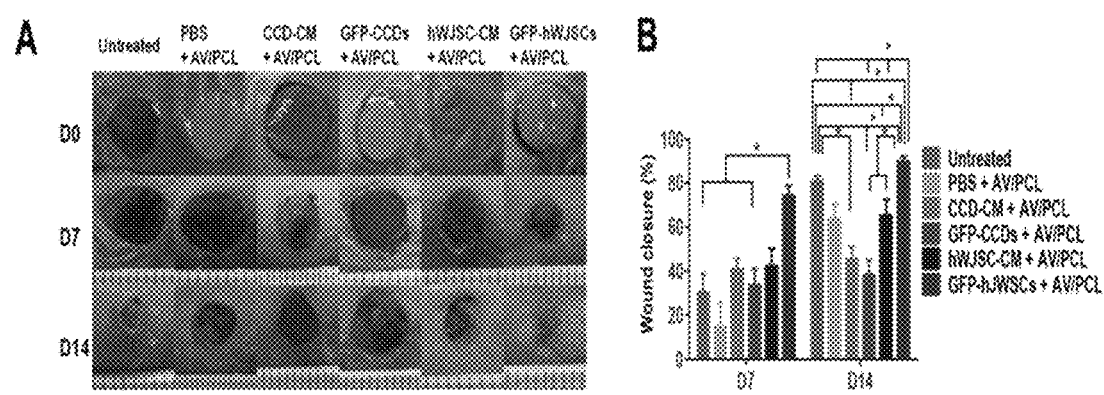
FIGS. 12A-12B: (12A) Digitized images of excisional wounds in SCID mice showed faster wound closure by day 7 in the GFP-hWJSCs+AV/PCL treatment arm compared to all other arms. (12B) Mean±SEM percentage wound closure rates in SCID mice were significantly faster in the GFP-hWJSCs+AV/PCL arm compared to controls on day 7 (p<0.05). On day 14, wound closure rates were significantly greater in the GFP-hWJSCs+AV/PCL and hWJSC-CM+AV/PCL arms compared to controls (p<0.05).

A comparison of macroscopic digitized images of excisional wounds between treatment and control groups are shown in FIG. 12A. Close monitoring of wound closure by two independent observers showed rapid wound closure by day 14 in the hWJSCs+AV/PCL and hWJSC-CM+AV/PCL arms compared to controls (FIG. 12A). Mean±SEM percentage wound closure rates as determined by the wound healing formula on digitized images [Chen L, et al., PLoS ONe, 4:e7119 (2009)] showed that the hWJSCs+AV/PCL and hWJSC-CM+AV/PCL treatment arms exhibited faster wound closure compared to controls on day 7 with the closure rates for the hWJSCs+AV/PCL arm being significantly different from controls (p<0.05). On day 14, the rate of wound closure was significantly greater in the hWJSCs+AV/PCL treatment arm compared to all other arms (FIG. 12B). On day 3, histological examination of wound biopsies in treatment groups demonstrated increased granulation and reepithelialization and appearance of a few sebaceous glands and hair follicles. On the other hand, the wound biopsies of controls showed disrupted epithelium, infiltration of leukocytes, lymphocytes and fibroblasts in the dermis and the wound surfaces were covered with blood, fibrin and exudates (FIG. 12C). On days 7 and 14, the epidermis of wounds in the treatment arms (GFPhWJSCs+AV/PCL and hWJSC-CM+AV/PCL) showed the formation of stratified squamous epithelium, increased numbers of sebaceous glands and hair follicles and greater cellularity and vasculature compared to controls.

Figures 13A, 13B, 13C:
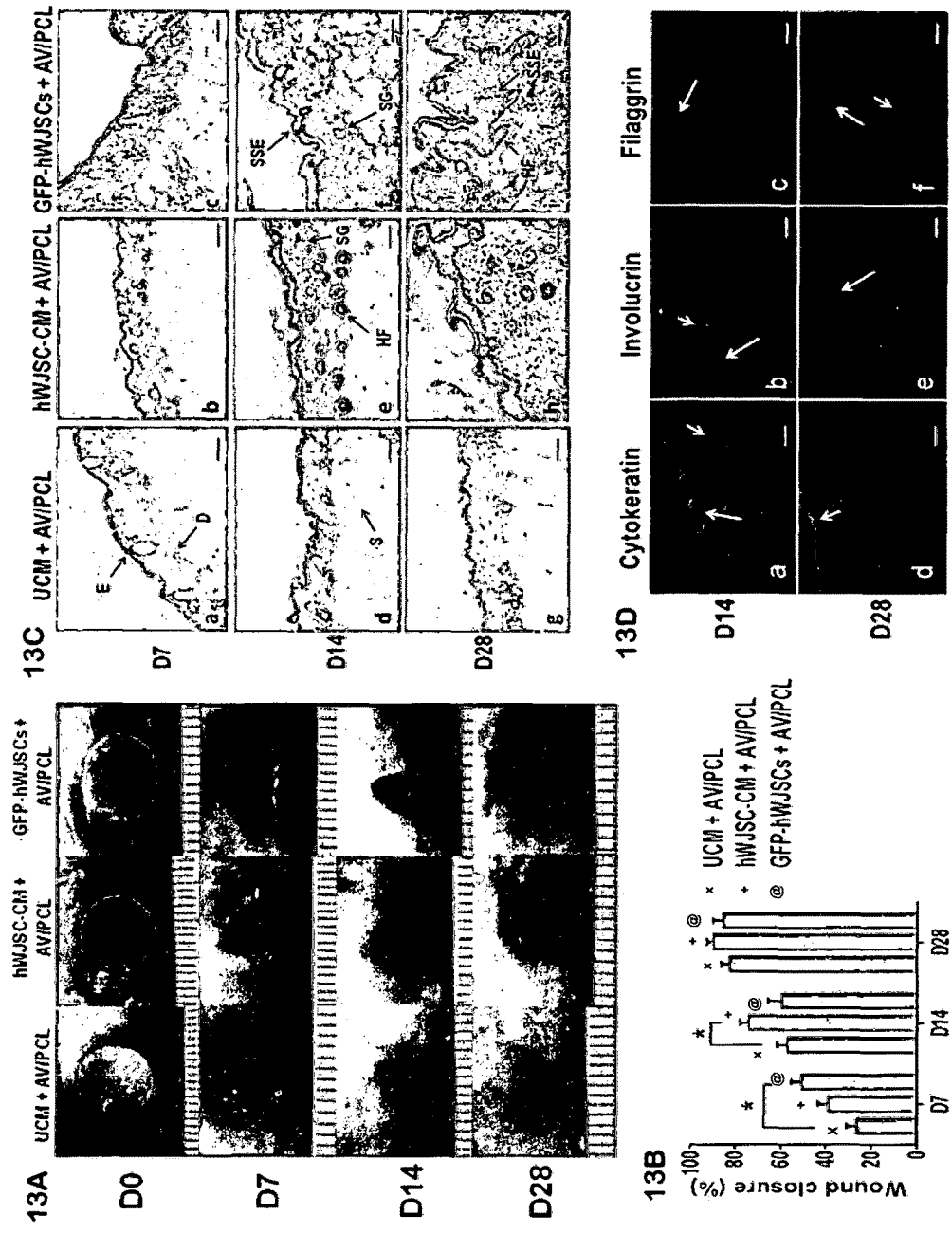

A comparison of macroscopic digitized images and wound closure rates of diabetic wounds between treatment and control groups are shown in FIG. 13A, 13B. The GFP-hWJSCs+AV/PCL and hWJSC-CM+AV/PCL treated mice showed complete wound closure of diabetic wounds compared to UCM+AV/PCL (control) by day 28 (FIG. 13A). On day 7, the mean±SEM percentage rate of wound closure of the GFP-hWJSCs+AV/PCL treatment arm was significantly greater than the controls and on day 14 the wound closure rates of the hWJSC-CM+AV/PCL treatment group was significantly greater than the controls (p<0.05) (FIG. 13B). On day 7, histological examination of the diabetic wound biopsies showed reepithelialization, a few sebaceous glands and some hair follicles in the treatment groups compared to the controls. On days 14 and 28 the treatment groups (GFP-hWJSCs+AV/PCL and hWJSC-CM+AV/PCL) showed the formation of stratified squamous epithelium, increased cellularity and vasculature and increased sebaceous gland and hair follicle numbers compared to controls. On day 28 the diabetic wounds of controls not receiving any treatment had no stratified squamous epithelium, only a few sebaceous glands and hair follicles and as such did not display the typical normal skin phenotype (FIG. 13C). Immunofluorescence staining of cytokeratin, involucrin and filaggrin which are markers of epidermal differentiation [Kawachi Y et al., Eur J Dermatol, 21:1016 (2011)] are shown in FIG. 13D. Positive staining for cytokeratin was present on days 14 and 28 in db/db mice (FIG. 13D, a, d: short arrows). Involucrin, a marker for epidermal late-stage differentiation was evident on day 14 (FIG. 13D, b: short arrow) and filaggrin, a marker for terminally differentiated granular layer keratinocytes was present on day 28 (FIG. 13D, f: short arrow).

Differential Gene Expression in Excisional and Diabetic Wounds

Figures 14A, 14B:
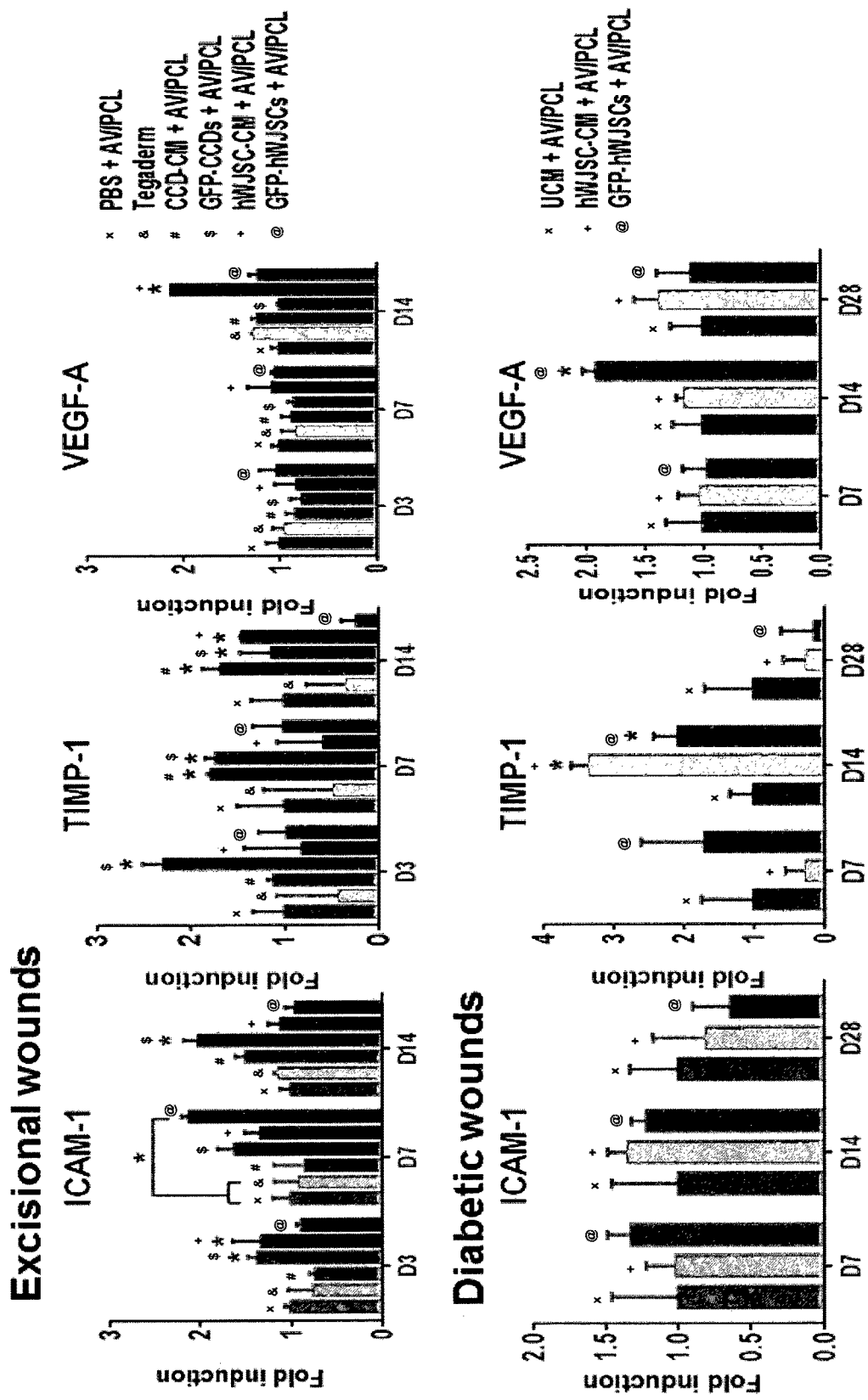
FIGS. 14A-14B: (14A) On day 7, ICAM-1 mRNA levels in excisional wounds of mice treated with GFP-hWJSCs+ AV/PCL were significantly higher than controls while TIMP-1 and VEGF-A expression for the hWJSC-CM+AV/IPCL treatment arm was significantly higher than all other groups on day 14 (p<0.05). (14B) For diabetic wounds, the TIMP-1 levels for both the treatment groups (GFP-hWJSCs+AV/PCL and hWJSC-CM+AV/PCL) were significantly higher on day 14 compared to other groups while VEGF-A expression was significantly higher only for the GFP-hWJSCs+AV/PCL treatment group compared to other groups on day 14 (p<0.05).

ICAM-1 mRNA levels in excisional wounds in mice treated with GFP-hWJSCs+AV/PCL were significantly higher than controls on day 7 while TIMP-1 and VEGF-A expression for the hWJSC-CM+AV/PCL group was significantly higher than all other groups on day 14 (p<0.05) (FIG. 14A). For diabetic wounds, the TIMP-1 levels for both the treatment groups (GFP-hWJSCs+AV/PCL and hWJSC-CM+AV/PCL) were significantly higher on day 14 compared to other groups while VEGF-A expression however was significantly higher only for the GFP-hWJSCs+AV/PCL treatment group compared to other groups on day 14 (p<0.05) (FIG. 14B).

Discussion

Shown herein are the benefits of an AV/PCL nanoscaffold impregnated with hWJSCs or its conditioned medium as novel dry or wet wound dressings for surgical and diabetic wounds. Since cells perform best in the presence of three dimensional cues, the enhanced efficiency of wound healing in the two treatment groups (hWJSCs+AV/PCL and hWJSC-CM+AV/PCL) of the present study are likely attributed to the synergistic effect of stem cells and nanoscaffold where the nanoscaffold provided the stem cell niches and porosity for the hWJSCs to attach, differentiate and allow its secretions to penetrate into the wound beds.

Since both the hWJSCs and its conditioned medium showed significantly better wound healing over controls, cell-to-cell contact and non-cellular contact mechanisms (via the release of important molecules) likely have facilitated the wound healing process.

In preliminary studies it was observed that specific miRNA clusters (miR-106a-363, miR-17-92, miR-106b-25, miR-302-367 and miR-21) were highly expressed in hWJSCs compared to hBMMSCs. The miR-106a-363 and miR-17-92 clusters are involved in cell proliferation and growth thus playing a role in the wound healing process. MiR-106b-25 upregulation leads to increased binding to collagen and the ECM while miR-302-367 is known to target TGF3 receptor 2 to encourage E-cadherin expression and promote mesenchymal-to-epithelial transition for improved reepithelialization [Liao B, et al., J Biol Chem, 286:17359 (2011)]. Madhyastha and colleagues [Madhyastha R et al, Int Wound J, 9:355 (2012)]showed that miR-21 is upregulated on day 8 in the normal wound healing process and Ji et al. demonstrated that it exhibits proliferative and anti-apoptosis properties on vascular smooth muscle cells thus enhancing angiogenesis for better wound healing [Ji R et al., Circ Res 100:1579 (2007)]. The gene expression profiles of wound biopsies in the present study showed the upregulation of VEGF-A. Interestingly, the pilot studies showed that the VEGF-induced miRNAs (miR-191, -155, -31, -17-5p, -18a and -20a) were significantly upregulated in hWJSCs compared to CCDs and hBMMSCs. It is also well-known that VEGF is an important player in the wound healing process [Bao, P et al., J Surg Res, 153:347 (2009)].

ICAM-1 is central to the regulation of the inflammatory process during wound healing in the human and mouse and assists in cell adhesion of the ECM. Impaired wound healing is also associated with high levels of matrix metalloproteinases (MMPs) and low levels of the tissue inhibitors of MMPs (TIMPs) in chronic wound beds [Liu Y et al., Diab Care, 32:117 (2009); Stevens L J et al., Mol Biol Cell, 23:1068 (2012)]. It is interesting to note that in the present study the high levels of TIMP-1 in hWJSC-CM may have reversed the MMP/TIMP ratio thus facilitating wound healing and this is synergistic at a transcriptional level with the increases in gene expression of fibronectin, collagen I and III indicating that hWJSCs release proteins which affect ECM remodeling.

Fibroblasts in wounds modulate fibroblast-keratinocyte-endothelium interaction through the production of the ECM and cytokines [Jeon Y K et al., *Wound Repair Reg,* 18:655 (2010)] and shown herein is that hWJSCs release a variety of cytokines of the interleukin family [Fong C Y, et al., *Stem cell rev,* 7:1 (2011)]. The ECM is comprised of fibronectin that provides fibroblast migration, and collagen and elastin that provide tissue strength and resiliency. These three proteins were produced in high concentrations in the present study which indicates their contribution. to the wound healing process.

The results provided herein show that WJSCs (e.g., hWJSCs) and extracts thereof are a better substitute for human bone marrow mesenchymal stem cells (hBMMSCs) for wound healing given the several advantages described herein. Moreover, inclusion of a nanoscaffold provides for synergistic benefits as wound dressings for slow healing and hard-to-heal chronic wounds.

TABLE 3

Primer sequences used for quantitative reverse transcription-PCR gene expression analysis

| Gene | Primer Sequence |
| --- | --- |
| Collagen III | F: 5'-CTGAAATTCTGCCATCCTGAAC-3'<br>R: 5'-GGATTGCCGTAGCTAAACTGAA-3' |
| Fibronectin | F: 5'-AAGATTGGAGAGAAGTGGGACC-3'<br>R: 5'-GAGCAAATGGCACCGAGATA-3' |
| MMP-I | F: 5'-TTGAGAAAGCCTTCCAACTCTG-3'<br>R: 5'-CCGCAACACGATGTAAGTTGTA-3' |
| GAPDH | F: 5'-GCACCGTCAAGGCTGAGAAC-3'<br>R: 5'-GGATCTCGCTCCTGGAAGATG-3' |

MMP: Matrix metalloproteinase;
GAPDH: Glyceraldehyde-3-phosphate dehydrogenase.

Example 4

Human Wharton's Jelly Stem Cells and Its Extracts Inhibit the Growth of Human Keloid Cells Keloids are firm rubbery growths that grow beyond the boundaries of human wounds. They are a psycho-social burden to patients and current treatments have had limited success. A benign tumor-like mesenchymal stem cell (MSC) phenotype driving uncontrolled cell proliferation has been suggested for its pathogenesis. As described herein, the role of hWJSCs, its conditioned medium (hWJSC-CM) and lysate (hWJSC-CL) on the inhibition of keloid cell growth in vitro and in vivo was explored. Keloid cells readily grew in adherent and sphere culture and showed upregulation of the typical MSC-CD markers CD29, CD44, CD73, CD90 and CD105. When they were exposed to hWJSC-CM and hWJSC-CL their in vitro growth and CD marker levels reduced significantly indicating a loss of sternness properties. The treated keloid cells also showed significant reduction of cell viability (MTT), increases in Annexin, V-FITC and TUNEL-positive cells, interruption of cell cycle at sub-G1 phase and migration inhibition in scratch-wound assays. Immunohistochemistry showed significant reduction in tumor-associated fibroblast (TAF) and increase in autophagy-related markers (BECLIN-1 and LC3B). qRT-PCR showed downregulation of anti-apoptotic-related genes (BCL2, and SURVIVIN) and upregulation of pro-apoptotic and autophagy-related genes (BAX, ATG5, ATG7, and BECLIN-1). A successful human xenograft keloid mouse model was developed and subcutaneous administration of a single dose of hWJSCs with keloid cells and matrigel did not result in keloid tumors in all eight injection sites of four mice. The results indicate that hWJSCs or molecules secreted by them are of therapeutic value in the treatment of keloids.

Materials and Methods

Cell Culture

Human Wharton's Jelly Stem Cells

Ethical approval for the use of human umbilical cords from consenting patients was given by the Institutional Domain Specific Review Board (DSRB), Singapore. hWJSCs were derived and characterized according to our published protocols (Fong et al. *Reprod Biomed Online,* 21:391-401, 2010). Umbilical cords were collected in a transport medium (Hank's Balanced Salt Solution supplemented with antibiotic-antimycotic solution, Invitrogen Life Technologies, Carlsbad, Calif.), stored at 40 C and processed within 12 h after collection. Each cord was first cut into 2 cm pieces and each of these pieces cut open lengthwise and placed with its inner surface facing down in a 60 mm Petri dish containing an enzymatic solution. The enzymatic solution comprised of 2 mg/ml collagenase type I, 2 mg/ml collagenase type IV and 100 IU/ml hyaluronidase (Sigma, Mo.) in DMEM High glucose medium (Invitrogen). The umbilical blood vessels were not removed. The dishes were then incubated at 37° C. for 30-45 min to facilitate detachment and loosening of the Wharton's jelly into the culture medium. The gelatinous Wharton's jelly was then collected into sterile syringes and passed through hypodermic needles to and fro to separate the hWJSCs. The isolated hWJSCs were cultured in sterile tissue culture flasks [Becton Dickinson (BD) Franklin Lanes, N.J.] using hWJSC culture medium comprised of DMEM-high glucose medium supplemented with 20% fetal bovine serum (FBS), 16 ng/ml basic fibroblast growth factor (Millipore Bioscience Research agents, Temecula, Calif.), 1% non-essential amino acids, 2 mM L-glutamine, 0.1 mM 3-mercaptoethanol, 1% insulin-transferrin-selenium and 1% antibiotic-antimycotic mixture [penicillin (100 units/ml), streptomycin (100 µg/ml) and amphotericin B (0.25 µg/ml)](Invitrogen). After establishment of confluent monolayers the hWJSCs were detached from the plastic dishes with trypsin-EDTA (TrypLE™ Express, Invitrogen), dissociated, washed and seeded on 0.1% gelatin-coated tissue culture plates in a basal medium devoid of proteins comprised of DMEM-high glucose, 10% knockout serum replacement (KOSR), 1% L-glutamine and 1% antibioticantimycotic mixture (KOSR medium, Invitrogen) for all the experiments of the present study. A protein-free basal medium was used so as to take advantage of the various proteins released by the hWJSCs.

Human Keloid Cells

Ethical approval for the use of keloid tissues from consenting patients was also given by the Institutional Domain Specific Review Board (DSRB), Singapore. The keloid tissues were collected in HBSS (Invitrogen) and adherent and sphere cultures were set up according to the method of Zhang et al (2009). The sample was cut into 2 to 3 cm pieces, washed with fresh HBSS and then exposed to 3 mg/ml dispase (Invitrogen) overnight at 4° C. After overnight incubation, the epidermis was manually removed and the dermis minced into small pieces (1 mm3). The pieces were placed in collagenase type I (4 mg/ml) (Sigma Chemical Co, MO) and incubated at 37° C. in a 5% CO2 in air atmosphere for 2 h. After enzymatic digestion the cell suspension was centrifuged at 300×g for 5 min and the cell pellet resuspended in DMEM low glucose (Invitrogen) supplemented with 10% fetal bovine serum (FBS) (Biochrom AG, Berlin, Germany). The cell suspension was then filtered through a 70 µm cell strainer [Becton Dickinson (BD), USA], centrifuged at 300×g for 5 min, supernatant discarded, and the cells cultured under two different conditions (adherent and sphere culture).

Adherent Culture

Keloid cells were re-suspended in DMEM medium supplemented with 10% FBS, 100 u/ml penicillin, 100 µg/ml streptomycin, 2 mM L-glutamine, 100 mM non-essential amino acids (NEAA), 550 µM 2-mercaptoethanol (Invitrogen) and seeded into 100 mm plastic tissue culture Petri dishes (BD). The dishes were incubated at 37° C. in a 5% $CO_2$ in air atmosphere and when they attached to the plastic dishes their morphology and growth were monitored daily and photographed under inverted phase contrast optics.

Sphere Culture

Keloid cells were re-suspended in a combination of equal parts (v/v) of DMEM-low glucose and Ham's F12 (Millipore Bioscience Research Agents, Temecula, Calif.), and then supplemented with 40 ng/ml fibroblast growth factor-2 (FGF-2) (Millipore), 20 ng/ml, epidermal growth factor (EGF) (Miltenyl Biotech Asia Pacific Pte Ltd), antibiotic/antimycotic mixture (Invitrogen) and then seeded into sterile 6-well plates (BD). The plates were incubated at 37° C. in a 5% $CO_2$ in air atmosphere and when the cells started to produce spheres their morphology and growth were monitored and photographed under inverted phase contrast optics.

Human Foreskin Fibroblast Cells

Human foreskin fibroblasts (CCD-112sk) (abbreviated as CCD) were obtained from the American Type Culture Collection (ATCC, MD) to act as controls and ethical approval for their use was given by the National University of Singapore Institutional Review Board (NUSIRB). The commercial frozen CCDs were thawed and cultured in sterile tissue culture flasks (BD) in DMEM-high glucose medium supplemented with 10% FBS, 2 mM L-glutamine and antibiotic-antimycotic mixture (Invitrogen).

Labelling of hWJSCs with Green Fluorescence Protein (GFP)

hWJSCs were transfected with a lentiviral vector for the green fluorescence protein (GFP). Briefly, lentiviral vectors were produced by transient transfection of Lenti-X™ 293T cells (Clontec Laboratories Inc, Mountain View, Calif.). hWJSCs ($5 \times 10^6$ cells/plate) were seeded in 10 cm tissue culture plates 24 h before transfection. Transfection was performed using the calcium phosphate precipitation method. Cells were replaced with fresh medium at 14-16 h after transfection. The supernatant was filtered through a 0.45 mm filter and the titer of the supernatant of the 293T cells was determined using flow cytometry. The hWJSCs were infected with unconcentrated lentiviral supernatant at a multiplicity of infection (MOI) of 5-10.

Preparation of hWJSC and CCD Conditioned Medium and Cell-Free Lysate hWJSCs and CCDs at passages 3-4 (P3-P4) were grown to 80% confluence in basal medium with/without KOSR and the medium separated after 72 h as hWJSC conditioned medium (hWJSC-CM) and CCD conditioned medium (CCD-CM) respectively. The conditioned media were filter-sterilized using a 0.22 µm Millex-GP syringe filter (Millipore, Billerica, Mass.) and the pH and osmolality of the media standardised before use in experiments. Both hWJSC-CM and CCDCM were diluted 1:1 v/v in basal medium with/without KOSR and used as 50% hWJSC-CM and 50% CCD-CM for all experiments.

hWJSC and CCD cell-free lysates (hWJSC-CL; CCD-CL) were prepared from early passages of hWJSCs and CCDs (P3-P4) using a mammalian cell extraction kit (Bio-Vision, Mountain View, Calif.) that contained a protease inhibitor cocktail and dithiothreitol. Briefly, the cultured cells were washed once with phosphate buffered saline that contained no calcium and magnesium (PBS(−)), disassociated with trypsin (TrypLETM Express, Invitrogen Life Technologies, Carlsbad, Calif.) and centrifuged at 500 g for 5 min to obtain a cell pellet. The pellet was re-suspended in 100 µl of the cell lysis buffer provided with the kit and pipetted up and down several times and then incubated in ice for 15 min. The contents were then centrifuged at 12,000 g for 5 min (Eppendorf, Germany) and the clear supernatant (cell-free lysate) separated and stored at −80° C. until use. The hWJSC-CL was diluted in KOSR medium to yield a total protein content of 15 µg/ml which was measured using a Nanodrop™ spectrophotometer (Nanodrop Technologies, Wilmington, DW).

Interaction of keloid cells with hWJSCs, hWJSC-CM and hWJSC-CL

Experimental Design

Adherent cultures of keloid cells were separately exposed to hWJSC-CM and hWJSC-CL (treatments). Controls were keloid cultuires exposed to similar concentrations of (i) CCD-CM, (ii) CCD-CL and (iii) KOSR medium (untreated control). All dishes were monitored daily for 72 h and cells subjected to comparative analyses of morphological changes (inverted phase contrast optics), viability (MTT assay), cell cycle behavior (flow cytometry), CD markers (FACS), cell death (Annexin V-PI), TUNEL assay, scratch-wound assay, keratinocyte and TAF markers and gene expression profiles (qRT-PCR).

Statistically significant differences between the treatment and control arms for all evaluations were carried out using one-way ANOVA with Bonferroni's multiple comparisons post hoc analysis using the statistical package for Social Sciences (SPSS 13). The results were expressed as mean t SEM from three different replicates for individual experiments and a value of $p < 0.05$ was considered statistically significant.

Cell Morphology

The growth of the keloid cells exposed to treatments and controls were monitored daily for three days (72 h) and images of morphological changes of cell death captured at low and high magnifications using inverted phase contrast optics (Nikon Instruments, Tokyo, Japan).

CD Marker Analysis

Keloid cells of treatment and control dishes were dissociated into single cells with trypsin, washed in PBS (−) and blocked with 10% normal goat serum (NGS) (Invitrogen) for 30 min to prevent non-specific binding. The cells were then incubated with primary antibodies for a series of CD markers viz., CD14, CD29, CD34, CD44, CD45, CD73, CD90 and CD105 (Biolegend, San Diego, Calif.) for 1 h followed by incubation with Alexa Fluor® 488 (1:750) secondary antibody (Invitrogen) for 30 min. The cells were finally washed in PBS (−), resuspended in 10% NGS and filtered using a 70 µm nylon strainer (BD) to remove any cell clumps and analyzed by Fluorescence-activated cell sorting (FACS) using a CyAn™ ADP Analyzer (Beckman Coulter, Fullerton, Calif.).

Cell Viability

The viability of the keloid cells in treatment and control dishes was evaluated using a MTT reagent kit [3-(4,5-dimethylthiazolyl-2)-2,5-diphenyltetrazolium bromide] (Sigma, St. Louis, Mo.) according to the manufacturer's instructions. Briefly, 10 μl MTT reagent (final concentration of 0.5 mg/ml) was added to the culture dishes and incubated for 4 h until a purple precipitate was visible. The supernatant was separated and 100 μl of the detergent reagent was added to the cell pellet and incubated in the dark at room temperature for 2 h. Absorbance at 570 nm was spectrophotometrically measured using a microplate ELISA reader (pQuant-BioTek, Winooski, Vt.) with a reference wavelength of 630 nm.

Cell Cycle Analysis

Cell cycle analysis using flow cytometry of propidium iodide (PI) stained keloid cells was compared between treatments and controls. Briefly, the cells were disassociated with trypsin, washed and fixed with ice-cold 70% ethanol. The fixed cells were stained with 50 μg/ml PI in PBS containing 0.1% TritonX-100 and 50 μg/ml RNAse-A and then analyzed using a flow cytometer (Epics-Altra, Beckman Coulter, USA).

Annexin V-FITC Assay

The annexin V-FITC assay was carried out on keloid cells exposed to the treatments and controls to evaluate rates of apoptosis. Briefly, the keloid cells were dissociated with trypsin, washed once with PBS (−) and then with Annexin V binding buffer (1×). The cells were stained with 5 μl Annexin V-FITC at room temperature for 15 min, counterstained with PI (1 μg/mL) and analyzed using a CyAn™ ADP Analyzer.

TUNEL Assay

The degree of DNA fragmentation leading to apoptosis in keloid cells exposed to treatments and controls was evaluated with the DeadEnd™ Fluorometric TUNEL System kit (Promega Corp, WI, USA) that detects TdT (terminal deoxynucleotidyl transferase)-mediated dUDP nick-end labeling (TUNEL)-positive cells. Briefly, the keloid cells were disassociated, washed and fixed with 4% methanol-free formaldehyde solution for 25 min at 4° C. followed by addition of Triton X-100 solution for 5 min at 4° C. Labelling of the DNA fragments was carried out by treating the cells with fluorescin-12dUTP and TdT for 1 h at 37° C. in a humidified chamber in the dark. The reaction was stopped by the addition of sodium chloride-sodium citrate solution, the cells washed thrice and then stained with PI (1 μg/ml) in PBS containing DNase-free RNase (250 g/ml) for 15 min at room temperature in the dark. TUNEL positive cells were analyzed under a fluorescence microscope.

Scratch-Wound Assay

Keloid cell monolayers were exposed to hWJSC-CM in conventional scratch-wound assays (Cory, *Meth in Molec Biol,* 769:25-30 (2011)) to find out whether their cell migration and growth was inhibited. Keloid cells were first seeded at a density of $0.5 \times 10^6$ cells in 60 mm Petri dishes (Nalgene NUNC International, Rochester, N.Y.) and monolayers established within 24-48 h. Uniform linear scratches were made on the keloid monolayers vertically from top to bottom in the midline with a 2 ml graduated serological pipette. The cell debris was washed away gently with PBS and the medium of scratched dishes changed to the treatment (hWJSC-CM) and controls (CCD-CM; untreated). The dishes were incubated at 37° C. in a 5% CO2 in air atmosphere for 72 h and cell migration from the edges of the scratches monitored regularly and photographs taken under inverted phase contrast optics until full closure of the vacant areas. Digitized images of at least 5 random fields within the scratches were taken every 24 h using inverted phase contrast optics until 72 h or full closure of the scratches. Markings on the Petri dishes were used as reference points to monitor the same fields every 24 h. The mean±SEM percentage extent of closure of the scratches at 24, 48 and 72 h were calculated from the digitized images using an image software program (Walter et al., *Exp Cell Res,* 316:1271-1281 (2010)). Three replicates were carried out for each assay.

Gene Expression

Immunohistochemistry and quantitative real time polymerase chain reaction (qRT-PCR) were used to evaluate keratinocyte and TAF marker changes and apoptotic and autophagic gene expression in treatments and control dishes to understand changes in behavior of the keloid cells exposed to hWJSC-CM and hWJSC-CL.

For immunohistochemistry, the keloid cells were analyzed for the keratinocyte markers (cytokeratin, involucrin, filaggrin), TAF markers [fibroblast specific protein (FSP), thrombospondin (Tn-C) and VEGF] and autophagy markers (Beclin-1, LC3B) using their respective primary monoclonal and polyclonal antibodies. The keloid cells were washed in PBS and incubated with 4'-6-Diamidino-2-phenylindole (DAPI; 0.5 μg/ml) (Molecular probes, Invitrogen) for 5 min at room temperature, washed again with PBS and then analyzed using fluorescence microscopy.

For qRT-PCR analysis the total RNA of keloid cells in treatment and control dishes was extracted using TRIzol™ reagent (Invitrogen). RNA quality and quantity were measured using a Nanodrop™ spectrophotometer (Nanodrop technologies, Wilmington, DW) and all samples were treated with DNase-I prior to first strand cDNA synthesis with random hexamers using the SuperScript™ first strand synthesis system (Invitrogen). Primer sequences were taken from earlier published studies (Gauthaman et al. *J Cell Biochem,* 113:2027-2039 (2012b); Subramanian et al. *J Cell Biochem,* 113:1886-1895 (2012)). qRT-PCR analysis was performed with the ABI PRISM 7500 Fast Real-Time PCR System (Applied Biosystems, Foster City, Calif.) using SYBR green and relative quantification was performed using the comparative CT (2-AACT) method.

In Vivo Studies

A human keloid xenograft mouse model was used to evaluate keloid cell inhibition in vivo by hWJSCs. All animal procedures were carried out after approval from the National University of Singapore Institutional Animal Care and Use Committee (NUS-IACUC). Eight 7-8 week old severely combined immunodeficient (SCID) mice from the Animal Research Centre, Singapore were divided into two groups of four mice each: Gp 1 (Treatment): Keloid cells ($4 \times 10^6$)+hWJSCs ($4 \times 10^6$)+Matrigel; Gp 2 (Control): Keloid cells ($4 \times 10^6$)+Matrigel. The cells were administered in a final volume of 100 μl of matrigel. The cells and matrigel were injected into the subcutaneous regions of both hind limbs in each mouse. The animals were sacrificed at the end of the study period (7 weeks) using an inhalational overdose of carbon dioxide. Any keloid tumour-like masses were collected from the subcutaneous regions for histological analysis.

Results

Keloid Cell Characterization

Before Exposure to hWJSC-CM and hWJSC-CL

Figure 15A:
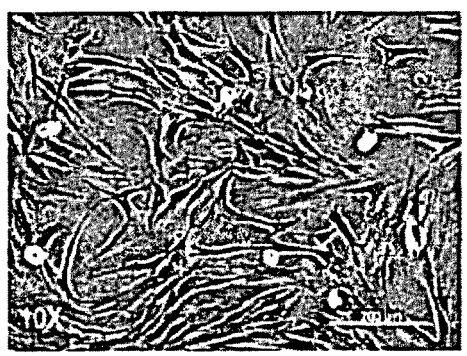
FIGS. 15A-15D: (15A) Phase-contrast inverted optical images of human keloid cells attached to plastic and showing spindle-shaped fibroblast-like cell morphology under adherent culture conditions. (15B) Keloid cells clustered together into spheres in suspension under here culture conditions. (15C) FACS analysis for CD markers of keloid cells in adherent culture and (15D) sphere culture. Data are from three independent experiments and each contour map represents the percentage of FITC-positive cells against unstained controls for each CD marker.
Figure 15B:
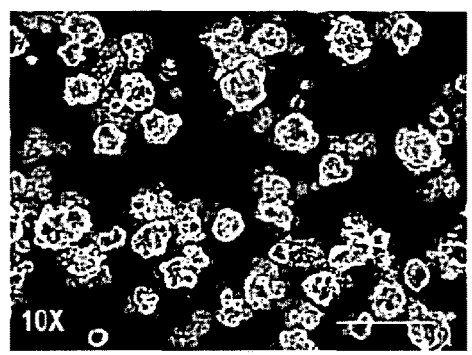
Figure 15C:
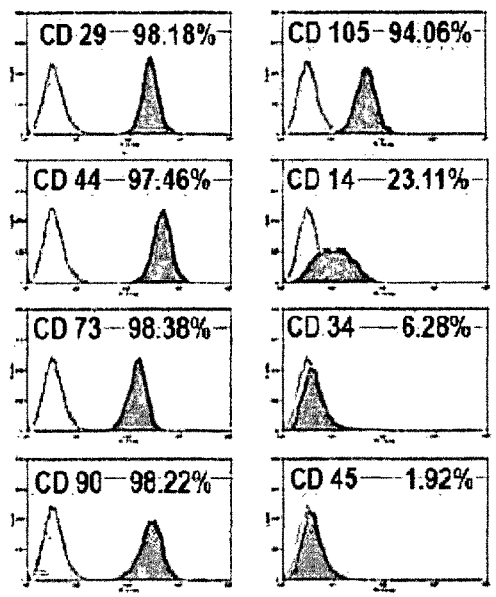
Figure 15D:
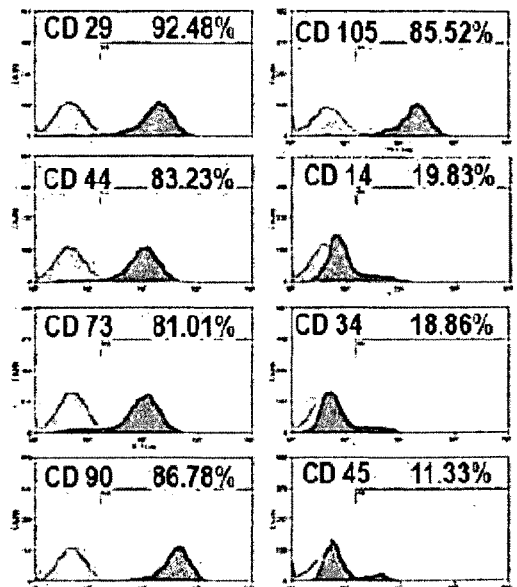

Untreated keloid cells that were not exposed to treatments (hWJSC-CM and hWJSC-CL) attached well to the plastic and became confluent monolayers with long spindle-shaped fibroblastic morphology (FIG. 15A) and untreated keloid cells in sphere cultures clustered together to form several translucent spheres of different sizes (FIG. 15B). Flow cytometry analysis of keloid cells in adherent and sphere culture showed high level expression of the mesenchymal stem cell (MSC) CD markers CD29, CD44, CD73, CD90 and CD105 (Adherent culture: 94.06 t 1.08% to 98.38±1.31%; Sphere culture: 81.01±1.17% to 92.48±2.63%) and low level expression for CD14, CD34 and CD45 (Adherent culture: 1.92±0.61% to 23.11±0.89%; Sphere culture: 11.33±0.74% to 19.38±1.04%) (FIGS. 15C, 15D).

After Exposure to hWJSC-CM and hWJSC-CL

Figures 16A, 16B:
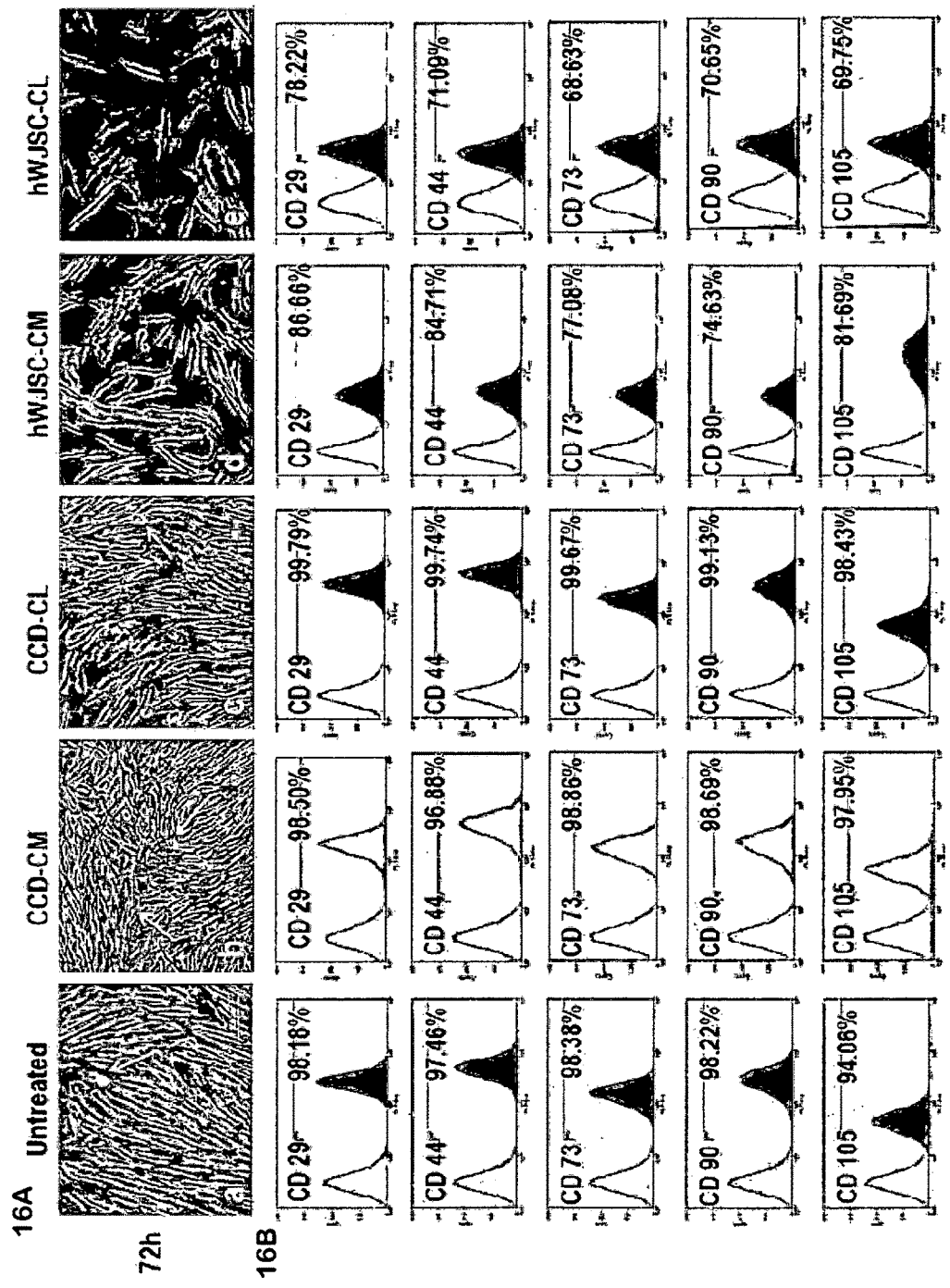
FIGS. 16A-16B: (16A) Phase contrast images of morphological changes of human keloid cells exposed to hWJSC-CM and hWJSC-CL. a-c. Note that keloid cells of controls (untreated, CCD-CM, CCD-CL) formed complete confluent monolayers with their typical fibroblastic morphology and several circular mitotic cells (white arrows) at 72 h. d, e. Keloid cells exposed to hWJSC-CM and hWJSC-CL had decreased cell numbers, no mitotic cels and underwent cell death early. (16B) The expression of CD markers (CD29, CD44, CD73, CD90, CD105) of keloid cells remained high in controls (Untreated, CCDCM, CCD-CL) while those of the treatment groups (hWJSC-CM and hWJSC-CL) decreased.

The keloid cells of adherent cultures exposed to hWJSC-CM and hWJSC-CL showed decreased numbers of mitotic cells compared to controls (FIG. 16A). When keloid cells in adherent culture were exposed to hWJSC-CM and hWJSC-CL the highly expressed MSCCD markers (CD29, CD44, CD73, CD90 and CD105) decreased significantly to 74.63±3.48%-86.66±1.97% and 69.75±4.57%-78.22±3.97% respectively ($p<0.05$) compared to the controls (CCD-CL: 98.43±2.76%-99.79±0.18%; CCD-CM: 96.88±2.07%-98.86±1.33%; Untreated: 94.06±1.08%-98.38±1.31%) (FIG. 16B).

Cell Viability

Figures 17A, 17B, 17C, 17D, 17E, 17F:
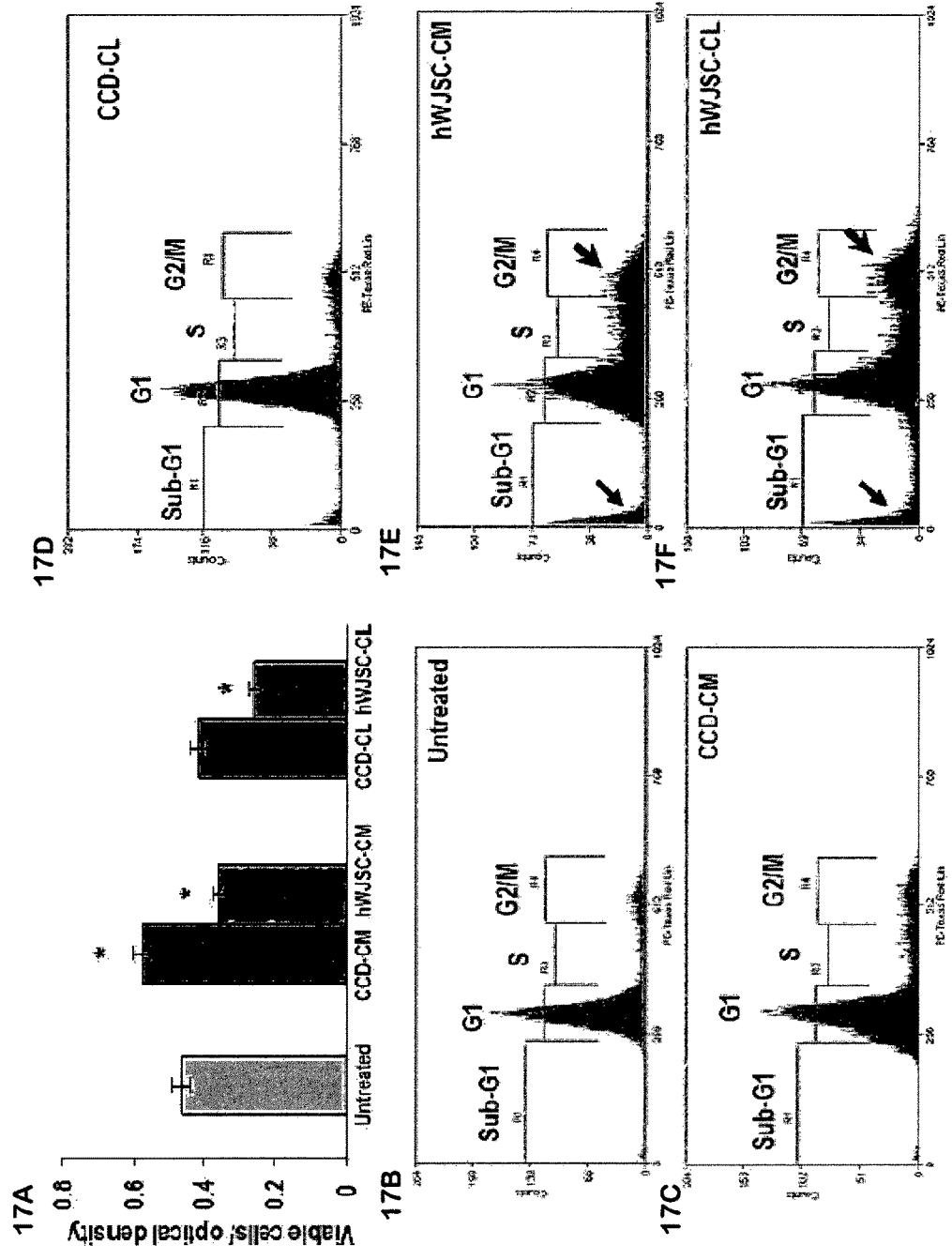
FIGS. 17A-17F: (17A) Histogram showing cell proliferation (MTT assay) of human keloid cells exposed to hWJSC-CM and hWJSC-CL significantly decreased at 72 h compared to controls (untreated, CCD-CM, CCD-CL). All values are mean±SEM from three different replicates. *p<0.05. (17B-17F) Cell cycle analysis (Flow cytometry-PI) showing human keloid cells exposed to treatments (hWJSC-CM and hWJSC-CL) had increased sub-G1 (thin arrows) and G2/M (thick arrows) compared to controls (untreated, CCD-CM, CCD-CL).

The MT assay of keloid cells exposed to hWJSC-CM and hWJSC-CL showed decreases in cell viability at 72 h compared to their respective controls. The mean±SEM decreases in cell viability were 0.46±0.03 for untreated; 0.58±0.02 for CCD-CM; 0.42±0.02 for CCDCL; 0.36±0.02 for hWJSC-CM and 0.26±0.19 for hWJSC-CL. These mean decreases in cell viability between treatment and control groups were statistically significant (FIG. 17A).

Cell Cycle Analysis

Keloid cells in control dishes showed normal cell cycle profiles while the cells cultured in the treatments (hWJSC-CM and hWJSC-CL) showed increased peaks in the sub-G1 and G2/M phases compared to their respective controls. The percentage increases for the sub-G1 phase were hWJSC-CM: 11.18±2.34% and hWJSC-CL: 15.16±3.07% and for the G2/M phase were hWJSC-CM: 17.80±1.94% and hWJSC-CL: 18.09±2.74% (FIGS. 17B-17F).

Annexin V-FITC Assay

Figure 18A:
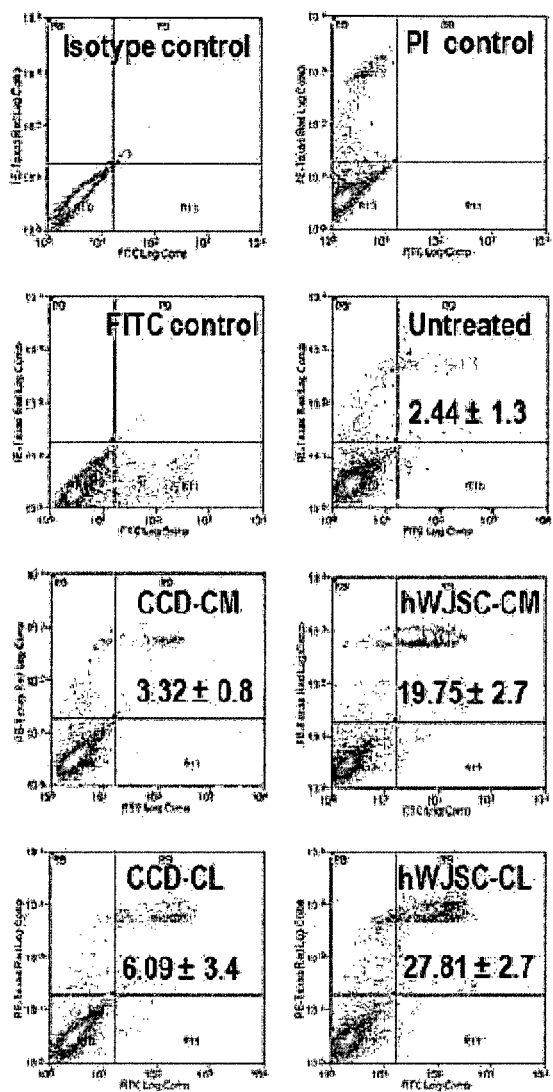
FIGS. 18A-18B: (18A) Contour plots (Annexin V-FITC flow cytometry) of human keloid cells showing significantly higher positive cells when exposed to hWJSC-CM and hWJSC-CL compared to controls. Values are mean±SEM from three different replicates. (18B) Images of TUNEL positive human keloid cells when exposed to hWJSC-CM and hWJSC-CL compared to controls (untreated, CCD-CM, CCD-CL). DNAse treated cells were used as positive controls (PC).

Keloid cells treated with hydrogen peroxide (10 mM) for 2-3 h were used as positive control and they showed positive staining for Annexin V-FITC with a lateral shift of the histogram compared to unstained negative controls. Contour plots of keloid cells exposed to hWJSCCM and hWJSC-CL treatments showed significantly greater mean±SEM percentages of Annexin V-FITC positive cells compared to controls (19.75±2.7 to 27.81±2.7 vs 2.44±1.3 to 6.09±3.4) ($p<0.05$) (FIG. 18A).

TUNEL Assay

Figure 18B:
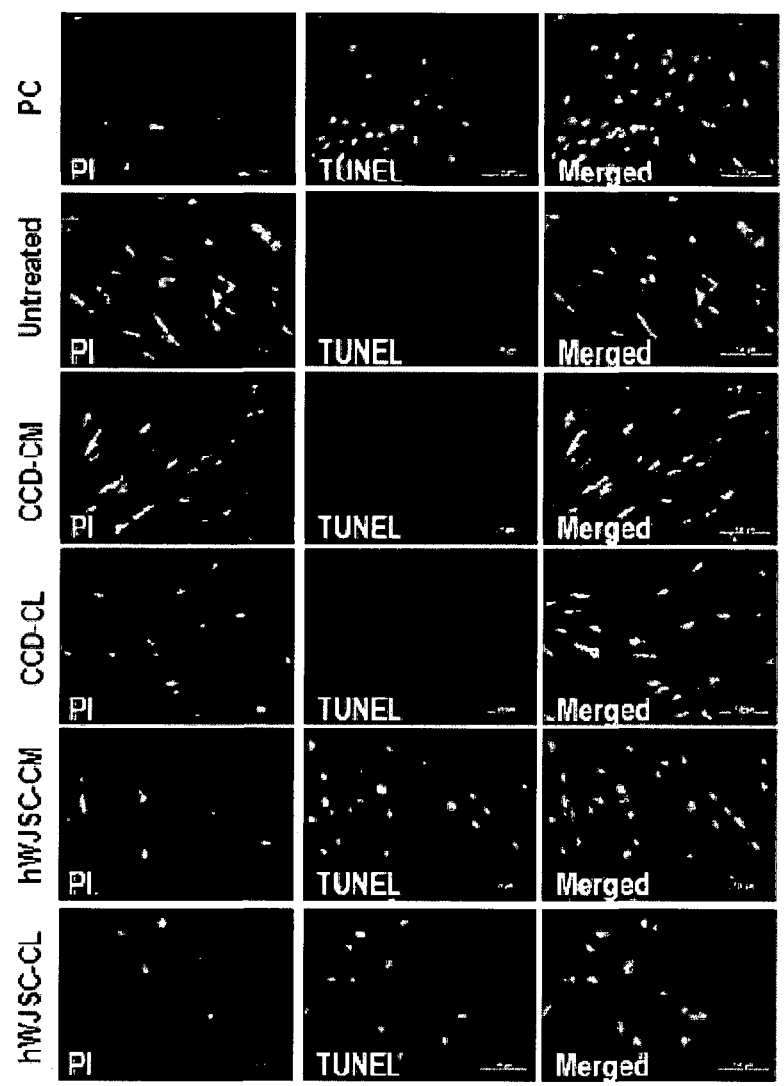

Keloid cells were treated with DNAse to act as positive controls showing positive staining for the TUNEL assay. Keloid cells exposed to the treatments (hWJSC-CM and hWJSC-CL) showed positive TUNEL cells compared to controls (FIG. 18B).

Scratch-Wound Assay

Figure 19A:
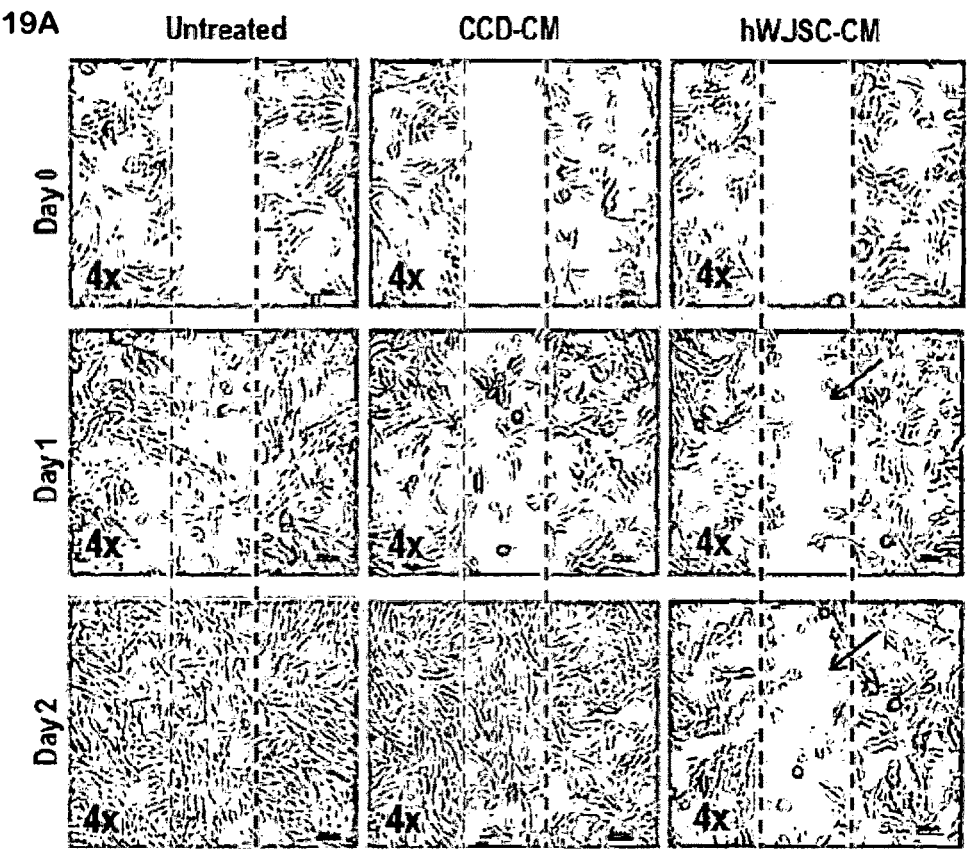
FIGS. 19A-19C: (19A) Phase contrast images of scratch-wound assay showing human keloid cells migrating from edges of scratches into vacant areas with complete closure by 48 h in controls (untreated, CCD-CM, CCD-CL) whereas keloid cells of treatments (hWJSC-CM and hWJSC-CL) stopped their migration and vacant areas were not covered at 48 h (arrows). (19B) Immunocytochemistry images of human keloid cells showing positive keratinocyte-related markers (cytokeratin, involucrin, filaggrin) and (19C) TAF-related markers (FSP), (Tn-C) and VEGF.

The keloid cells of the controls (untreated and CCD-CM) migrated from the edges of the scratches and completely covered the vacant areas within 48 h while the keloid cell migration of hWJSC-CM treated dishes was slower and decreased with no complete coverage of the scratched areas after 48 h (FIG. 19A).

Immunohistochemistry

Figure 19B:
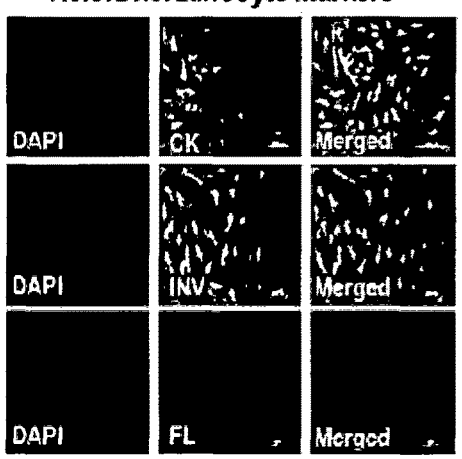
Figure 19C:
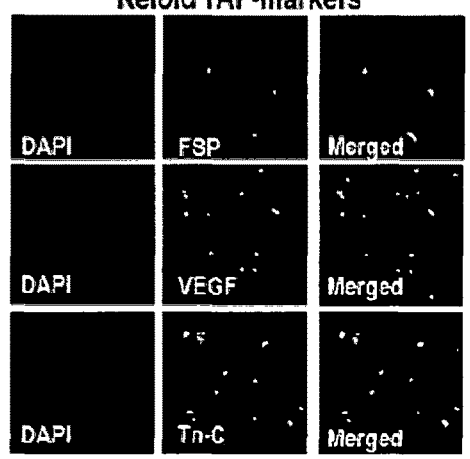
Figures 20A, 20B, 20C:
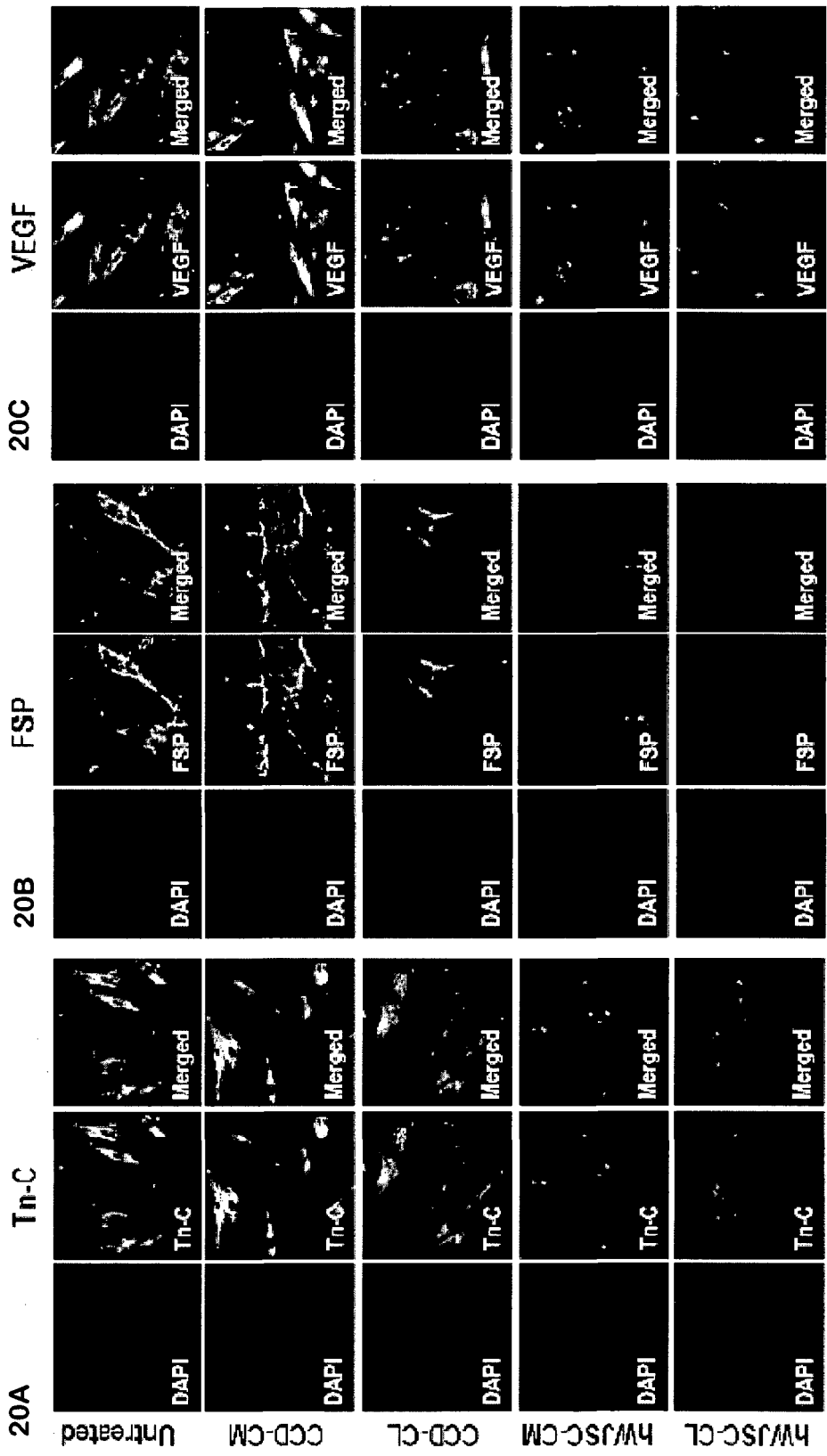
FIGS. 20A-20C: Immunocytochemistry images showing weakly positive TAF-related markers (Tn-C (20A), FSP (20B) and VEGF (20C)) in human keloid cells exposed to hWJSC-CM and hWJSC-CL for 72 h compared to controls (untreated, CCD-CM, CCD-CL).
Figures 21A, 21B:
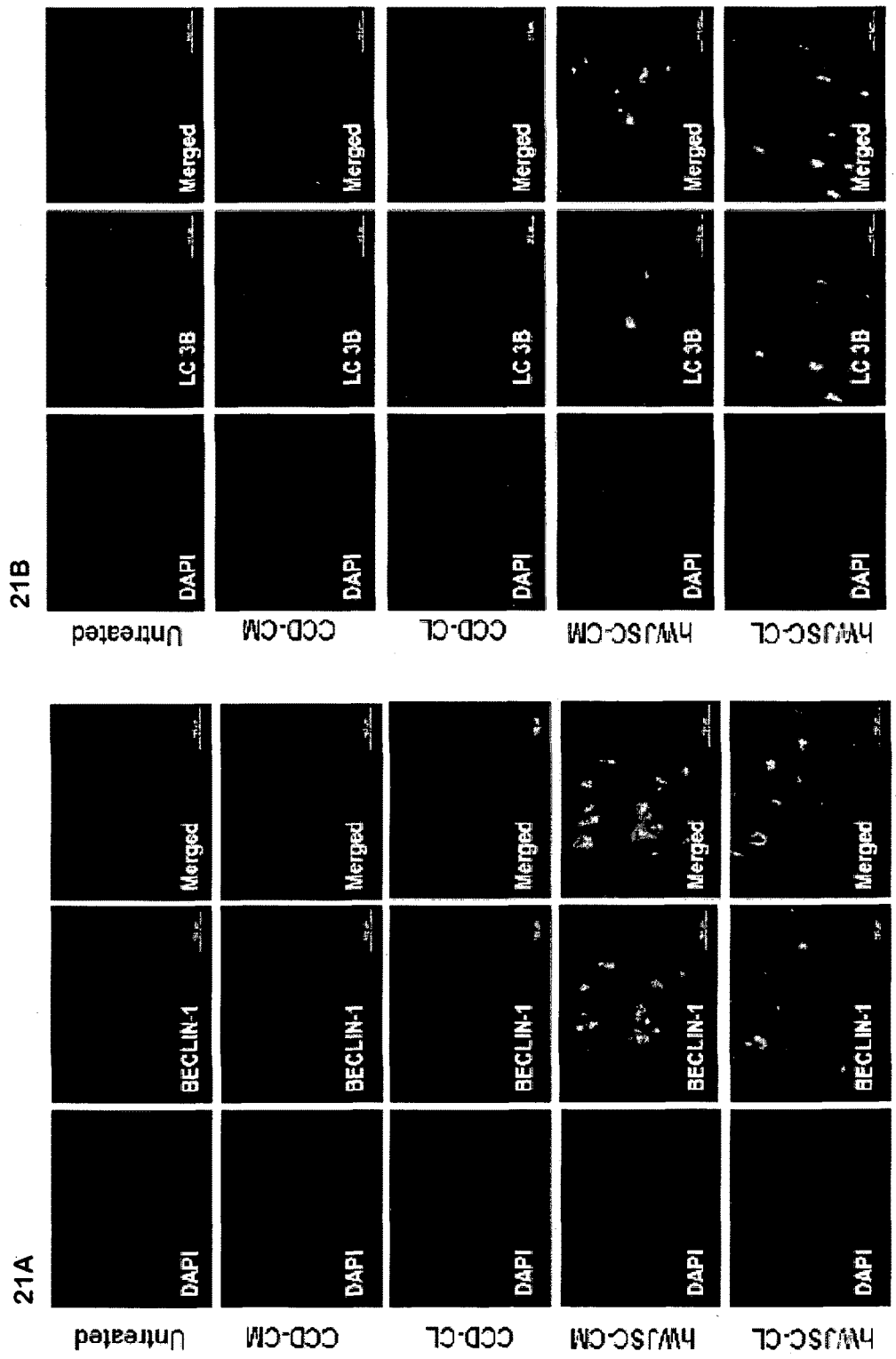
FIGS. 21A-21B: Immunohistochemistry images of human keloid cells exposed to hWJSC-CM and hWJSC-CL showing positive staining for BECLIN-1 (21A) and LC3B (21B) compared to controls (untreated, CCD-CM, CCD-CL).

Immunohistochemistry of untreated keloid cells showed positive human keratinocyte-related markers (cytokeratin, involucrin and filaggrin) (FIG. 19B) and TAF markers (FSP, Tn-C and VEGF) (FIG. 19C). However when keloid cells were treated with hWJSC-CM and hWJSC-CL for 72 h they showed weekly positive TAF markers (Tn-C, FSP and VEGF) (FIG. 20A-20C) and highly positive autophagy-related markers (BECLIN-1 and LC3B) compared to controls (FIG. 21A-21B).

Quantitative Real Time Polymerase Chain Reaction (qRT-PCR)

Figures 22A, 22B:
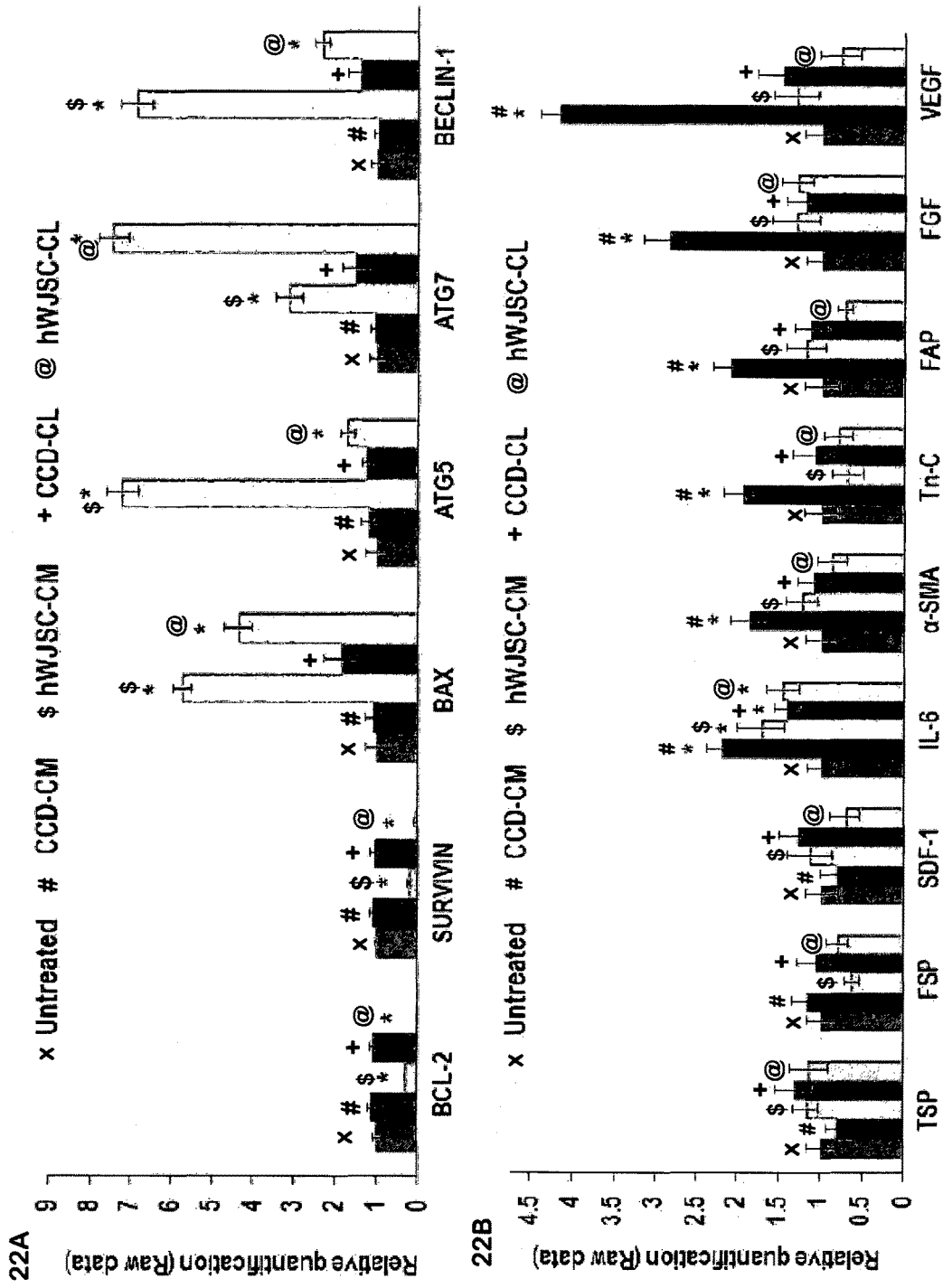
FIGS. 22A-22B: (22A) Gene expression profiles (qRT-PCR) showing downregulation of the antiapoptotic-related genes (BCL2, and SURVIVIN) and upregulation of the pro-apoptotic and autophagy-related genes (BAX, ATG5, ATG7, and BECLIN-1) in human keloid cells exposed to hWJSC-CM and hWJSC-CL for 72 h compared to controls (untreated, CCDCM, CCD-CL). (22B) qRT-PCR showing upregulation of TAF-related genes (IL-6, a-SMA, Tn-C, FAP, FGF, and VEGF) in human keloid cells exposed to hWJSC-CM and hWJSCCL compared to controls (untreated, CCD-CM, CCD-CL). Data analysis and relative quantitation was done using the comparative Ct (DDCt) method.

Gene expression analysis using qRT-PCR showed that the anti-apoptotic-related genes (BCL2, and SURVIVIN) were downregulated and the pro-apoptotic and autophagy-related genes (BAX, ATG5, ATG7, and BECLIN-1) were upregulated in the keloid cells treated with hWJSC-CM and hWJSC-CL for 72 h compared to controls (FIG. 22A). The fold decreases in expression levels for anti-apoptotic-related genes ranged from 0.048 to 0.34 and the fold increases for pro-apoptotic and autophagy-related genes ranged from 0.74 to 6.47. The fold differences for each gene were statistically significant from controls (FIG. 22A).

qRT-PCR of the TAF-related genes confirmed the immunohistochemistry results. The TAF genes (IL-6, a-SMA, Tn-C, FAP, FGF and VEGF) were downregulated in the keloid cells exposed to the treatments (hWJSC-CM and hWJSC-CL) compared to controls (FIG. 22B).

Keloid Inhibition In Vivo

Figures 23A, 23B, 23C, 23D:
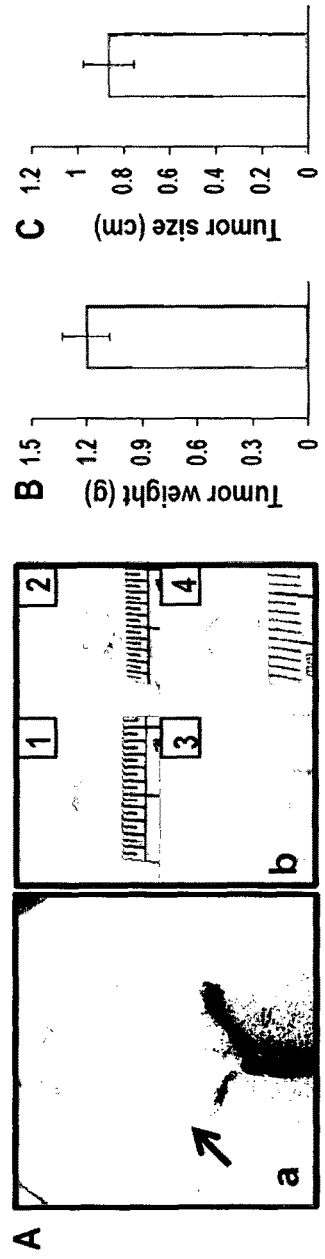
FIG. 23A-23D: (23Aa) Keloid tumour-like masses were formed in both hind limbs for control arm (keloid cells+matrigel) and (23Ab) Keloid tumours removed from control arm mice. (23B) Histogram showing weight of tumour-like masses. (23C) Histogram showing size of tumour-like masses. (23D) H & E staining of tumor-like masses derived from control arm showing nodules of fibrillary collagen (23Da,b) broad glassy collagen and basal cell vacuolar changes (23Dc-f).

The SCID mice in Gp 2 (Control) that received keloid cells+matrigel produced circular tumours ranging from 0.76 to 0.98 cm in diameter in 3-4 weeks in the subcutaneous regions of 6 out of 8 injection sites (4 animals) (FIG. 23A a,b) while those mice of Gp 1 (Treatment) receiving keloid cells+hWJSCs+matrigel did not produce any tumour-like masses in all eight injection sites of the 4 animals. The tumour-like masses of the controls on histology showed the typical salient morphological features of keloids which included fibrillary collagen, broad glassy collagen and basal cell vacuolar changes (FIG. 23D a-f) described by Moshref and Mufti *JKAU Med Sci*, 17:3-22 (2010).

The weights and sizes of tumors of the Gp 2 (Control A) (keloid cells+matrigel) were 1.12±0.13 g and 0.76 to 0.98 cm. (FIG. 22B, C).

Discussion

The fact that the percentage expression of the key keloid CD markers (CD29, CD44, CD73, CD90 and CD105) decreased in the presence of hWJSC-CM and hWJSC-CL compared to controls indicates that the stemness characteristics, self-renewal and differentiation potential of the keloid cells was altered by putative anti-tumorigenic agents in the hWJSC-CM and hWJSC-CL. Also, the high percentage of cell death observed in the sub-G1 phase of the cell cycle in hWJSC-CM and hWJSC-CL treated keloid cells indicated that the cells were undergoing apoptosis. The gene expression profiles showed that the antiapoptotic-related genes (BCL2, and SURVIVIN) were downregulated and the pro-apoptotic and autophagy-related genes (BAX, ATG5, ATG7, and BECLIN-1) were upregulated in the keloid cells exposed to hWJSC-CM and in hWJSC-CL further confirming that the keloid cell death induced by the hWJSCs was via apoptotic and autophagy mechanisms.

The fact that there was no keloid formation in the xenograft mice receiving hWJSC administration suggests that hWJSCs inhibit the growth of keloid cells and hence are of therapeutic value against keloids in clinical settings. The results of the present study indicate that hWJSCs and hWJSC-CM alter the nature of the benign tumorigenicity of keloid cells making them lose their neoplastic features and becoming non-invasive. As shown herein, specific miRNA clusters (miR-106a-363, miR-17-92, miR-106b-25, miR-302-367, miR-21, miR-34a and the let-7 family) were highly expressed in hWJSCs. The miR-106a-363 and miR-17-92 clusters are involved in cell proliferation and growth thus likely playing a role in the wound healing process and miR-34a and the let-7 family are involved in anticancer processes.

As also shown herein, approximately $4.6 \times 10^6$ fresh live hWJSCs can be harvested from 1 cm of human umbilical cord and hWJSCs are proliferative with short population doubling times (PDT) of 24 h (Fong et al., *Reprod Biomed Online*, 21:391-401 (2010)). They can thus be scaled up in large numbers for clinical application. In addition, they can be differentiated into keratinocytes in vitro using conventional protocols. Thus, because of their unique advantages over other stem cell types such as their availability in large numbers from discarded umbilical cords, high proliferation rates, multipotency, hypoimmunogenicity, non-tumorigenicity and antitumorigenecity hWJSCs have enormous clinical utility in the management of keloids.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A medical dressing comprising:
   a) (i) Wharton's jelly stem cells (WJSCs), (ii) a cell culture medium that has been conditioned with WJSCs, (iii) filtered supernatant from a lysate of living WJSCs, (iv) a cell culture medium that has been conditioned with a co-culture of WJSCs and one or more of living skin cells, dying skin cells or keloid cells, for a period of time from about 1 hour to about 14 days to release biologically active components into the medium, wherein the cells are then removed from the medium, or (v) a combination thereof, and
   b) a scaffold formed from a mixture comprising polycaprolactone (PCL) and aloe vera powder, wherein the scaffold is impregnated with the cells, culture medium and/or lysate of a).

2. The medical dressing of claim 1 wherein the scaffold formed from a mixture comprising PCL and aloe vera powder is a nanofibrous scaffold.

3. The medical dressing of claim 1 wherein the scaffold has a porosity of about 85% to 95%, a pore size of about 0.5 μm to about 10 μm, a fiber diameter of about 250 nm to about 650 nm, a fiber thickness of about 250 nm to about 650 nm, or combinations thereof.

4. The medical dressing of claim 1 wherein the lysate of WJSCs is obtained by contacting the WJSCs with a lysis buffer that lyses the WJSCs.

5. The medical dressing of claim 1 wherein for (iv) the co-culturing is under a normoxic or hypoxic environment.

6. The medical dressing of claim 1, wherein the period of time in (a)(iv) is from about 24 hours to about 72 hours.

7. A pharmaceutical composition comprising the medical dressing of claim 1.

8. A medical dressing comprising:
   a) (i) a cell culture medium that has been conditioned with Wharton's jelly stem cells (WJSCs) for a period of time to release biologically active components into the medium, wherein the WJSCs are then removed from the medium, (ii) filtered supernatant from a lysate from WJSCs, (iii) a cell culture medium that has been conditioned with a co-culture of WJSCs and one or more of living skin cells, dying skin cells or keloid cells, for a period of time from about 1 hour to about 14 days to release biologically active components into the medium, wherein the cells are then removed from the medium, or (iv) a combination thereof, and
   b) (i) a scaffold formed from a mixture comprising polycaprolactone (PCL) and aloe vera powder; or (ii) a scaffold consisting of PCL, wherein the scaffold is impregnated with the culture medium, lysate, and/or combination of a),
   wherein the WJSCs are a homogeneous population of WJSCs from Wharton's jelly.

9. The medical dressing of claim 8, wherein the period of time in (a)(iii) is from about 24 hours to about 72 hours.

10. A sterile pharmaceutical composition comprising the medical dressing of claim 8 and a physiologically acceptable carrier or excipient.

11. A method of treating a wound or suppressing scar formation at a wound, or both, in an individual in need thereof comprising contacting the wound with an effective amount of:
   A) a composition comprising:
      a) (i) Wharton's jelly stem cells (WJSCs), (ii) a cell culture medium that has been conditioned with WJSCs, (iii) filtered supernatant from a lysate of WJSCs, (iv) a cell culture medium that has been conditioned with a co-culture of WJSCs and one or more of living skin cells, dying skin cells or keloid cells, for a period of time from about 1 hour to about 14 days to release biologically active components into the medium, wherein the cells are then removed from the medium, or (v) a combination thereof, and
      b) a scaffold formed from a mixture comprising polycaprolactone (PCL) and aloe vera powder, wherein the scaffold is impregnated with the cells, culture medium and/or lysate of a); or
   B) a composition comprising:
      a) (i) a cell culture medium that has been conditioned with Wharton's jelly stem cells (WJSCs) for a period of time to release biologically active components into the medium, wherein the WJSCs are then removed from the medium, (ii) filtered supernatant from a lysate from WJSCs, (iii) a cell culture medium that has been conditioned with a co-culture of WJSCs and one or more of living skin cells, dying skin cells or keloid cells, for a period of time from about 1 hour to about 14 days to release biologically active components into the medium, wherein the cells are then removed from the medium, or (iv) a combination thereof, and
      b) (i) a scaffold formed from a mixture comprising polycaprolactone (PCL) and aloe vera powder; or (ii) a scaffold consisting of PCL, wherein the scaffold is impregnated with the culture medium, lysate, and/or combination of a),
      wherein the WJSCs are a homogeneous population of WJSCs from Wharton's jelly.

12. The method of claim 11 wherein the (i) scaffold formed from a mixture comprising PCL and aloe vera powder; or (ii) scaffold consisting of PCL is a nanofibrous scaffold.

13. The method of claim 1 wherein the scaffold has a porosity of about 85% to 95%, a pore size of about 0.5 μm to about 10 μm, a fiber diameter of about 250 nm to about 650 nm, a fiber thickness of about 250 nm to about 650 nm, or combinations thereof.

14. The method of claim 1 wherein the cell culture medium that has been conditioned with WJSCs is obtained by culturing WJSCs in one or more cell culture media for about 24 hours to 72 hours.

15. The method of claim 11 wherein the lysate of WJSCs is obtained by contacting the WJSCs with a lysis buffer that lyses the WJSCs.

16. The method of claim 11 wherein in A(a)(iv) or B(a)(iii) the co-culturing is under a normoxic or hypoxic environment.

17. The method of claim 11, wherein the period of time in A(a)(iv) and B(a)(iii) is from about 24 hours to about 72 hours.

18. A method of treating a scar in an individual in need thereof comprising contacting the scar with an effective amount of:
   A) a composition comprising:
      a) (i) Wharton's jelly stem cells (WJSCs), (ii) a cell culture medium that has been conditioned with WJSCs, (iii) filtered supernatant from a lysate of WJSCs, (iv) a cell culture medium that has been conditioned with a co-culture of WJSCs and one or more of living skin cells, dying skin cells or keloid cells, for a period of time from about 1 hour to about 14 days to release biologically active components into the medium, wherein the cells are then removed from the medium, or (v) a combination thereof, and
      b) a scaffold formed from a mixture comprising polycaprolactone (PCL) and aloe vera powder, wherein the scaffold is impregnated with the cells, culture medium and/or lysate of a); or
   B) a composition comprising:
      a) (i) a cell culture medium that has been conditioned with Wharton's jelly stem cells (WJSCs) for a period of time to release biologically active components into the medium, wherein the WJSCs are then removed from the medium, (ii) filtered supernatant from a lysate from WJSCs, (iii) a cell culture medium that has been conditioned with a co-culture of WJSCs and one or more of living skin cells, dying skin cells or keloid cells, for a period of time from about 1 hour to about 14 days to release biologically active components into the medium, wherein the cells are then removed from the medium, or (iv) a combination thereof, and
      b) (i) a scaffold formed from a mixture comprising polycaprolactone (PCL) and aloe vera powder; or (ii) a scaffold consisting of PCL, wherein the scaffold is impregnated with the culture medium, lysate, and/or combination of a),
      wherein the WJSCs are a homogeneous population of WJSCs from Wharton's jelly.

19. The method of claim 18 wherein the scar is a keloid.

20. The method of claim 18 wherein the (i) scaffold formed from a mixture comprising PCL and aloe vera powder; or (ii) scaffold consisting of PCL is a nanofibrous scaffold.

21. The method of claim 18 wherein in A(a)(iv) or B(a)(iii) the co-culturing is under a normoxic or hypoxic environment.

22. The method of claim 18, wherein the period of time in A(a)(iv) and B(a)(iii) is from about 24 hours to about 72 hours.

* * * * *